US012751927B2

(12) United States Patent
Irudayaraj et al.

(10) Patent No.: US 12,751,927 B2
(45) Date of Patent: Oct. 6, 2026

(54) POLYSACCHARIDE ENCAPSULATED OXYGEN NANOBUBBLES

(71) Applicant: THE BOARD OF TRUSTEES OF THE UNIVERSITY OF ILLINOIS, Urbana, IL (US)

(72) Inventors: Joseph Maria Kumar Irudayaraj, Champaign, IL (US); Muhammad Fayyaz, Urbana, IL (US); Michael Tsipursky, Champaign, IL (US); Wen Ren, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 597 days.

(21) Appl. No.: 18/254,278

(22) PCT Filed: Nov. 19, 2021

(86) PCT No.: PCT/US2021/060067

§ 371 (c)(1),
(2) Date: May 24, 2023

(87) PCT Pub. No.: WO2022/115323

PCT Pub. Date: Jun. 2, 2022

(65) Prior Publication Data

US 2024/0024251 A1 Jan. 25, 2024

Related U.S. Application Data

(60) Provisional application No. 63/118,221, filed on Nov. 25, 2020.

(51) Int. Cl.

| | |
|---|---|
| ***A61K 9/48*** | (2006.01) |
| ***A61K 9/00*** | (2006.01) |
| ***A61K 9/51*** | (2006.01) |
| ***A61P 27/02*** | (2006.01) |
| *B82Y 5/00* | (2011.01) |

(52) U.S. Cl.

CPC .......... *A61K 9/4816* (2013.01); *A61K 9/0048* (2013.01); *A61K 9/5161* (2013.01); *A61P 27/02* (2018.01); *B82Y 5/00* (2013.01)

(58) Field of Classification Search

CPC .. A61K 9/4816; A61K 9/0048; A61K 9/5161; A61P 27/02; B82Y 5/00

See application file for complete search history.

(56) References Cited

U.S. PATENT DOCUMENTS

| | | | |
|---|---|---|---|
| 8,486,444 | B2 | 7/2013 | Ottoboni et al. |
| 9,737,486 | B2 | 8/2017 | Bright et al. |
| 9,968,692 | B2 | 5/2018 | Irudayaraj et al. |
| 10,670,581 | B2 | 6/2020 | Irudayaraj et al. |
| 2010/0297193 | A1 | 11/2010 | Archambeau et al. |
| 2011/0165088 | A1 | 7/2011 | Ottoboni et al. |
| 2020/0009065 | A1 | 1/2020 | Polizzotti et al. |
| 2020/0249221 | A1 | 8/2020 | Irudayaraj et al. |

OTHER PUBLICATIONS

Zhou et al. (Formation of Stable Nanobubbles on Reconstituting Lyophilized Formulations Containing Trehalose), Journal of Pharmaceutical Science 105 (2016) 2249-2253.*

Dextran Wikipedia, 2025.*

Bhandari et al., "Hypoxia Re-Programming Oxygen Nanobubbles Sensitize Human Glioblastoma Cells to Temozolomide via Methylation Alterations," J. Bionanoscience, 11(5):337-345, Oct. 2017.

Bhandari et al., "Oxygen Nanobubble Tracking by Light Scattering in Single Cells and Tissues," ACS Nano., 11 (3):2682-2688, Mar. 2017.

Bhandari et al., "Oxygen Nanobubbles Revert Hypoxia by Methylation Programming," Scientific Reports, 7:9268, Aug. 2017, 14pgs.

Bhandari et al., "Ultrasound Beam Steering of Oxygen Nanobubbles for Enhanced Bladder Cancer Therapy," Nature Scientific Reports, 8(1):3112, Feb. 2018, 10pgs.

Cavalli et al., "Preparation and characterization of dextran nanobubbles for oxygen delivery", International Journal of Pharmaceutics, vol. 381, No. 2, 160-165, Nov. 2009.

Cavalli et al., "Preparation and Characterization of Dextran Nanobubbles for Oxygen Delivery," accessed on the internet at https://pubmed.ncbi.nlm.nih.gov/19616610, retrieved Jan. 21, 2022, 12pgs.

Ebina et al., "Oxygen and Air Nanobubble Water Solution Promote the Growth of Plants, Fishes, and Mice", PLoS ONE 8(6): e65339, Jun. 2013.

Fayyaz et al., "Dextran-Based Oxygen Nanobubbles for Treating Inner Retinal Hypoxia", ACS Appln. Nano Mater. 2021, 4, 6583-6593, Jul. 2021.

Fayyaz et al., "Dextran-Based Oxygen Nanobubbles for Treating Inner Retinal Hypoxia", Supporting Information, ACS Appl. Nano Mater., 4, 7, 6583-6593, Jul. 2021.

Hsu et al., "Self-assembled Shells Composed of Colloidal Particles: Fabrication and Characterization," Langmuir, 21 (7):2963-2970, Feb. 2005.

International Search Report and Written Opinion of the ISA/US in PCT/US2021/060067, dated Feb. 18, 2022, 10pgs.

(Continued)

*Primary Examiner* — Zohreh A Fay

(74) *Attorney, Agent, or Firm* — Haukaas Fortius PLLC; Michael Haukaas

(57) ABSTRACT

A unique class of perfluorocarbon-free Dextran-based oxygen nanobubbles (DONBs) and formulations thereof. The critical components in the formulation are chosen among the U.S. Food, and Drug Administration's (FDA) approved compounds, which provide a biocompatible environment for incorporating pharmaceutical agents. Moreover, the nanobubbles are fabricated with simple sonication and homogenization method that easily fulfills the current good manufacturing practices (cGMP) requirements, which will promote scaleup production for commercial manufacturing. The formulated DONBs release oxygen over an extended period to keep the partial pressure of oxygen within the inner retina high and thus preserve retinal tissue from ischemia.

20 Claims, 37 Drawing Sheets

(56) References Cited

OTHER PUBLICATIONS

Khan et al., "Oxygen-Carrying Micro/Nanobubbles: Composition, Synthesis Techniques and _Potential Prospects in Photo-Triggered Theranostics," Molecules, 23(9):2210, Sep. 2018.
Prato et al., "2H,3H-Decafluoropentane-Based Nanodroplets: New Perspectives for Oxygen Delivery to Hypoxic Cutaneous Tissues", PLoS ONE 10(3): e0119769, Mar. 2015.
Ulatowski et al., "Stability of nanobubbles generated in water using porous membrane system", Chemical Engineering & Processing: Process Intensification, 136, 62-71, Feb. 2019.
Zhou et al., "Long-Term Stability of Different Kinds of Gas Nanobubbles in Deionized and Salt Water", Materials, 14, 1808, Apr. 2021.
Extended Search Report and Written Opinion of the European Patent Office dated Apr. 18, 2024 in EP Application No. 21898955.6; 4pgs.

* cited by examiner (b)

(c)

POLYSACCHARIDE ENCAPSULATED OXYGEN NANOBUBBLES

RELATED APPLICATIONS

This application is a National Stage filing under 35 U.S.C. § 371 of International Application No. PCT/US2021/060067, filed Nov. 19, 2021, which claims the benefit of U.S. Provisional Patent Application No. 63/118,221, filed Nov. 25, 2020, which applications are incorporated herein by reference.

BACKGROUND OF THE INVENTION

The central retinal artery occlusion (CRAO) is an ophthalmological emergency and an important cause of acquired irreversible blindness. Occlusion of the central retinal artery from an embolus or a thrombus is similar to the pathophysiology of an ischemic stroke. Anatomically, the central retinal artery is a branch of the ophthalmic artery, and when occluded at the lamina cribrosa level within the optic nerve or the exit of the optic nerve, there is still choroidal circulation that supplies the outer retina with blood flow. Thus, the outer retinal layers are oxygenated, while inner retinal layers are not. Nevertheless, occlusions cause irreversible visual deficit due to the lack of perfusion, which gives rise to a hypoxic state resulting in damage to the inner retinal layers that result in blindness. CRAO is usually secondary to one or more systemic diseases such as carotid artery and cardiac valvular disease. Only −17% of the affected eyes have a meaningful improvement in visual acuity without any treatment prior to the onset of permanent damage, while the spontaneous resolution rate is 1-8%. Approximate incidence of CRAO has been reported as 1:1,000, 1:10,000, and 1.9:100,000 in the US population in various studies. This means that between 3,250 and 32,500 patients will be afflicted per year. Currently, there is no consistently effective treatment for CRAO. In a national survey, in the US, anterior chamber paracentesis (42% of cases) and ocular massage (66% of cases) are used to lower the intraocular pressure (IOP) with the hope to increase arterial perfusion pressure and move the obstruction downstream. Hyperbaric oxygen therapy was offered 7% of the time, while 9% of academic hospitals offer no treatment at all. Other treatments attempted include chemical fibrinolysis and laser-assisted thrombectomy, which also rarely works.

The majority of CRAOs are due to either embolic phenomena or, less frequently, thrombotic, or hypertensive events. After about 72 hours, the majority of the CRAOs appear reperfused when examined by fluorescein angiography, and this is sometimes due to the embolus passing or various retinal anastomoses taking over. Classic experiments with old, atherosclerotic rhesus monkeys showed that at 97 minutes, there was no damage to the retina, but the longer the occlusion after that, the more extensive the damage ultimately leading to blindness. After 4 hours, irreversible cell death has been noted, and in some cases, vision recovery was possible even after delays of 8-24 hours with intervention, possibly due to incomplete blockage of the vessel and some diffusion of oxygen from the choroid into outer retinal layers.

It has been shown that inspiration of 100% oxygen can, in the presence of acute central retinal artery obstruction, produce a normal partial pressure of oxygen ($pO_2$) at the surface of the retina via diffusion from the choroid; however, the macula region is much thicker with two ganglion layers and cannot obtain enough oxygen from the choroidal circulation. Occasionally, oxygenation has been achieved with the prompt institution of the highest fraction of inspired oxygen or with hyperbaric oxygen. Multiple case studies have shown improved visual acuity in certain patients receiving this treatment. However, the mechanism of action of how hyperbaric oxygen can help preserve retinal tissue is the presumed increase in $pO_2$ in choroidal circulation, which in turn will diffuse into the outer retina and sometimes can keep the inner retinal tissue oxygenated.

Hyperbaric oxygen cannot achieve the therapeutic level of oxygen in the inner retina. Furthermore, access to hyperbaric oxygen treatments is difficult and often requires a referral to a hyperbaric center, insurance formalities, and is not readily accessible to the majority of the patient population. Mitigating the severity of insult due to oxygen deficit, especially during the first few precious hours is vital, before the onset of permanent damage. Given current treatment options and understanding of the pathophysiology of CRAO and other ischemic conditions of the eye, we propose that focused oxygen delivery can preserve retinal tissue by temporizing and mitigating time-dependent ischemic insult to the retinal tissue.

Existing work on Perfluorocarbon (PFC) bearing oxygen nanobubbles yielded a significant improvement in the therapeutic outcome in treating solid tumors'. However, clinical trials of (PFC) nanoemulsions eventually failed as a result of various safety issues such as the adverse cerebrovascular effects on cardiopulmonary arrest and PFC-induced microvascular vasoconstriction. Alternatively, cellulose-based oxygen nanobubbles were synthesized in our prior work for cancer treatment but still contain minor amounts of PFC limiting its utility use for ocular treatment. Lipid-coated oxygen microbubbles (LOMs), clinically proven as ultrasound contrast agents and oxygen cargo carriers, have materialized as a new promising binary agent because they provide benefits over other oxygen delivery methods given their high oxygen loading capability (i.e. >70% v/v). The ultrasound contrast augmentation of LOMs yielded directionality and real-time monitoring for oxygen delivery. However, LOMs fail to move through the endothelial gaps (i.e., 400-800 nm) of the vasculature in carcinoma for extravasation due to the large diameter (typically 1 to 2 μm 28); therefore they have to depend on external stimuli (e.g., ultrasound) to trigger the discharge of oxygen in the vasculature and the distribution of discharged oxygen into carcinoma. Similar to other oxygen delivery systems, LOMs may also confront the early release of oxygen in the circulatory blood before entering the target sites due to the gas diffusion over the lipid shells of LOMs.

Accordingly, there is a need for a safe and effective treatment for medical emergencies such as retina hypoxia.

SUMMARY

This disclosure provides a unique class of perfluorocarbon-free dextran-based oxygen nanobubbles (DONBs) formulation. The critical components in the formulation are chosen among the U.S. Food, and Drug Administration's (FDA) approved compounds, which provide a biocompatible environment for incorporating pharmaceutical agents. Moreover, the nanobubbles are fabricated with simple sonication and homogenization method that easily fulfills the current good manufacturing practices (cGMP) requirements, facilitating facile scale-up of production. The formulated DONBs has the potential to release oxygen over 2 hours to maintain the partial pressure of oxygen within the inner retina high enough for 2-3 hours to preserve retinal tissue from ischemia. Thus, a safe, nanobubble formulation that mitigates retinal hypoxia has been developed.

Accordingly, this disclosure provides a composition comprising:

polysaccharide nanobubbles wherein the nanobubbles comprise a self-assembled colloidal shell that encapsulates an interior cargo;

the shell comprising dextran, trehalose, lecithin, palmitic acid, and tocopherol; and an electrolyte;

wherein the nanobubbles have an average diameter of about 200 nm or more and the composition has a zeta potential less than 0 mV.

This disclosure also provides a method for treating ocular ischemia comprising:

administering to the interior of an ischemic eye of a subject in need of therapy for ocular ischemia an effective dose of the composition disclosed herein;

wherein the composition comprises a plurality of nanobubbles containing an interior cargo of oxygen gas; and the nanobubbles disintegrate after administration to release the oxygen, thereby treating ocular ischemia in the subject.

The invention provides for the use of the compositions described herein for use in medical therapy. The medical therapy can be treating disorders of the eye, for example, ocular ischemia or retina hypoxia. The invention also provides for the use of a composition as described herein for the manufacture of a medicament to treat a disease in a mammal, for example, eye disease. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
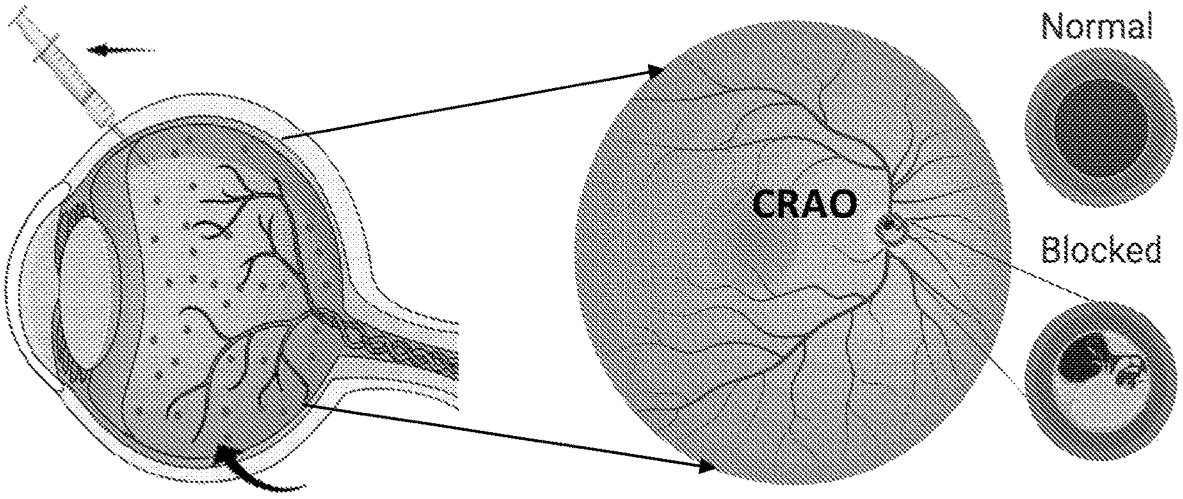
FIG. 1. The scheme of intravitreal administration of dextran encapsulated oxygen nanobubbles to supply oxygen to retinal cells and also the underlying functional mechanisms in central retinal artery occlusion.

A continuous supply of oxygen to the retina is vital to maintain its integrity and function. Lack of oxygen due to central retinal artery occlusion (CRAO) affected the retinal cells particularly retinal ganglion cells which can ultimately cause blindness if the hypoxia due to artery occlusion is not managed within 8 hours the person may blind forever. To treat this disease, we fabricate polysaccharide-based intravitreal delivery of oxygen nanobubbles system that has the potential to be an effective targeted therapy compared to the existing hyperbaric treatment, which is not effective. In this report, we describe the fabrication of dextran-based intravitreal oxygen delivery nanobubbles (DONBs). The DONBs are thin-walled, hollow polymer nanocapsules with tunable nanoporous shells. We show that DONBs are easily charged with oxygen gas and are tuned to release their oxygen payload only when exposed to physiological conditions. The size distribution and concentration of the final optimized formulation used in all of the in vitro and in vivo studies was 218.71±51.05 nm. The ζpotential of the final optimized formulation was −58.8±1.3 mV. We demonstrate that oxygen release from DONBs is sustained they deliver oxygen in simulated aqueous/vitreous humor and porcine serum for 2 hours. The stability studies revealed that DONBs are stable in the amber and clear vial container at 5° C.±3° C. for 4.52 and 4.26 months. The excipients concentration-based toxicity studies revealed that there is no significant toxicity found as compared to the control group. The cell viability studies show that DONBs have a significant effect on the survival of the R-28 cell line after hypoxia up to 12 hours however cell viability studies show that there is no significant effect of hypoxia was observed in the case ARPE-19 cell line this is because of this cell line is more stable towards hypoxia as compared to R-28 cell line. The in-vivo hypoxia model results revealed that 5 μl of DONBs recover hypoxia induced by our hypoxia model and intraocular pressure return to normal within 6 hours which is helpful for the next dose if needed. The histology studies show almost full recovery of ganglion cells in the ganglion cell layer and the thickness was also maintained with DONBs treatment. Together these results indicate that the efficacy of our DONBs formulation is perfect both for in-vitro and in-vivo studies.

The oxygen nanobubbles (ONBs) described herein is a composite of biocompatible materials. The ONBs are at small size diameter of around 100 nm to 200 nm, which is more suitable for treatment of eye diseases as compared to larger ONBs. Compared with the other lipid multilayer shell-based oxygen-containing nanostructures, our ONBs with dextran based multifunctional shells, formulated for treatment of eye diseases, provide the capability for long-period oxygen release into a medium and long-time storage of oxygen when the ONBs are stored.

Additional information and data supporting the invention can be found in the following publication by the inventors: ACS Applied Nano Materials 2021, 4, 6583-6593 and its Supporting Information, which is incorporated herein by reference in its entirety.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14$^{th}$ Edition, by R.J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "numberl" to "number2", implies a continuous range of numbers that includes the whole numbers and fractional numbers. For example, 1 to 10 means 1, 2, 3, 4, 5, . . . 9, 10.

It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

The volume of an oxygen nanobubble (ONB) can be estimated from the radius (i.e., ½ the diameter) of the ONB and the mathematical expression $V=4/3\ \pi r^3$ where r is the radius of the ONB.

Embodiments of the Invention

This disclosure provides composition comprising:

- polysaccharide nanobubbles wherein the nanobubbles comprise a self-assembled colloidal shell that encapsulates an interior cargo;
- the shell comprising dextran, trehalose, lecithin, palmitic acid, and tocopherol; and
- an electrolyte or salt;
- wherein the nanobubbles have an average diameter of about 200 nm or more and the composition has a zeta potential less than 0 mV.

In some embodiments the phospholipid is a phosphatidylcholine or glycerophospholipid. In some embodiments the phospholipid is an emulsifier such as lecithin (e.g., Epikuron 170™). In other embodiments the fatty acid is a saturated fatty acid. In other embodiments the fatty acid is a $C_{16}$-fatty acid or $(C_{12}$-$C_{20})$fatty acid. In some embodiments the antioxidant is a fat-soluble antioxidant. In some embodiments the antioxidant comprises a chromane ring or a hydroxy substituted chromane ring. In some embodiments, the shell comprises a hollow interior, hollow core, or voided interior, wherein said interior or core is optionally filled with a cargo.

In various embodiments, the composition comprises about $2\times10^{-2}$ wt % to about $20\times10^{-2}$ wt % dextran. In various embodiments, the composition comprises about $0.5\times10^{-2}$ wt % to about $10\times10^{-2}$ wt % trehalose. In various embodiments, the composition comprises about $0.1\times10^{-2}$ wt % to about $10\times10^{-2}$ wt % lecithin. In various embodiments, the composition comprises about $0.5\times10^{-3}$ wt % to about $12\times10^{-3}$ wt % palmitic acid. In various embodiments, the composition comprises about $1\times10^{-4}$ wt % to about $40\times10^{-4}$ wt % tocopherol (TPGS). In various embodiments, the composition comprises about $1\times10^{-4}$ wt % to about $25\times10^{-4}$ wt % potassium chloride.

In various embodiments, the composition comprises about $2\times10^{-2}$ wt % to about $10\times10^{-2}$ wt % dextran. In various embodiments, the composition comprises about $0.5\times10^{-2}$ wt % to about $5\times10^{-2}$ wt % trehalose. In various embodiments, the composition comprises about $0.5\times10^{-2}$ wt % to about $5\times10^{-2}$ wt % lecithin. In various embodiments, the composition comprises about $1\times10^{-3}$ wt % to about $10\times10^{-3}$ wt % palmitic acid. In various embodiments, the composition comprises about $3\times10^{-4}$ wt % to about $30\times10^{-4}$ wt % tocopherol (TPGS). In various embodiments, the composition comprises about $2\times10^{-4}$ wt % to about $20\times10^{-4}$ wt % potassium chloride.

In various embodiments, the composition comprises about $5\times10^{-2}$ wt % to about $8\times10^{-2}$ wt % dextran. In various embodiments, the composition comprises about $0.5\times10^{-2}$ wt % to about $2.5\times10^{-2}$ wt % trehalose. In various embodiments, the composition comprises about $0.5\times10^{-2}$ wt % to about $2\times10^{-2}$ wt % lecithin. In various embodiments, the composition comprises about $3.5\times10^{-3}$ wt % to about $6\times10^{-3}$ wt % palmitic acid. In various embodiments, the composition comprises about $7\times10^{-4}$ wt % to about $10\times10^{-4}$ wt % tocopherol (TPGS). In various embodiments, the composition comprises about $5.5\times10^{-4}$ wt % to about $8.5\times10^{-4}$ wt % potassium chloride.

In some embodiments, the composition comprises about $6.98\times10^{-2}$ wt % dextran, about $1.24\times10^{-2}$ wt % trehalose, about $1.07\times10^{-2}$ wt % lecithin, about $4.42\times10^{-3}$ wt % palmitic acid, about $8.68\times10^{-4}$ wt % tocopherol (TPGS). In other embodiments, the composition comprises about $6.98\times10^{-4}$ wt % potassium chloride.

Also, this disclosure provides a polysaccharide nanobubble comprising:

- a self-assembled colloidal shell that encapsulates an interior cargo;
- the shell comprising dextran, trehalose, lecithin, palmitic acid, and tocopherol;
- wherein the nanobubble has a diameter less than about 250 nm, about 200 nm to about 250 nm, or about 200 nm. to about 250 nm.

In some embodiments, the polysaccharide nanobubble is a filtered or isolated polysaccharide nanobubble.

In various embodiments, the shell comprises about $2\times10^{-2}$ wt % to about $20\times10^{-2}$ wt % dextran. In various embodiments, the shell comprises about $0.5\times10^{-2}$ wt % to about $10\times10^{-2}$ wt % trehalose. In various embodiments, the shell comprises about $0.1\times10^{-2}$ wt % to about $10\times10^{-2}$ wt % lecithin. In various embodiments, the shell comprises about $0.5\times10^{-3}$ wt % to about $12\times10^{-3}$ wt % palmitic acid. In various embodiments, the shell comprises about $1\times10^{-4}$ wt % to about $40\times10^{-4}$ wt % tocopherol (TPGS). In various embodiments, the shell comprises about $1\times10^{-4}$ wt % to about $25\times10^{-4}$ wt % potassium chloride.

In various embodiments, the shell comprises about $2\times10^{-2}$ wt % to about $10\times10^{-2}$ wt % dextran. In various embodiments, the shell comprises about $0.5\times10^{-2}$ wt % to about $5\times10^{-2}$ wt % trehalose. In various embodiments, the shell comprises about $0.5\times10^{-2}$ wt % to about $5\times10^{-2}$ wt % lecithin. In various embodiments, the shell comprises about $1\times10^{-3}$ wt % to about $10\times10^{-3}$ wt % palmitic acid. In various embodiments, the shell comprises about $3\times10^{-4}$ wt % to about $30\times10^{-4}$ wt % tocopherol (TPGS). In various embodiments, the shell comprises about $2\times10^{-4}$ wt % to about $20\times10^{-4}$ wt % potassium chloride.

In various embodiments, the shell comprises about $5\times10^{-2}$ wt % to about $8\times10^{-2}$ wt % dextran. In various embodiments, the shell comprises about $0.5\times10^{-2}$ wt % to about $2.5\times10^{-2}$ wt % trehalose. In various embodiments, the shell comprises about $0.5\times10^{-2}$ wt % to about $2\times10^{-2}$ wt % lecithin. In various embodiments, the shell comprises about $3.5\times10^{-3}$ wt % to about $6\times10^{-3}$ wt % palmitic acid. In various embodiments, the shell comprises about $7\times10^{-4}$ wt % to about $10\times10^{-4}$ wt % tocopherol (TPGS). In various embodiments, the shell comprises about $5.5\times10^{-4}$ wt % to about $8.5\times10^{-4}$ wt % potassium chloride.

In some embodiments, the shell comprises about $6.98\times10^{-2}$ wt % dextran, about $1.24\times10^{-2}$ wt % trehalose, about $1.07\times10^{-2}$ wt % lecithin, about $4.42\times10^{-3}$ wt % palmitic acid, about $8.68\times10^{-4}$ wt % tocopherol (TPGS). In other embodiments, the shell comprises about $6.98\times10^{-4}$ wt % potassium chloride.

In various embodiments, the nanobubbles are perfluorocarbon-free. In some embodiments, the nanobubble further comprises an electrolyte. In some embodiments, the nanobubbles have an average diameter of about 200 nm or more, preferably about 165 nm to about 270 nm. In some embodiments, the zeta potential less than 0 mV. In some embodiments, the electrolyte is in a suspension of ONB's that has a pH less than 7, or a pH more than 7. In various embodiments, the cargo is oxygen ($O_2$). In other embodiments, the cargo is a gas. In various other embodiments, dextran has an average molecular weight of about 200 kDa. In other embodiments, dextran has an average molecular weight of about 100 kDa to about 300 kDa. In other embodiments, lecithin is a soy or canola lecithin. In other embodiments, tocopherol is alpha-tocopherol.

In other embodiments, the electrolyte is in a solution or electrolyte mixture that comprises a mineral salt or phosphate salt. In other embodiments, the mineral salt is potassium chloride, sodium chloride, or lithium chloride. In various embodiments, the diameter is about 100 nm to about 300 nm, about 165 nm to about 270 nm, about 150 nm to about 250 nm, about 150 nm to about 250 nm, about 120 nm to about 130 nm, about 225 nm to about 215 nm, about 220 nm, about 219 nm, or about 218 nm. In various embodiments, the variance in diameter is ±75 nm or less, ±60 nm, ±50 nm, or ±25 nm.

In other embodiments, the zeta potential is about −75 mV to about −50 mV, about −65 mV to about −55 mV, about −35 mV to about −25 mV, about −60 mV, or about −59 mV. In other embodiments, the variance in zeta potential is ±10 mV or less, ±5 mV, ±3 mV, ±2 mV, or ±1 mV. In other embodiments, the pH is about 5.5 to about 5.75. In other embodiments, the pH is less than about 9, less than about 8, less than about 6, less than about 5, less than about 4, less than about 3, or about 4 to about 8.

In other embodiments, the sample has about $6.98\times10^{-2}$ wt % dextran, about $1.24\times10^{-2}$ wt % trehalose, about $1.07\times10^{-2}$ wt % lecithin, about $4.42\times10^{-3}$ wt % palmitic acid, about $8.68\times10^{-4}$ wt % tocopherol (TPGS), and the electrolyte comprises about $6.98\times10^{-4}$ wt % potassium chloride.

Additionally, this disclosure provides a method for treating ocular ischemia comprising:

administering to the interior of an ischemic eye of a subject in need of therapy for ocular ischemia an effective dose of the composition disclosed herein;

wherein the composition comprises a plurality of nanobubbles containing an interior cargo of oxygen gas; and the nanobubbles disintegrate after administration to release the oxygen, thereby treating ocular ischemia in the subject.

In various embodiments, the nanobubbles are filtered. In various embodiments, the composition comprises filtered nanobubbles. In various embodiments, the filtered nanobubbles are mixed with a buffer. In various embodiments, the nanobubbles comprise a buffer. In some other embodiments, the amount of oxygen released is at least 500 nanoliters per microliter of the composition per minute. In some other embodiments, the amount of oxygen released per microliter of the composition per minute is about 400 nanoliters, about 600 nanoliters, about 800 nanoliters, about 1000 nanoliters, or about 1500 nanoliters.

In other embodiments, the effective dose is at least 5 microliters of the composition. In other embodiments, the effective dose of the composition is about 1 microliter to about 100 microliters, about 10 microliters, about 20 microliters, or about 50 microliters. In other embodiments, treatment comprises more than one effective dose. In other embodiments, the ocular ischemia is retina hypoxia. In additional embodiments, the disclosed oxygen nanobubbles can treat other known eye diseases, or other ischemic conditions of the eye, such as branch retinal vein occlusion, branch retinal artery occlusion, diabetic retinopathy, central retinal vein occlusion, central retinal artery occlusion (CRAO), ischemic optic neuropathy, ocular ischemic syndrome, age related macular degeneration and similar diseases.

Furthermore, this disclosure provides a method for forming a composition of oxygen containing nanobubbles comprising oxygenating an aqueous mixture of dextran, trehalose, lecithin, palmitic acid, tocopherol; and an electrolyte, thereby forming the oxygen containing nanobubbles (ONB's). In various embodiments, the mixture is sonicated during oxygenation. In other embodiments the ONB's are isolated by filtration.

In various embodiments, the mixture comprises about $2\times10^{-2}$ wt % to about $20\times10^{-2}$ wt % dextran. In various embodiments, the mixture comprises about $0.5\times10^{-2}$ wt % to about $10\times10^{-2}$ wt % trehalose. In various embodiments, the mixture comprises about $0.1\times10^{-2}$ wt % to about $10\times10^{-2}$ wt % lecithin. In various embodiments, the mixture comprises about $0.5\times10^{-3}$ wt % to about $12\times10^{-3}$ wt % palmitic acid. In various embodiments, the mixture comprises about $1\times10^{-4}$ wt % to about $40\times10^{-4}$ wt % tocopherol (TPGS). In various embodiments, the mixture comprises about $1\times10^{-4}$ wt % to about $25\times10^{-4}$ wt % potassium chloride.

In various embodiments, the mixture comprises about $2\times10^{-2}$ wt % to about $10\times10^{-2}$ wt % dextran. In various embodiments, the mixture comprises about $0.5\times10^{-2}$ wt % to about $5\times10^{-2}$ wt % trehalose. In various embodiments, the mixture comprises about $0.5\times10^{-2}$ wt % to about $5\times10^{-2}$ wt % lecithin. In various embodiments, the mixture comprises about $1\times10^{-3}$ wt % to about $10\times10^{-3}$ wt % palmitic acid. In various embodiments, the mixture comprises about $3\times10^{-4}$ wt % to about $30\times10^{-4}$ wt % tocopherol (TPGS). In various embodiments, the mixture comprises about $2\times10^{-4}$ wt % to about $20\times10^{-4}$ wt % potassium chloride.

In various embodiments, the mixture comprises about $5\times10^{-2}$ wt % to about $8\times10^{-2}$ wt % dextran. In various embodiments, the mixture comprises about $0.5\times10^{-2}$ wt % to about $2.5\times10^{-2}$ wt % trehalose. In various embodiments, the mixture comprises about $0.5\times10^{-2}$ wt % to about $2\times10^{-2}$ wt % lecithin. In various embodiments, the mixture comprises about $3.5\times10^{-3}$ wt % to about $6\times10^{-3}$ wt % palmitic acid. In various embodiments, the mixture comprises about $7\times10^{-4}$ wt % to about $10\times10^{-4}$ wt % tocopherol (TPGS). In various embodiments, the mixture comprises about $5.5\times10^{-4}$ wt % to about $8.5\times10^{-4}$ wt % potassium chloride.

In some embodiments, the mixture comprises about $6.98\times10^{-2}$ wt % dextran, about $1.24\times10^{-2}$ wt % trehalose, about $1.07\times10^{-2}$ wt % lecithin, about $4.42\times10^{-3}$ wt % palmitic acid, about $8.68\times10^{-4}$ wt % tocopherol (TPGS). In other embodiments, the mixture comprises about $6.98\times10^{-4}$ wt % potassium chloride.

In various embodiments, the composition, shell, or mixture comprises about $4\times10^{-2}$ wt % to about $9\times10^{-2}$ wt % dextran. In various embodiments, the composition, shell, or mixture comprises about $0.75\times10^{-2}$ wt % to about $2\times10^{-2}$ wt % trehalose. In various embodiments, the composition, shell, or mixture comprises about $0.5\times10^{-2}$ wt % to about $2\times10^{-2}$ wt % lecithin. In various embodiments, the composition, shell, or mixture comprises about $3\times10^{-3}$ wt % to about $7\times10^{-3}$ wt % palmitic acid. In various embodiments, the composition, shell, or mixture comprises about $6\times10^{-4}$ wt % to about $12\times10^{-4}$ wt % tocopherol (TPGS). In various embodiments, the composition, shell, or mixture comprises about $5\times10^{-4}$ wt % to about $10\times10^{-4}$ wt % potassium chloride.

All reported wt % disclosed herein are alternatively interpreted as % w/v, and vice versa. All reported % w/v disclosed herein are alternatively interpreted as wt %, and vice versa.

Results and Discussion

Here we report a perfluorocarbon-free dextran-based oxygen nanobubbles (DONBs) platform fabricated by sonication and homogenization method. The formulation was optimized using rotatable central composite design (RCCD) data analysis, experimental design, and model building was performed via software Design Expert® (Version 11.1.1.0, State-Ease, Inc., Minneapolis, MN, USA). Rotatable central composite design (RCCD), response surface methodology RSM, Box-Behnken, and Doehlert designs are among the primary response surface methodologies used in pharmaceutical engineering for formulation optimization and development. In the current formulation, a four-factored RCCD design was used to establish the functional relationships among four operating variables, i.e., dextran ($X_1$), potassium chloride ($X_2$), sonication power ($X_3$), and pH ($X_4$), and the responses are the average oxygen release ($Y_1$) at 2 hours, the size of oxygen nanobubbles (Y2), and (potential ($Y_3$). After successfully optimized thirty different formulations we select one formulation based on the best results in terms of desire response, we set for each variable.

Figure 11:
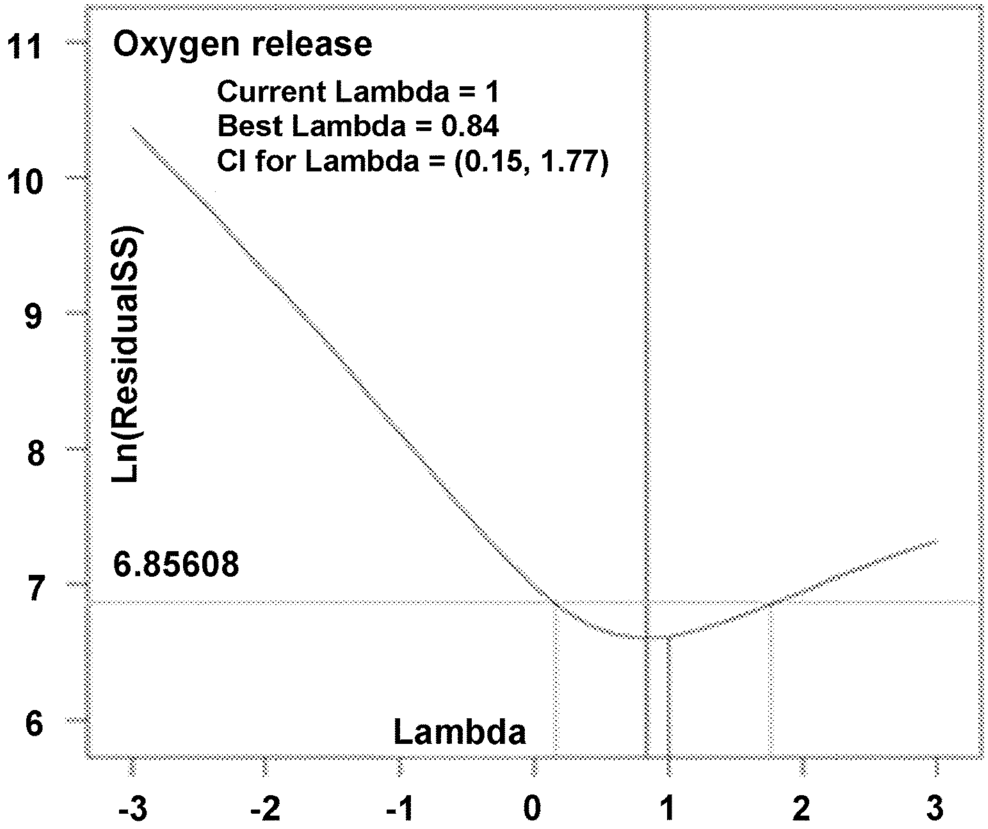
FIG. 11. Box-Cox plot for the non-transformed model.
Figure 11:
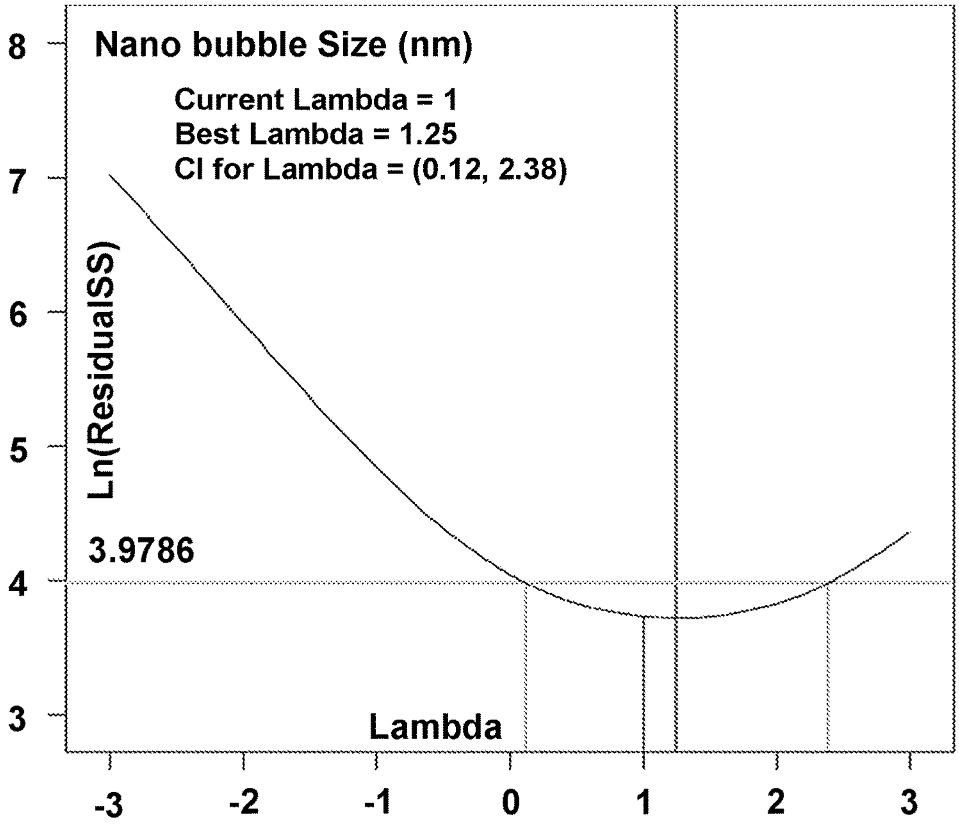
Figure 11:
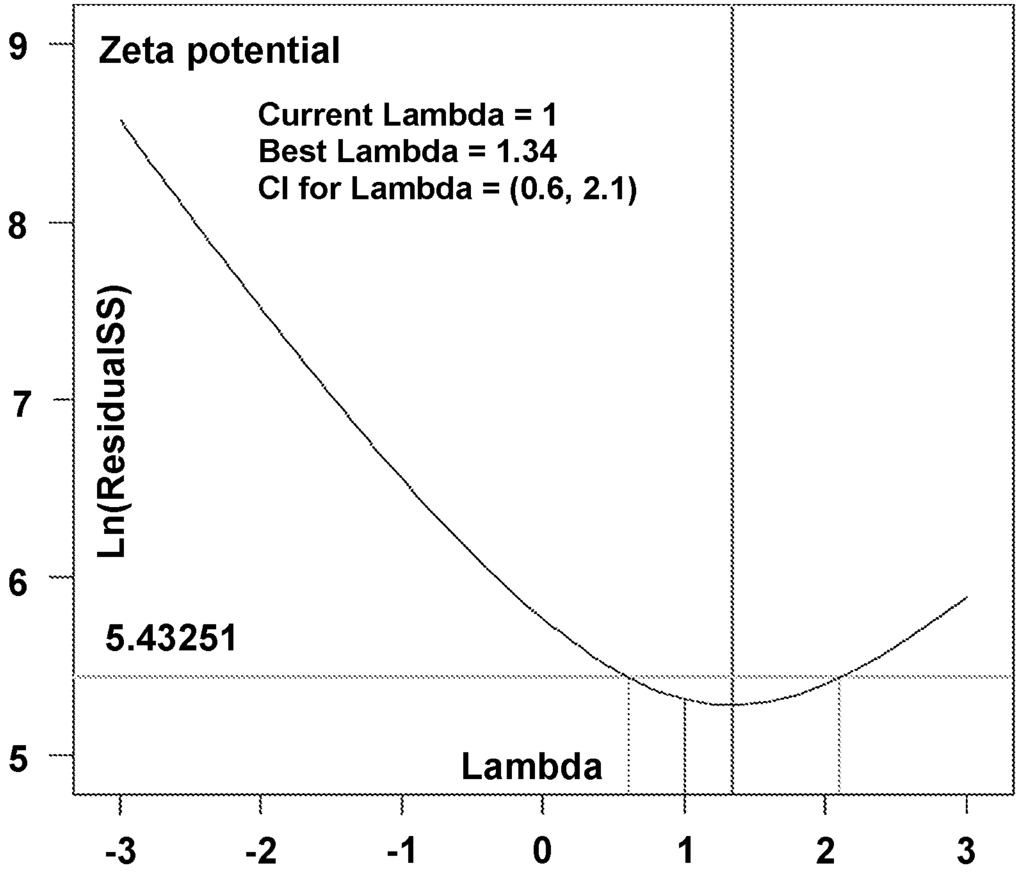

The objective of RCCD was to analyze frequent interactions to generate a mathematical association among the chosen independent parameters with the size of oxygen nanobubbles and an average oxygen release. The experiments were conducted in triplicate, and the mean values were used as the response. To validate the observed response against the predicted, mathematical optimization was implemented by setting the response to "maximum" when all parametric values were set in range. (Table 1) provides the design summary for formulation optimization. The low and high values of independent variables were set for the construction of adequate and reliable development of a mathematical model with the best experimental data fitting. Based on the input conditions, a list of thirty experimental runs was performed for the conditions proposed by the RCCD model. The Box-Cox plot for the RCCD model used in this study is discussed in the Examples and the graphical representation is shown in (FIG. 11).

Figure 2:
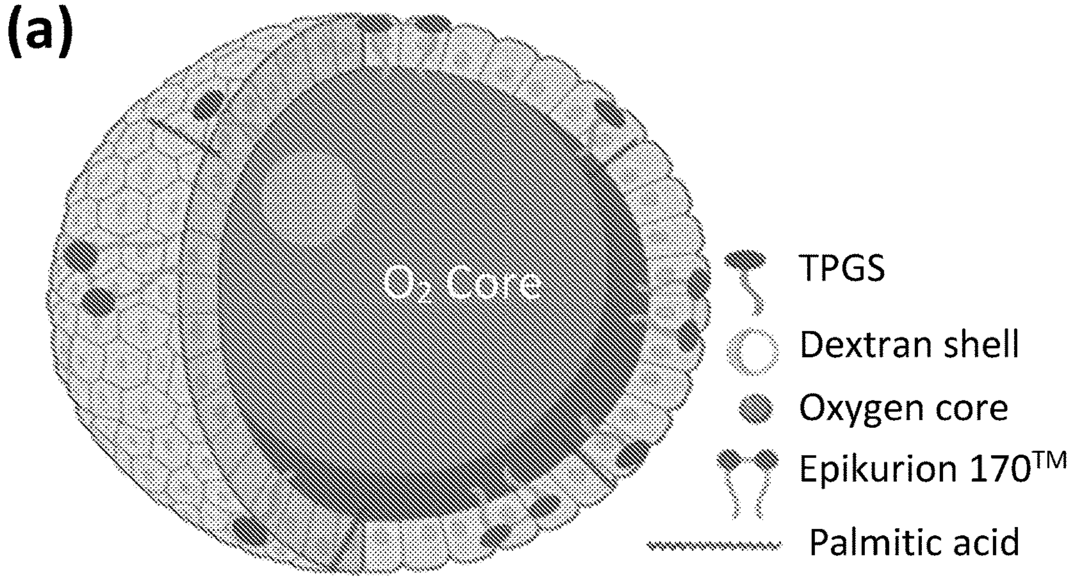
FIG. 2. Schematic of Dextran oxygen nanobubbles (DONBs) and their characterization. (a), 1 Schematic diagram of DONBs consists of dextran shells (0.818 mg dextran/mL and 0.290 mg phospholipid/ml at 4° C. to encapsulate oxygen. (b) concentration and size distribution of DONBs/ml obtained using NTA (Nano Sight NS 300). (c) Image of floating DONBs using NTA (Nano Sight NS 300). (d) zeta potential of DONBs in different pH medium. (e, f, and g) Cryo TEM of DONBs.
Figure 2:
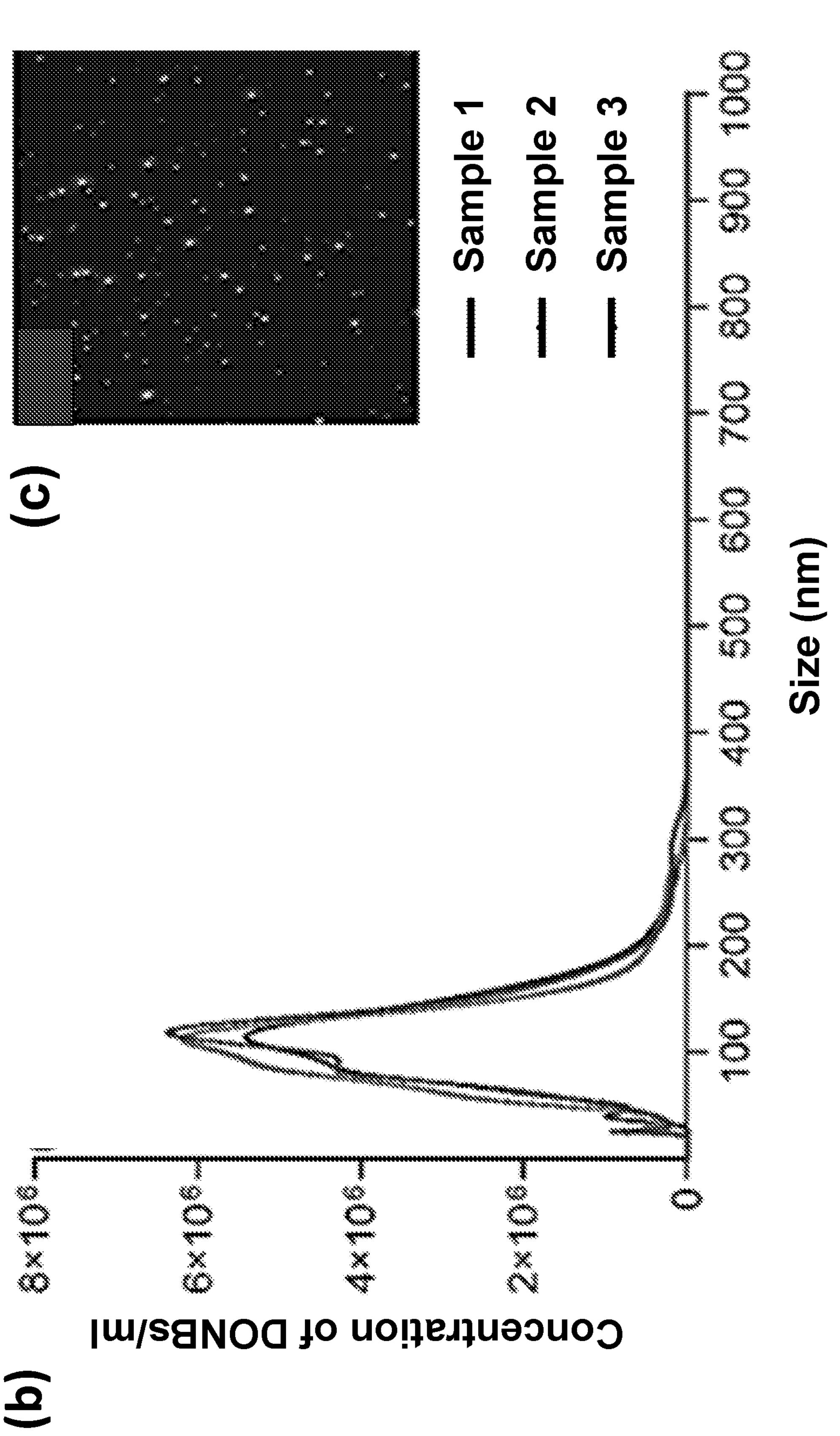
Figure 2:
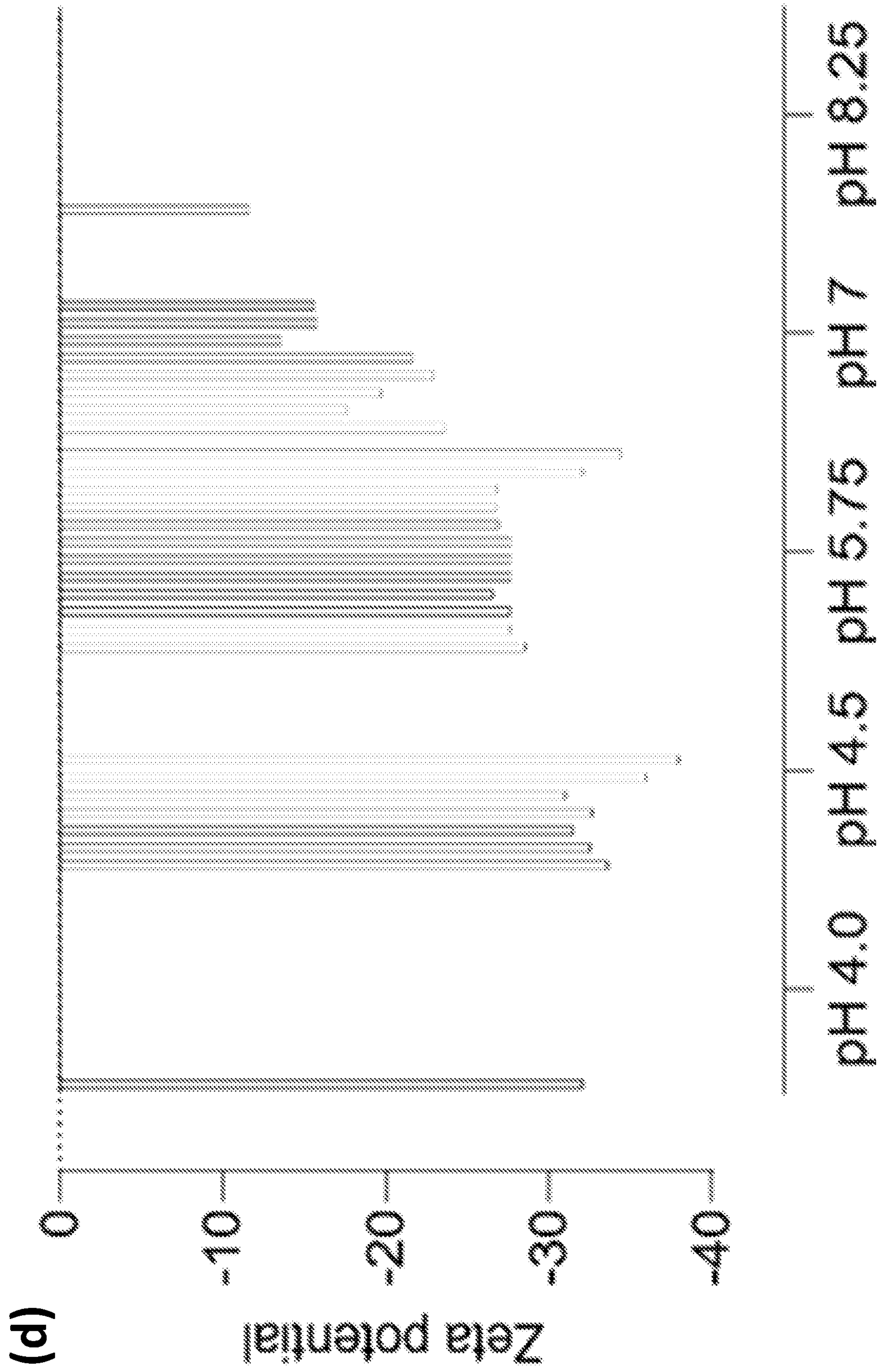
Figure 2:
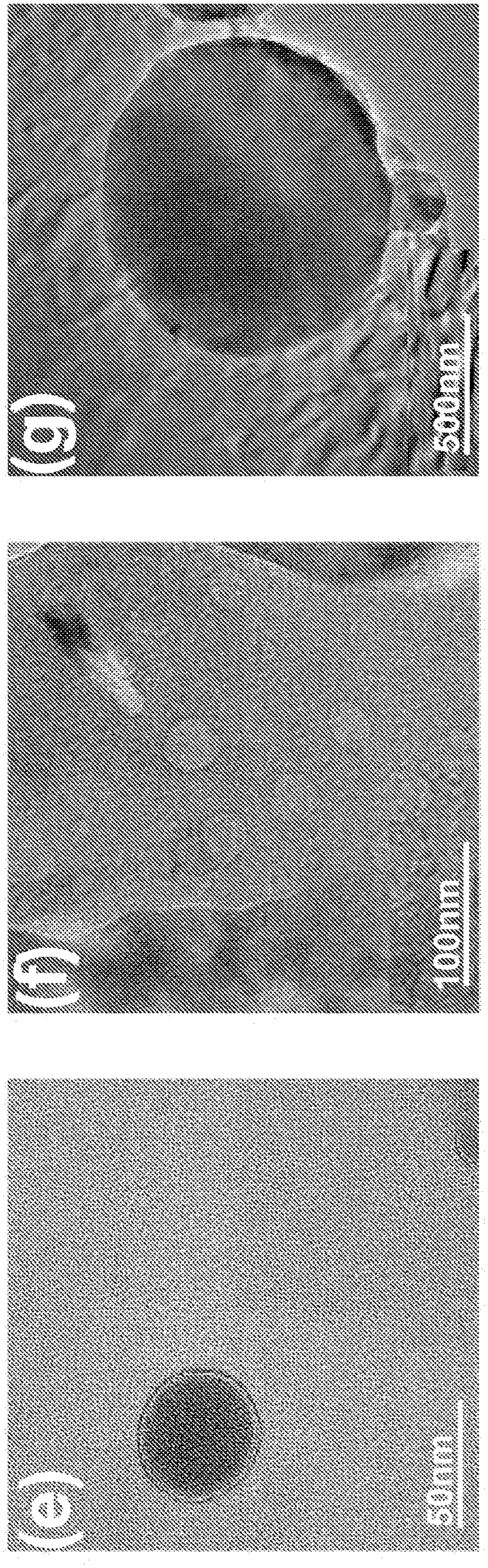
Figure 12:
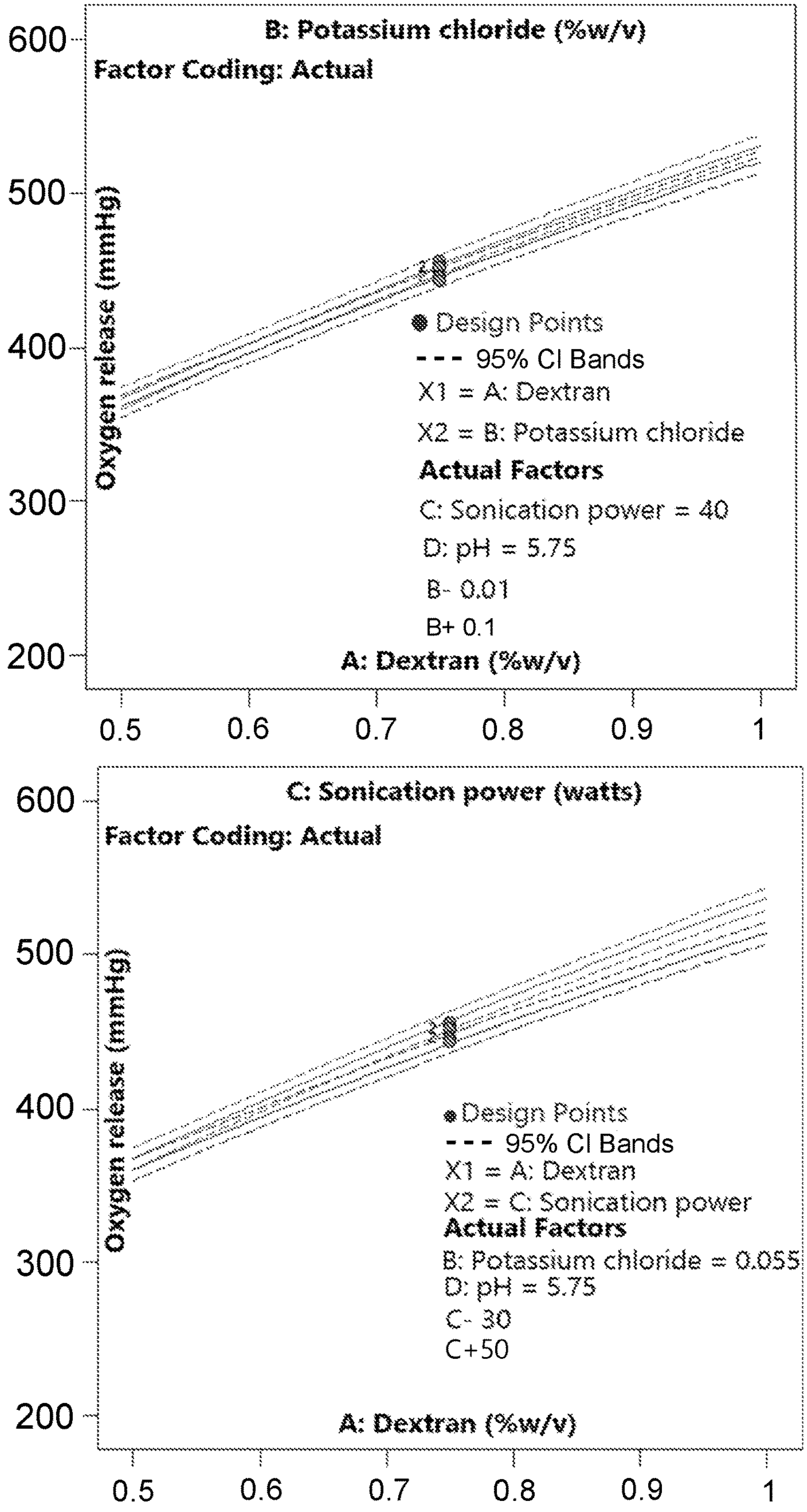
FIG. 12. Two-dimensional interaction response surface graph showing the influence of independent variable on oxygen release.
Figure 12:
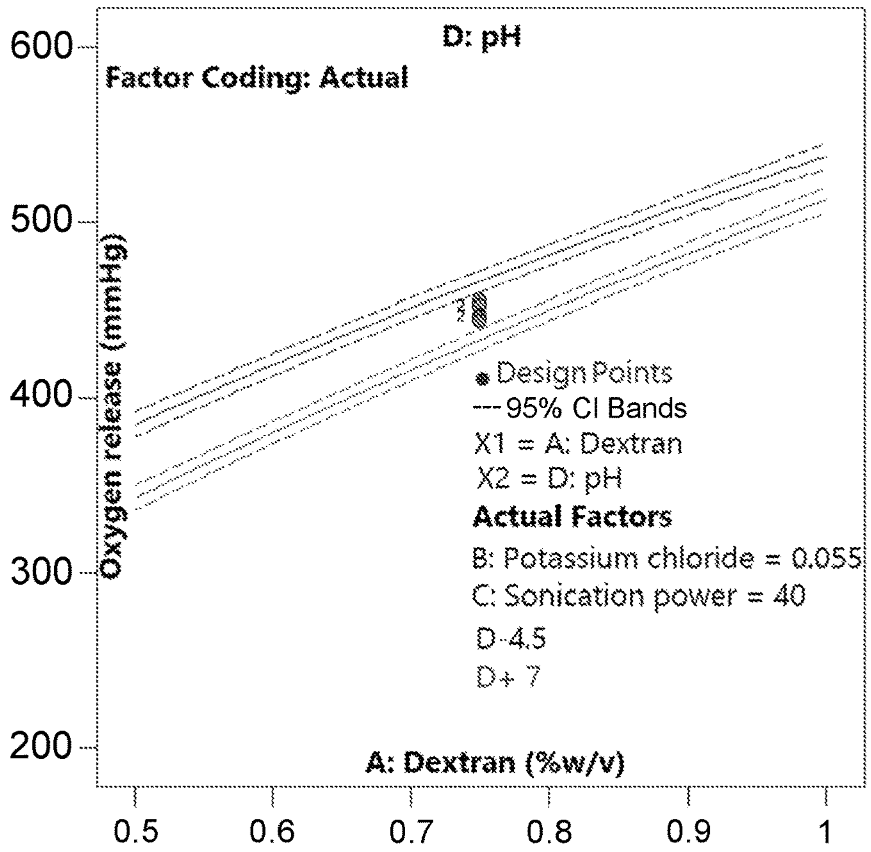
Figure 12:
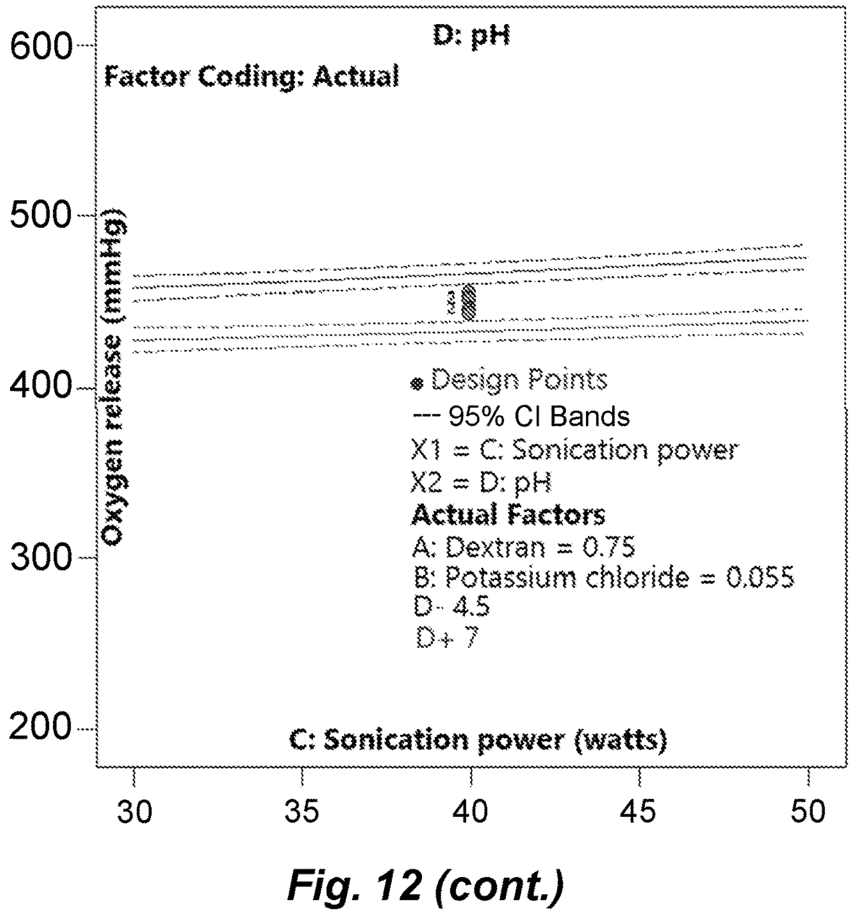
Figure 12:
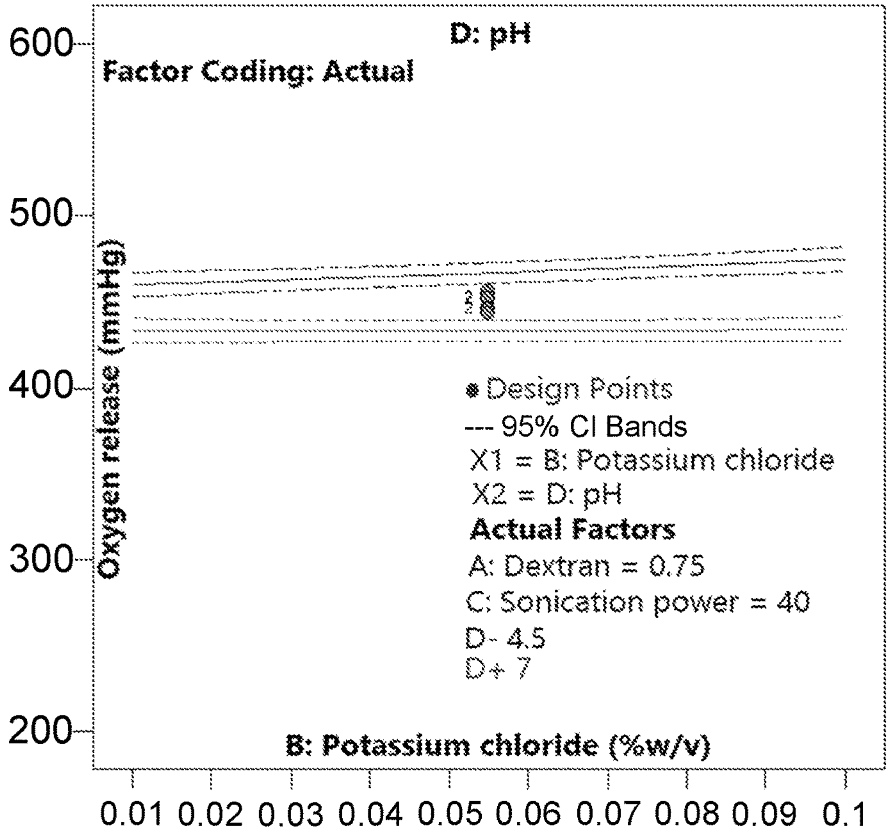
Figure 12:
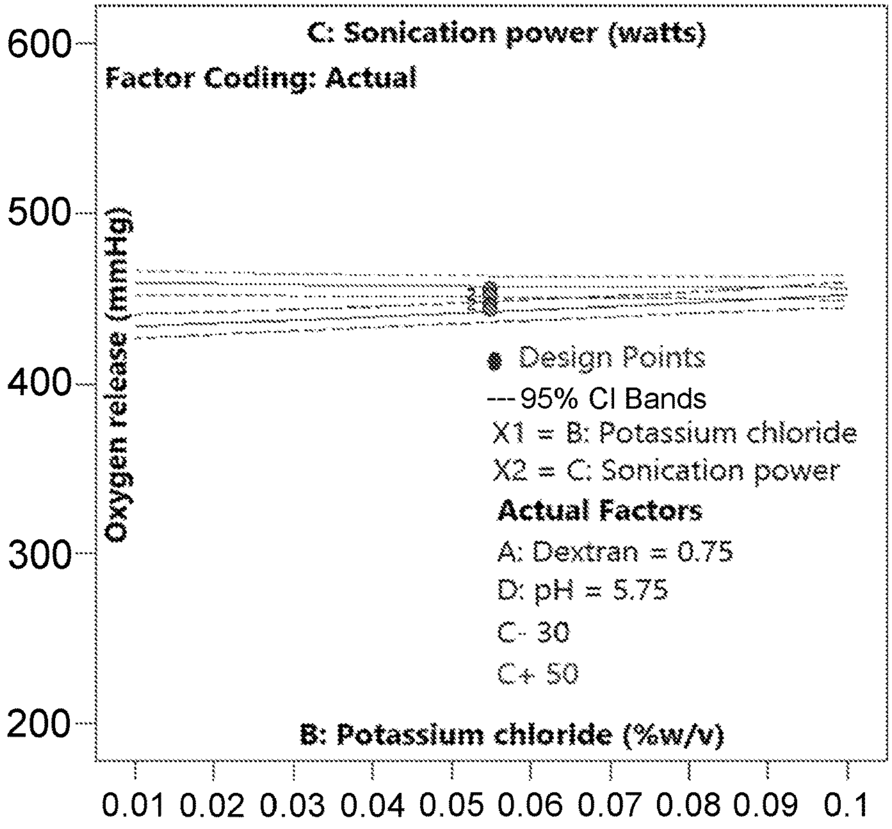
Figure 13:
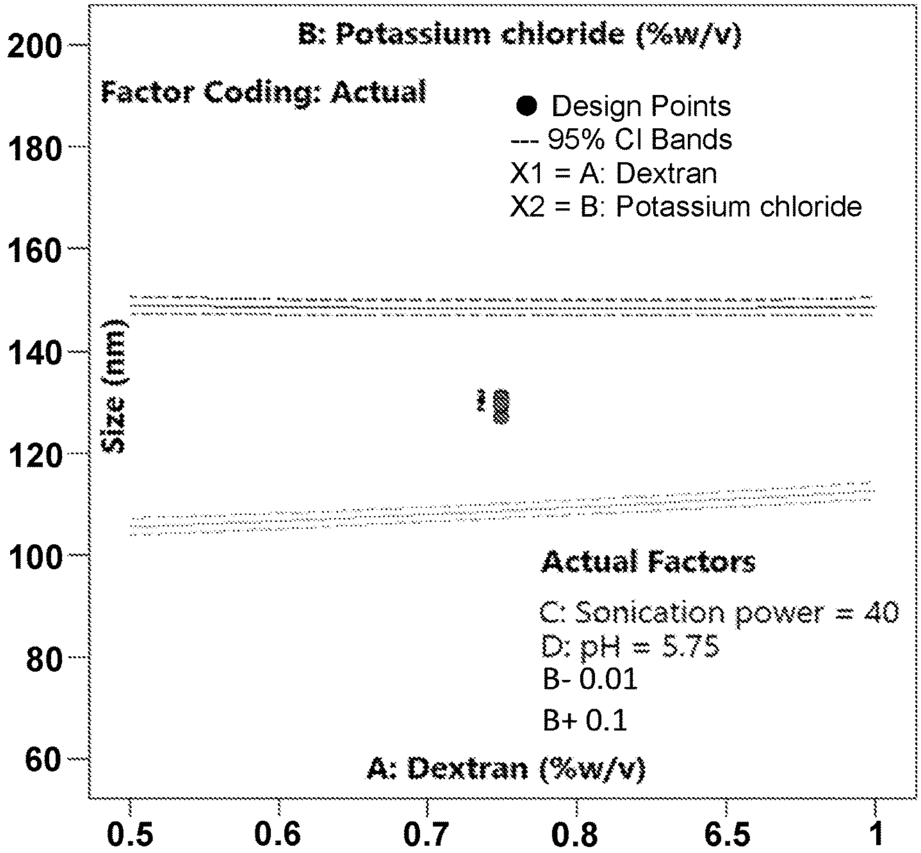
FIG. 13. Two-dimensional interaction response showing the influence of independent variables on the size of nanobubbles.
Figure 13:
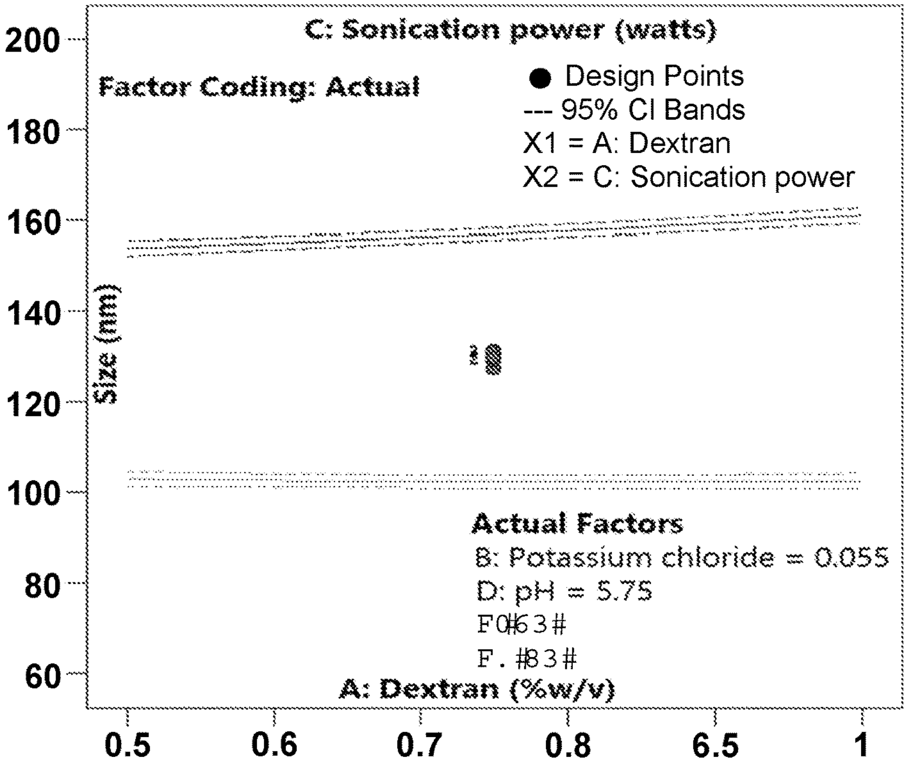
Figure 13:
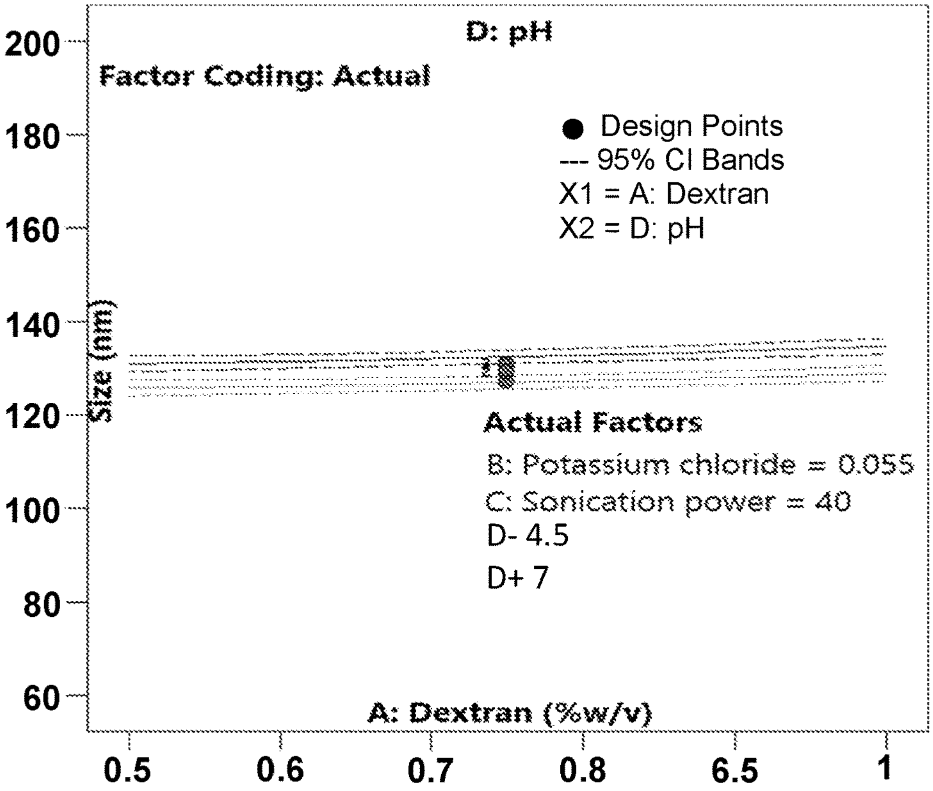
Figure 13:
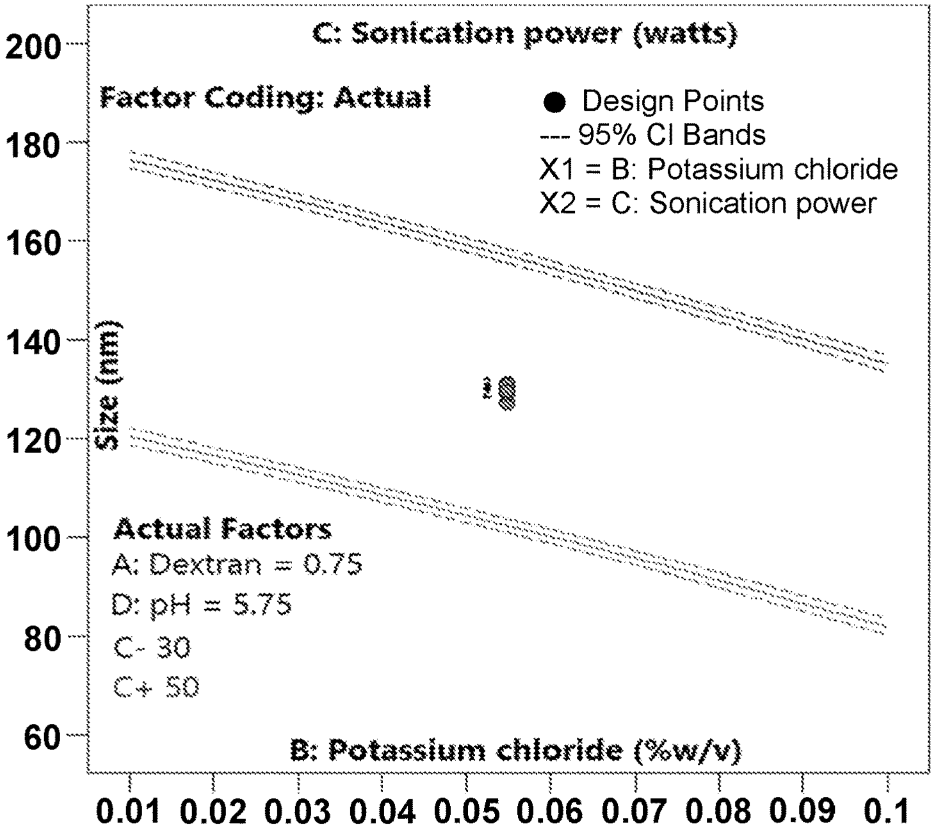
Figure 13:
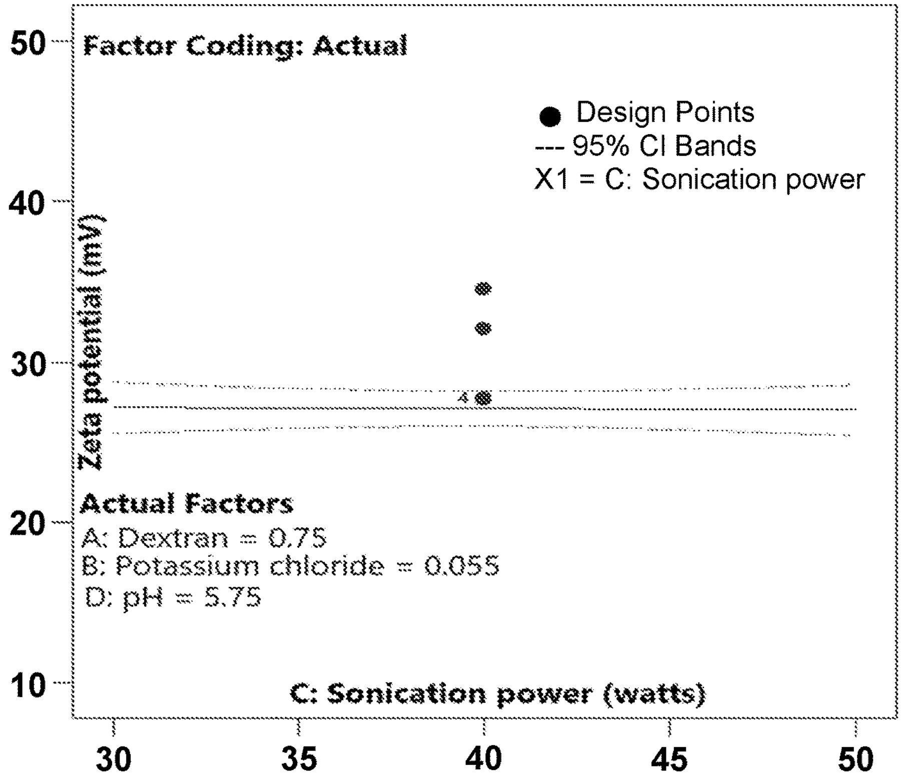
Figure 14:
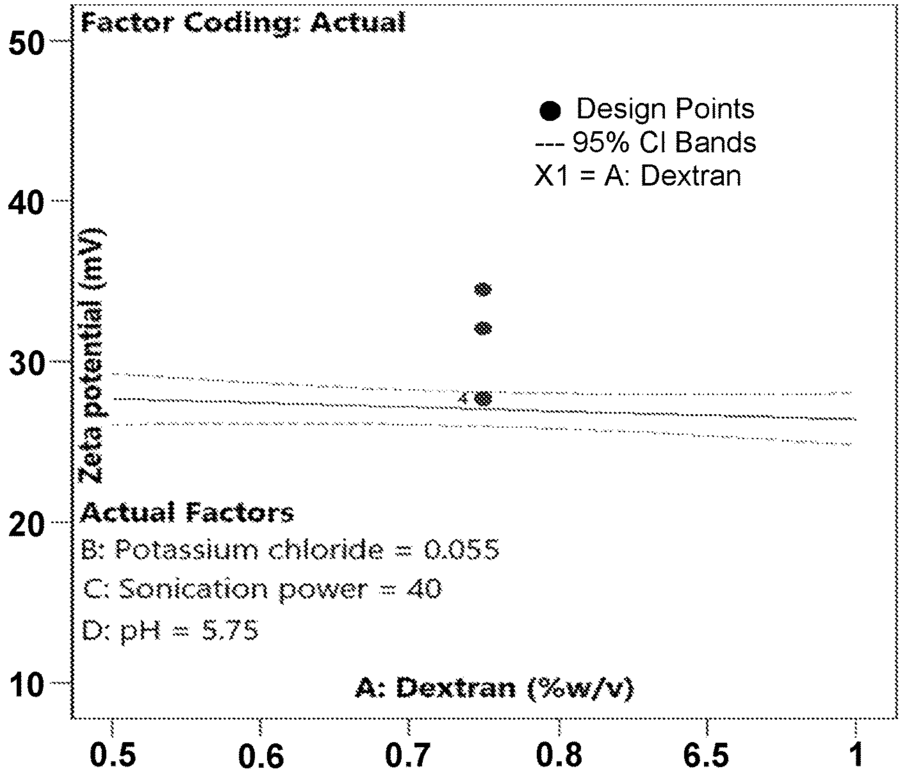
FIG. 14. Two-dimensional interaction response showing the influence of independent variables on the zeta potential of nanobubbles.
Figure 14:
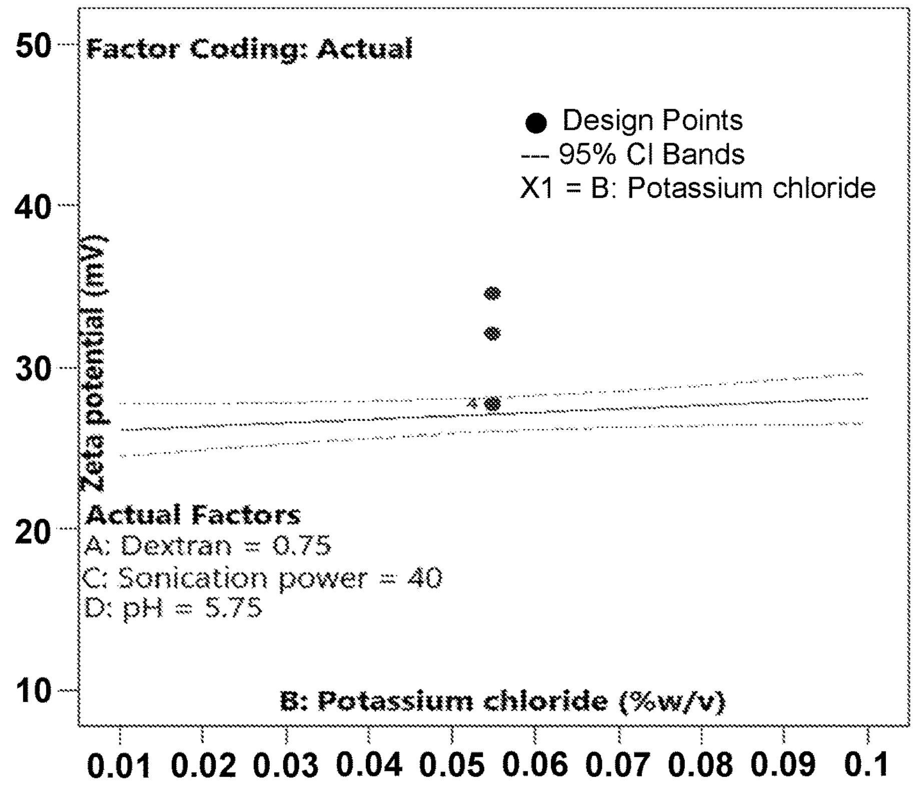
Figure 14:
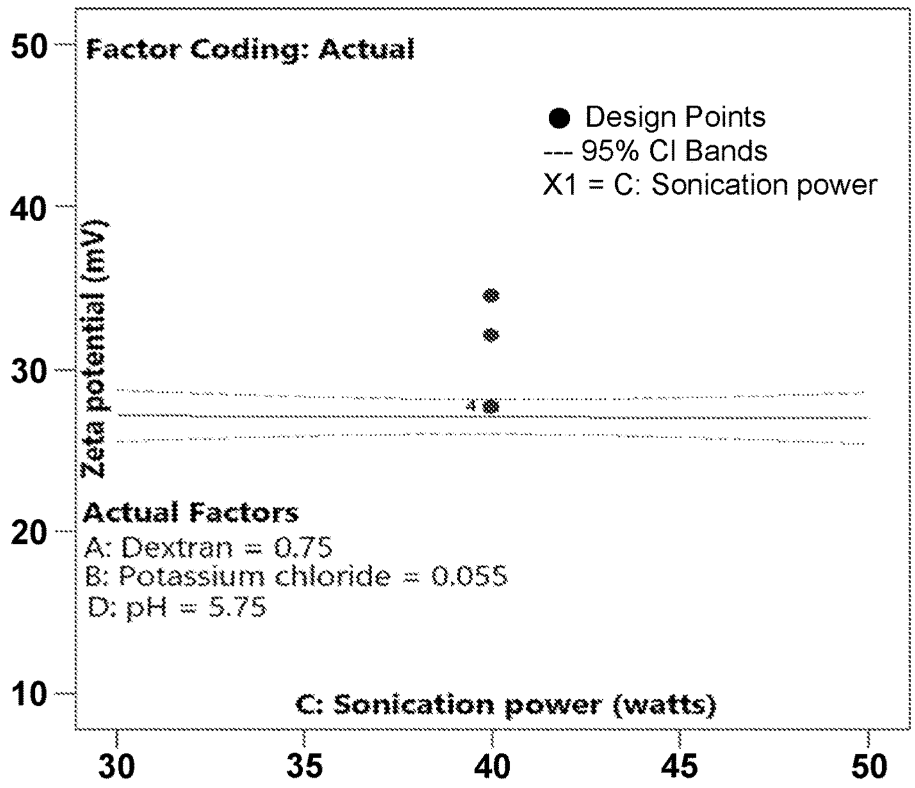
Figure 14:
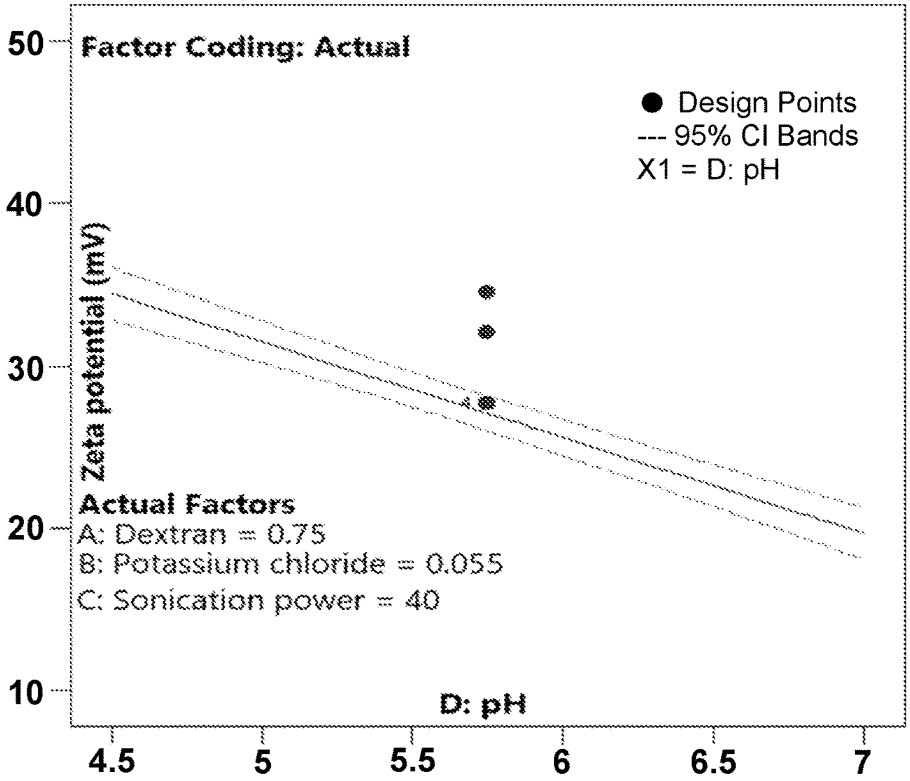

Briefly the concentration of dextran used was (0.9% w/v) and (0.23% w/v) phospholipid. The phospholipids and (0.19% w/v) palmitic acid acts as an emulsifier in the formulation. Potassium chloride is used as an electrolyte to help reduce the size of the nanobubbles during sonication and cavitation. D-a-tocopherol polyethylene glycol 1000 succinate (TPGS) reduces the surface tension of the nanobubbles and helps in the self-assembly of nanobubbles during formulation. Trehalose is used to increase the stability of the dextran core. We chose TPGS as a surfactant because it helps the nanobubbles to enter the retinal layers by inhibiting the activity of ATP-dependent P-glycoprotein and acts as a potent excipient for overcoming multi-drug resistance and prevent the efflux of nanobubbles from the retinal cells. The excipients used in this work are designated as biocompatible compounds by the FDA with a very low degree of cytotoxicity. The schematic of DONB encapsulating oxygen is shown in (FIG. 2*a*). The process involves the addition of potassium chloride into the sonicated dispersed phase of sterile water for injection at 4° C. The optimal potassium chloride (what is this amount) and sonication power were considered to minimize the nanobubble size. Details of optimization studies are presented in the Examples. Dextran sulfate sodium 200 kDa (0.7-1.0 mg) used as the core shell of nanobubble shows a direct relationship with oxygen release (FIG. 12). Potassium chloride and sonication power control the size of nanobubbles. The effect of potassium chloride as an electrolyte and sonication power on nanobubble size is described in the Examples (FIG. 13). A similar pattern of nanobubble size reduction by ultrasonic energy and frequency was investigated by Yasuda et al (Chemical Engineering Science 2019, 195, 455). The pH of the medium plays a vital role in controlling the (potential of nanobubbles the optimization is described in the Examples (FIG. 14).

The electrical dual-layer that plays a critical double role in the creation of stable nanobubbles in aqueous solutions not only provides a repulsive force to avoid inter bubble accumulation and coalescence but also decreases the surface tension at the water/gas boundary to reduce the internal pressure inside each bubble [please provide references]. This mechanism helps to improve the stability of formulation and decreases the toxicity in two-ways, first is to increase the colloidal stability and the second due to slightly acidic pH the final formulation is free from preservatives as observed by Jin et al. (Journal of Physical Chemistry B 2007, 111 (40), 11745) with similar results on the effect of pH and ionic strength on the stability of nanobubbles in aqueous solutions. The slightly acidic pH also protects from microbial growth. has the potential to reduce microbial activity.

The size distribution and concentration of DONBs/ml were measured using NTA (Nano Sight NS 300). The size distribution and concentration of the final optimized formulation used in all of the in vitro and in vivo studies was 218.71±51.05 nm. The results are presented in (FIG. 2*b*). The structure and morphology of the nanobubbles were examined by transmission electron microscopy (TEM; JEM-2100F, JEOL, Japan). The TEM image (FIG. 2*e*, f and g) shows the core-shell structure of the nanobubbles, and the size of the nanobubbles is in agreement with the size distribution measurement with NTA.

Figure 3:
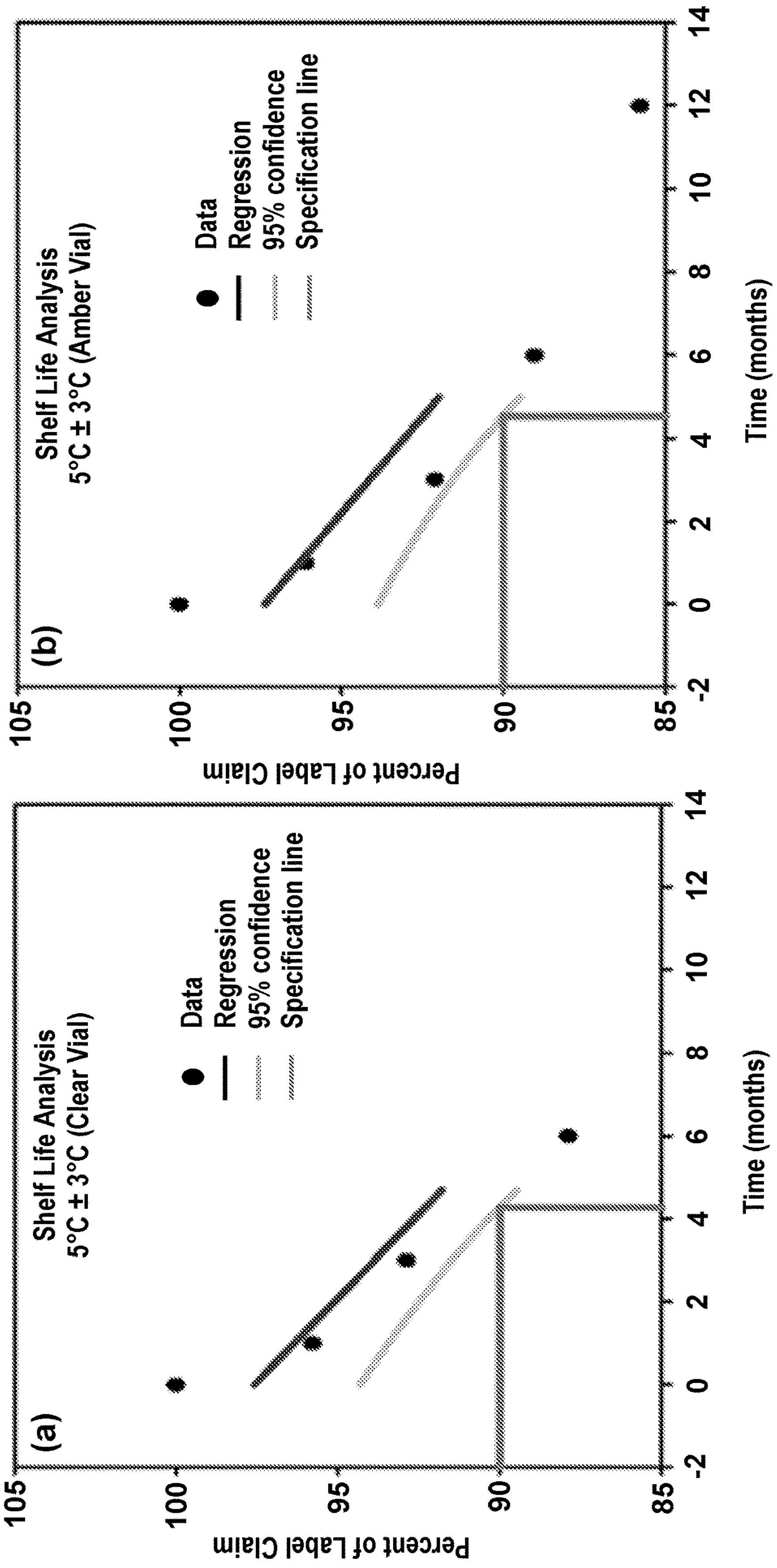
FIG. 3. Stability studies of DONBs at different temperatures and storage containers. a and b: shelf life at 5° C. in clear and amber vials. c and d: shelf life at 25° C. in the clear and amber vials and 60% relative humidity. e and f: shelf life at 30° C. in the clear vial and amber vials at 60% relative humidity. g and h: shelf life at 40° C. in the clear and amber vials at 75% relative humidity.
Figure 3:
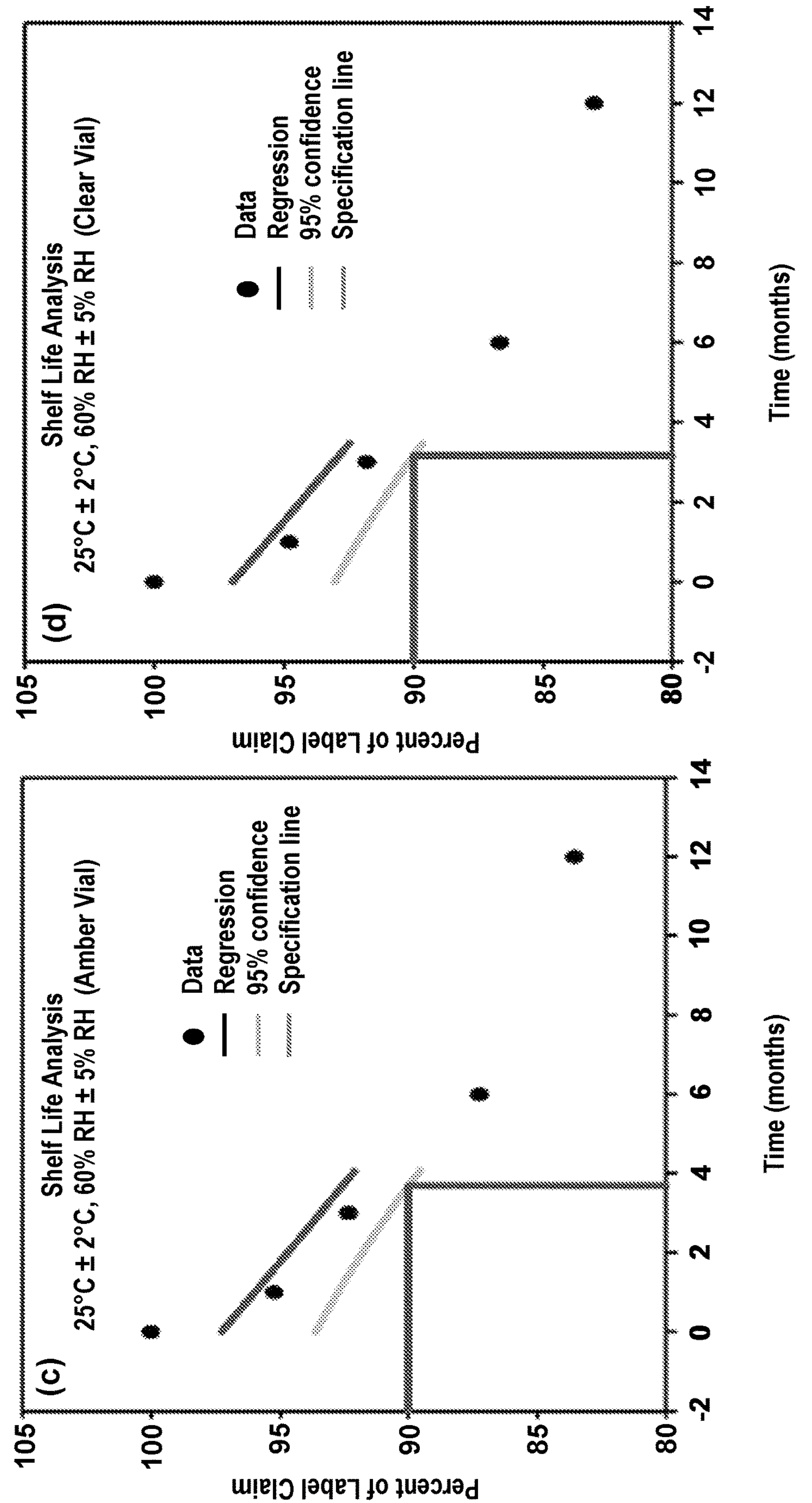
Figure 3:
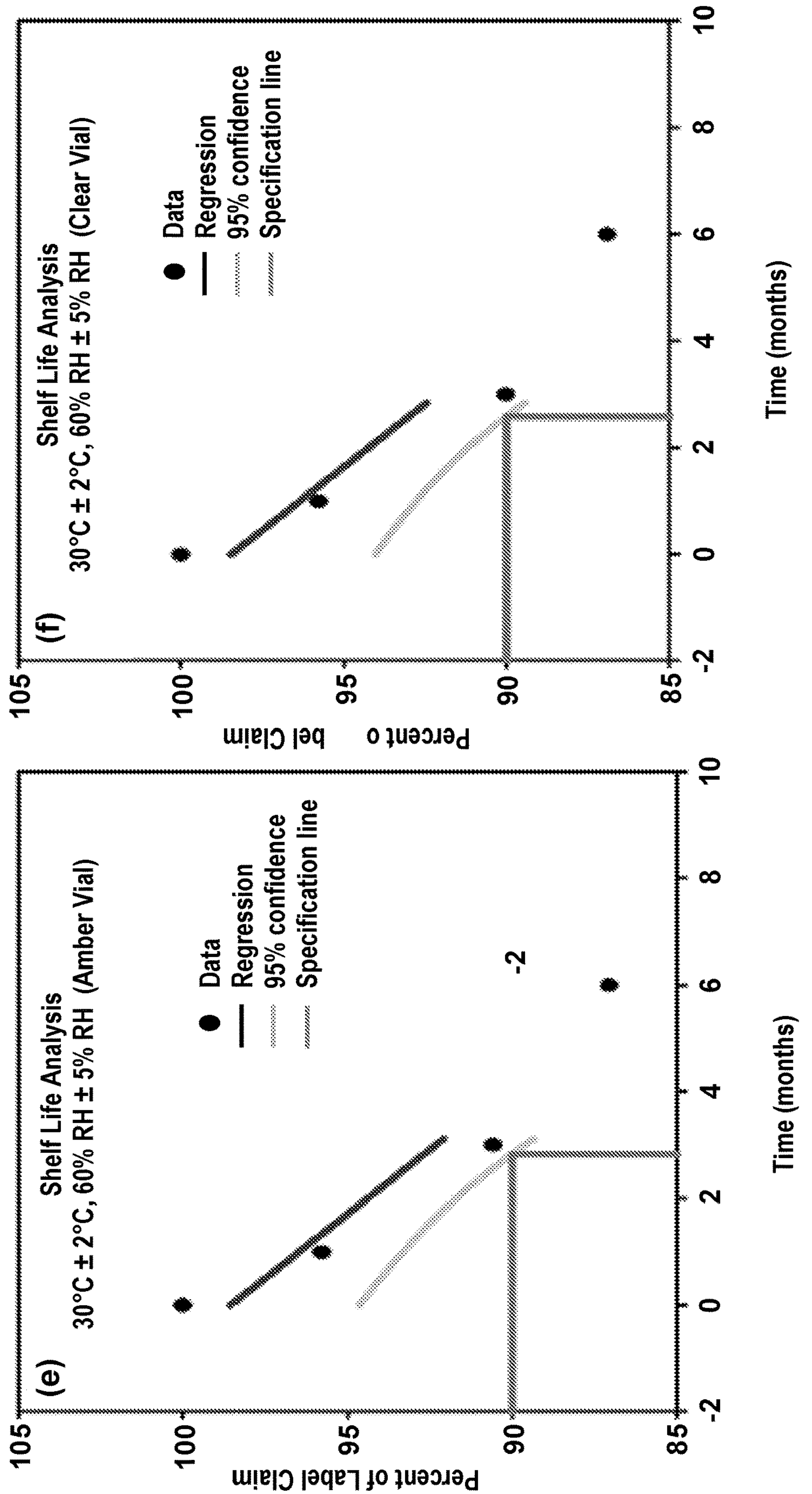
Figure 3:
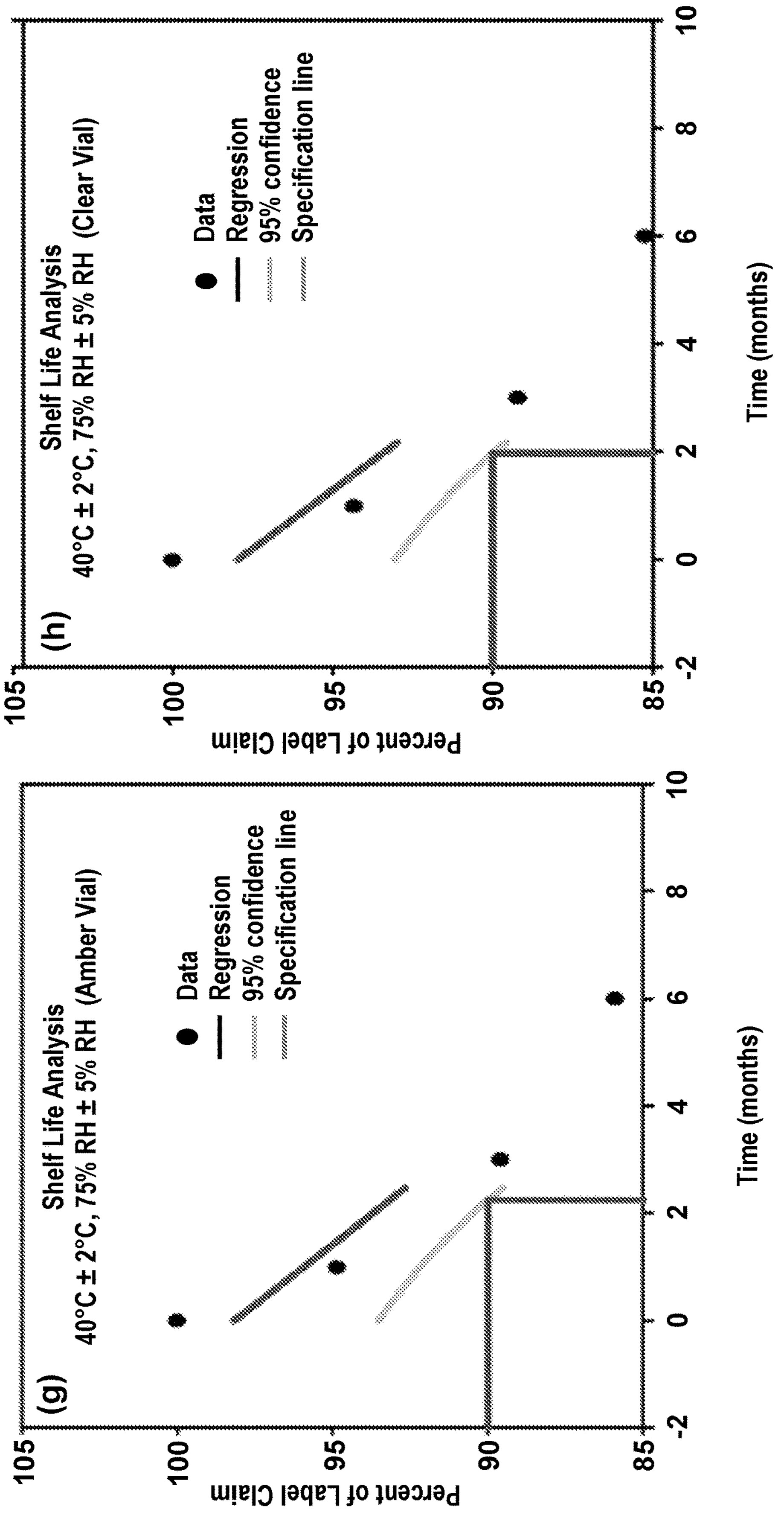

The optimized formulation was subjected to stability studies per the ICH Q1E and FDA criteria. The formed nanobubbles exhibited relatively short- and long-term stability in a liquid state depending upon the container and storage conditions (FIG. 3), which is a signature of stable nanobubble formulation. The nanobubbles were placed at room and accelerated temperature (1/T), and at different relative humidity (% RH) conditions, shelf life and statistical analysis of nanobubbles were utilizing the Sigma plot version 14.0. The result shows that the shelf life of nanobubble in the amber and clear vial container at 5° C.±3° C. was 4.52 and 4.26 months. Shelf life of nanobubble at 25° C.±2° C. RH 60% ±5% RH was 3.68 and 3.14 months. However, the shelf life of nanobubbles at 30° C.±2° C. RH 60% ±5% RH was 2.82 and 1.96 months. At extreme accelerated temperature and humidity 40° C.±2° C., RH 75% ±5% RH was 2.24 and 2.58 months. From the shelf-life analysis studies, we conclude that the ideal temperature and container were 5° C.±3° C., in an amber-colored vial.

TABLE 1

Parametric Range and Levels Defined in Rotatable Central Composite Design (RCCD) for Optimizing oxygen release, size, and zeta potential.
Study type: Response Surface
Design type: Rotatable Central Composite Design (RCCD)
Design model: Quadratic
Runs: 30 s
Parametric Range and Levels

| independent parameters | code | −α/−2 (axial minimum) | −1 (factorial minimum) | 0 (central) | +1 (factorial maximum) | +α/+2 (axial minimum) |
|---|---|---|---|---|---|---|
| Dextran % (w/v) | A | 0.55 | 0.7 | 0.85 | 1 | 1.15 |
| Potassium chloride % (w/v) | B | 0.015 | 0.03 | 0.045 | 0.06 | 0.075 |
| Sonication power (watts) | C | 20 | 30 | 40 | 50 | 60 |
| pH | D | 3.25 | 4.5 | 5.5 | 7 | 8.25 |

In our formulation by shifting the pH from alkaline to slightly acidic, the (potential shift towards a negative charge. The ζmeasurement illustrates that the oxygen nanobubbles are negatively charged with an electrical dual-layer, apparently due to the adsorption of negative OH- ions at the water/gas boundary. The ζpotential of the final optimized formulation was −58.8±1.3 mV as presented in (FIG. 2*d*).

Figure 4:
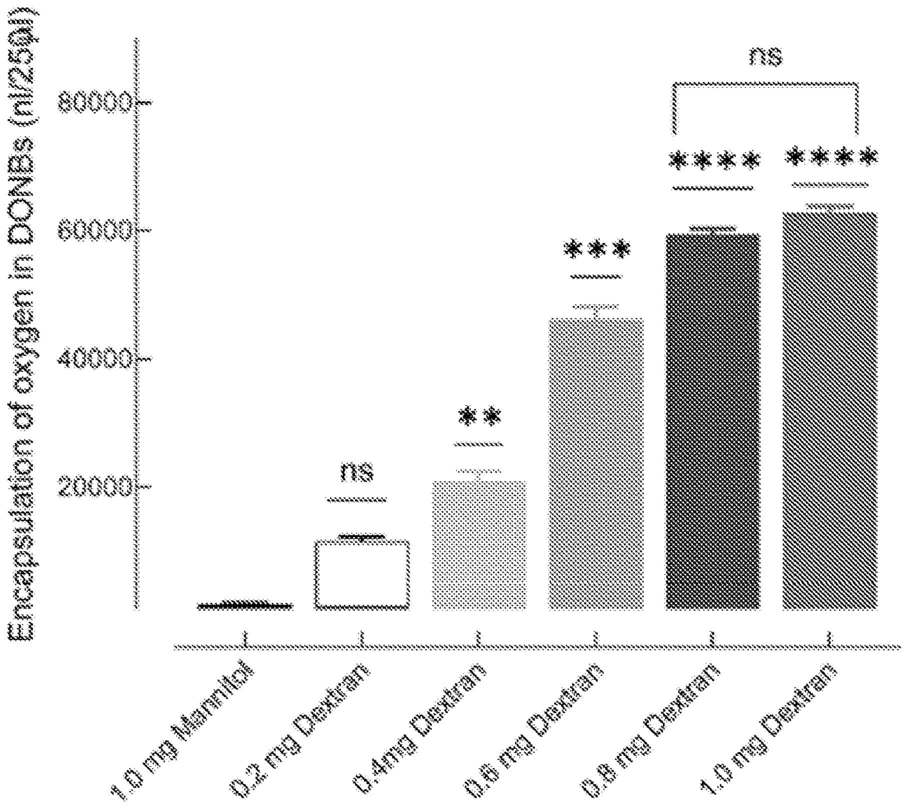
FIG. 4. Effect of dextran concentration on oxygen encapsulation into DONBs formulation at constant pressure 2 atm. The gas encapsulation was measured after releasing the pressure. The increased pressure led to linearly increasing oxygen entrapment. 0.2, 0.4, 0.6, 0.8, 1.0 mg dextran/ml led to the entrapment 1837, 11492. 20992. 46316. 59312, 62760 nl/250 μl of DONBs nl of oxygen, respectively, into the DONBs. Mean ±SD, n=3. **** $p<0.00001$ vs. mannitol solution only as control.

The percent encapsulation of oxygen in dextran nanobubbles was evaluated by using a previously reported method by Huang et al. (Ultrasound in Medicine & Biology 2008, 34 (8), 1272) by designing a separate set of experiments to assess the effect of different concentration of dextran on oxygen encapsulation into DONBs formulation A total of 500 p1 of the DONBs was transferred to 2 ml amber serum low extractable borosilicate glass vials 7 ×13 mm that conforms to United States Pharmacopeia (USP) Type I requirements to protect light-sensitive samples. The oxygen was introduced into the vial through Teflon tubing attached with a 30-gage needle. The pressurized oxygen gas/DONBs dispersion was incubated for 30 min at room temperature. As shown in (FIG. 4), entrapment of oxygen in the presence of a different concentration of dextran commenced to oxygen entrapment in a volume that was associated (substantially. linearly across the series of dextran concentration variations) we use a constant oxygen gas pressure 2 atm pressure led to the entrapment of 1837, 11492. 20992. 46316. 59312, 62760 nl/250 μl of DONBs. We also observed that there is no significant entrapment of oxygen difference between 0.8 and 1.0 mg of dextran. These phenomena also support our optimization studies by central composite design analysis.

The amount of encapsulated oxygen was measured using a previously reported method by Huang et al. By increasing the concentration of dextran, the critical component of the nanobubble shell, the volume of entrapped oxygen also increased which shows a direct relationship, The amount of oxygen volume was recorded by displacing the water from a five-microliter syringe to a 250 μl liter syringe. The volume of fluid replaced by the encapsulating gas was easily measured on a microliter syringe scale.

Figure 6:
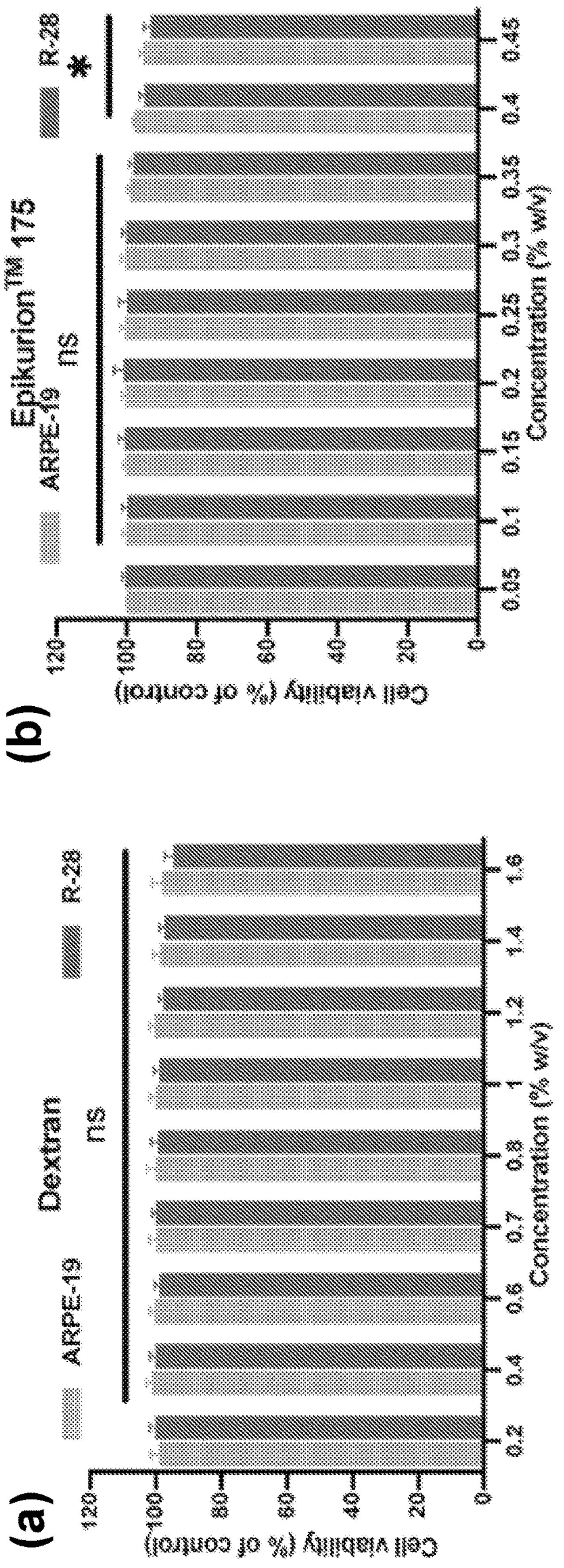
FIG. 6. (a-f) Cell viability of R-28 and ARPE-19 cell line incubated with different concentrations range of excipients used in our formulation's synthesis after 24 hours. (*$P<0.05$ is a statistically significant difference compared to the untreated control group n=3).
Figure 6:
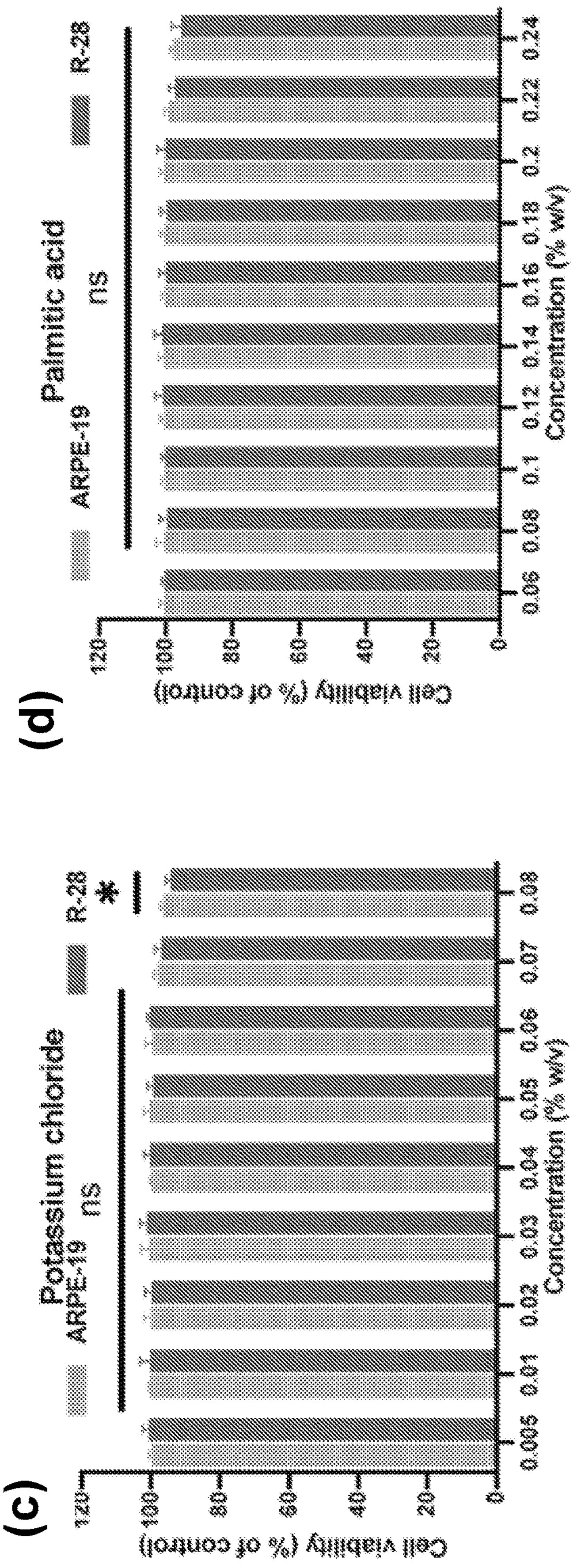
Figure 6:
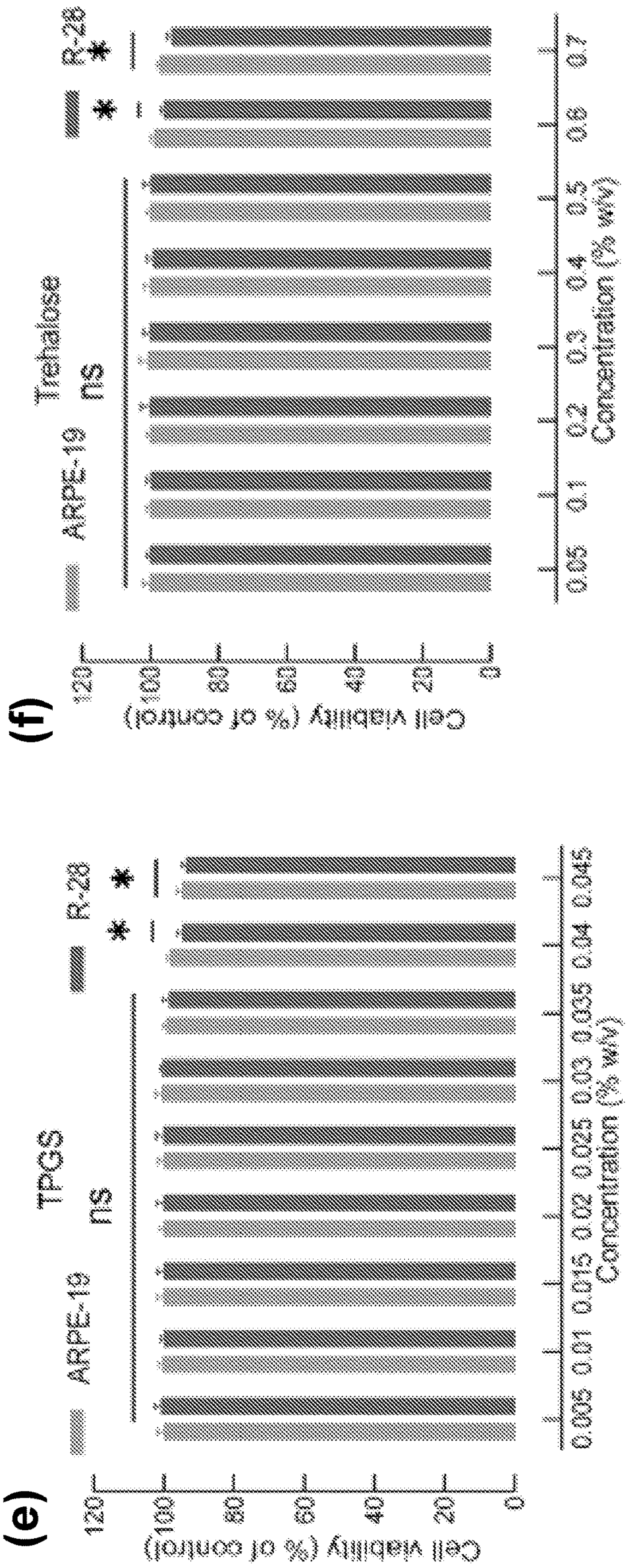

The biosafety of DONBs and excipients used in the formulation was evaluated on retinal precursor cells R-28 and retinal pigment epithelial cells (ARPE-19). The suspensions of the following cell line (100 μL, −60,000 cells/mL) were seeded into each well of a 96-well plate and cultured overnight. The cells were cultured for 24 h in the dark. The biosafety of the prepared excipients DONBs was evaluated on the R-28 and ARPE-19 cell cells, results revealed that excipients possessed excellent biocompatibility over a wide range of excipients concentration. Those concentrations which produce a toxic effect on the cell viability were excluded from the study and not use is the optimization and final formulation as depicted in the (FIG. 6). 1175, potassium chloride TPGS, and Trehalose produce some toxic effect at 0.4-0.45,0.008,0.04-0.045 and 0.6-0.7 mg respectively.

Figure 5:
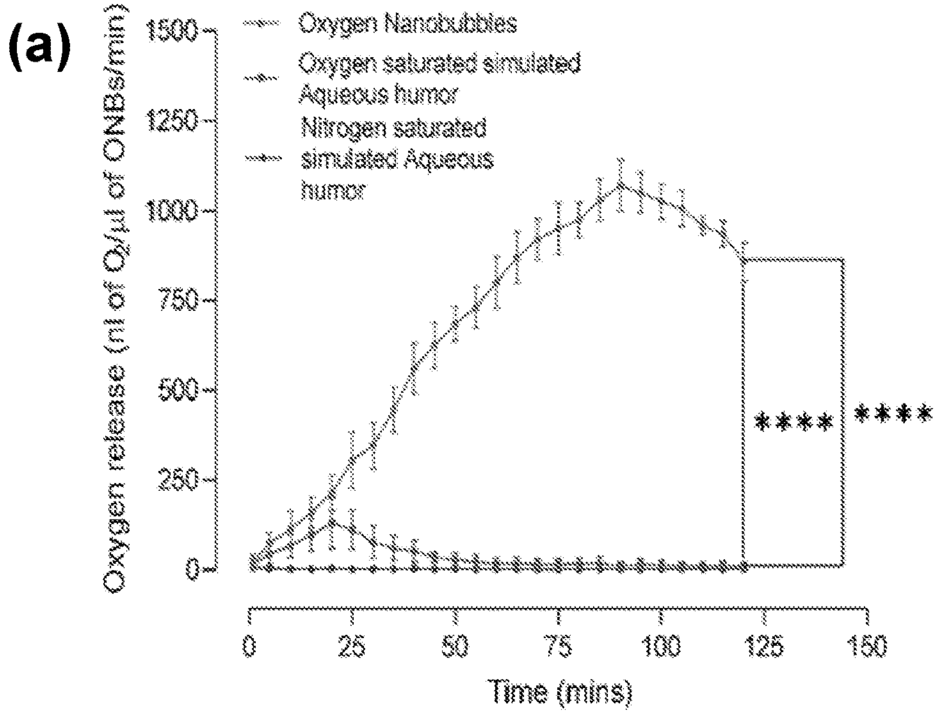
FIG. 5. Oxygen release profile from DONBs, (A) Oxygen release profile from DONBs in simulated aqueous humor, oxygen saturated simulated aqueous humor was used as a control. (B) Oxygen release profile from DONBs in simulated vitreous humor and oxygen saturated vitreous humor is used as a control. (C) Oxygen release profile from DONBs in porcine serum and oxygen saturated porcine serum was used as control. In all sets of experiments, we used nitrogen saturated aqueous/vitreous, and porcine serum was used as a baseline and temperature was maintain at 35° C. (n=3). ($p<0.0001$).
Figure 5:
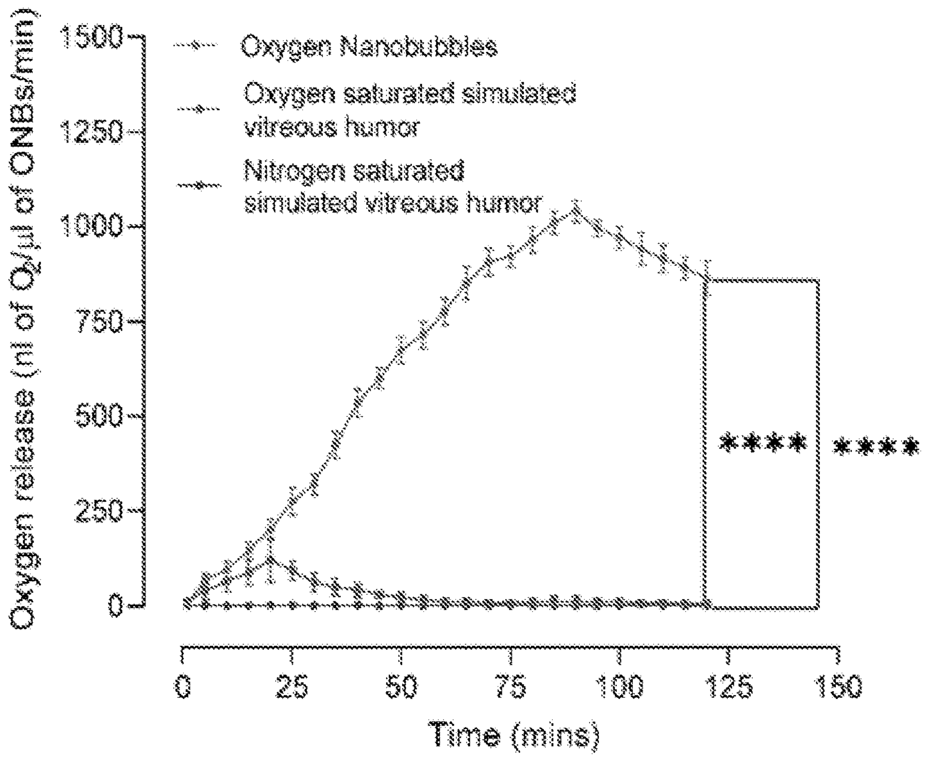
Figure 5:
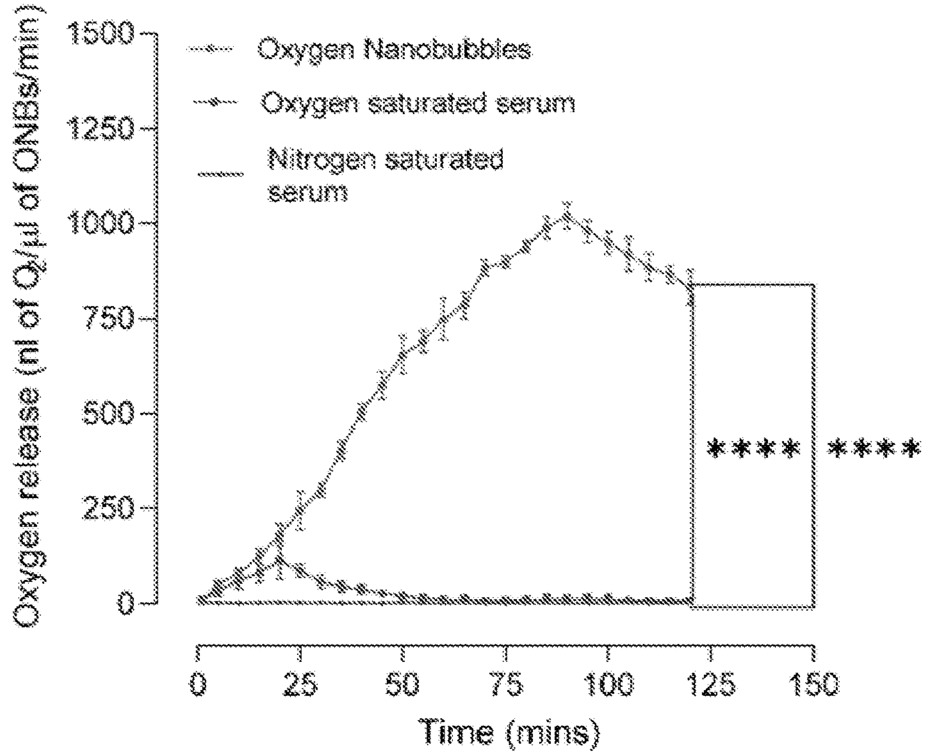

The oxygen release profile of DONBs was measured by monitoring the oxygen release rate in artificial fluids at 35° C. The DONBs was added to aqueous humor, vitreous humor, and porcine serum at 35° C. in the nitrogen environment, and the dissolved oxygen concentration of the final mixture was measured with a fiber-optic Oxylite™ Oxford optronic oxygen probes over time (FIG. 5). For all three simulated media, after the addition of the DONBs, the dissolved oxygen concentration increased slowly. The highest concentration of oxygen was achieved a plateau state at 75-90 minutes in the simulated fluids and then declined slightly to a moderately steady level because the dissolved oxygen diffused into the nitrogen environment. Notably, the release of oxygen in the aqueous humor achieved a little higher plateau than vitreous and porcine serum; this is because the higher viscosity of vitreous humor and serum helps to sustain the release of the oxygen in the vitreous and porcine serum slowly. We use 0.5 ml of simulated aqueous/vitreous and porcine serum as medium and 0.25 ml of DONBs in each set of experiments.

Figure 7:
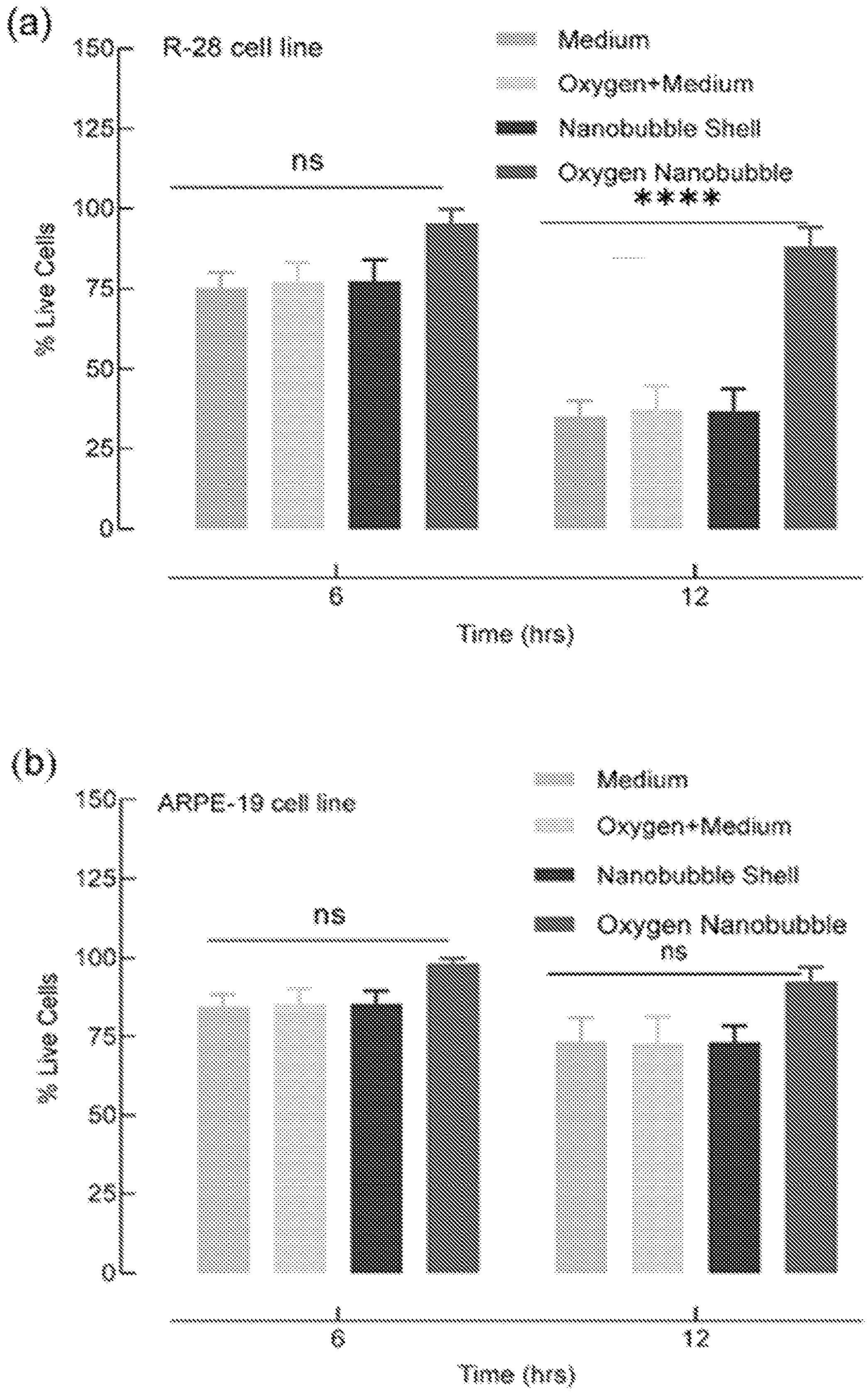
FIG. 7. Hypoxia recovery with DONBs in (a) retinal precursor cells (R28) and (b) retinal pigment epithelial cells (ARPE-19). Cells were treated with dextran encapsulated oxygen nanobubbles along with three controls (culture medium, oxygenated culture medium, and nanobubble shell) and assessed for viability. Results indicate higher viability in DONBs treated cells (n=3).

For hypoxia recovery, we incubate the cell lines in the hypoxic chamber. We use a mixture of gases to create hypoxia 2% $O_{2,\ 10}$% CO2, 88% N2 the protocol utilized to create a hypoxic environment for cell culture was adopted from the stem, cell technologies, and the hypoxic chamber was also used form the same vendor. The DONBs will be incubated for 6-12 hours and cell viability will be evaluated by MTT assay using the established protocol to confirm that the nanobubbles are non-cytotoxic. The results are shown in (FIG. 7*a*) for the R-28 cell line which indicates that nanobubble significantly improves the survival of cell in hypoxia up to 12 hours, however, in (FIG. 7*b*) the results indicate that there is no such significant improvement in Cell survival with and without nanobubbles this is because the ARPE-19 cell line itself is very resistant and able to survive in hypoxic conditions. Cell viability is helpful to access the overall performance of our DONBs because most of the cells which are affected more by hypoxia are retinal ganglion cells and our nanobubbles work well and improve the cell survival in the R-28 cell line. After successfully perform the excipients toxicity testing and results from the in-vitro cell viability studies we proceed towards animal studies.

Figure 8:
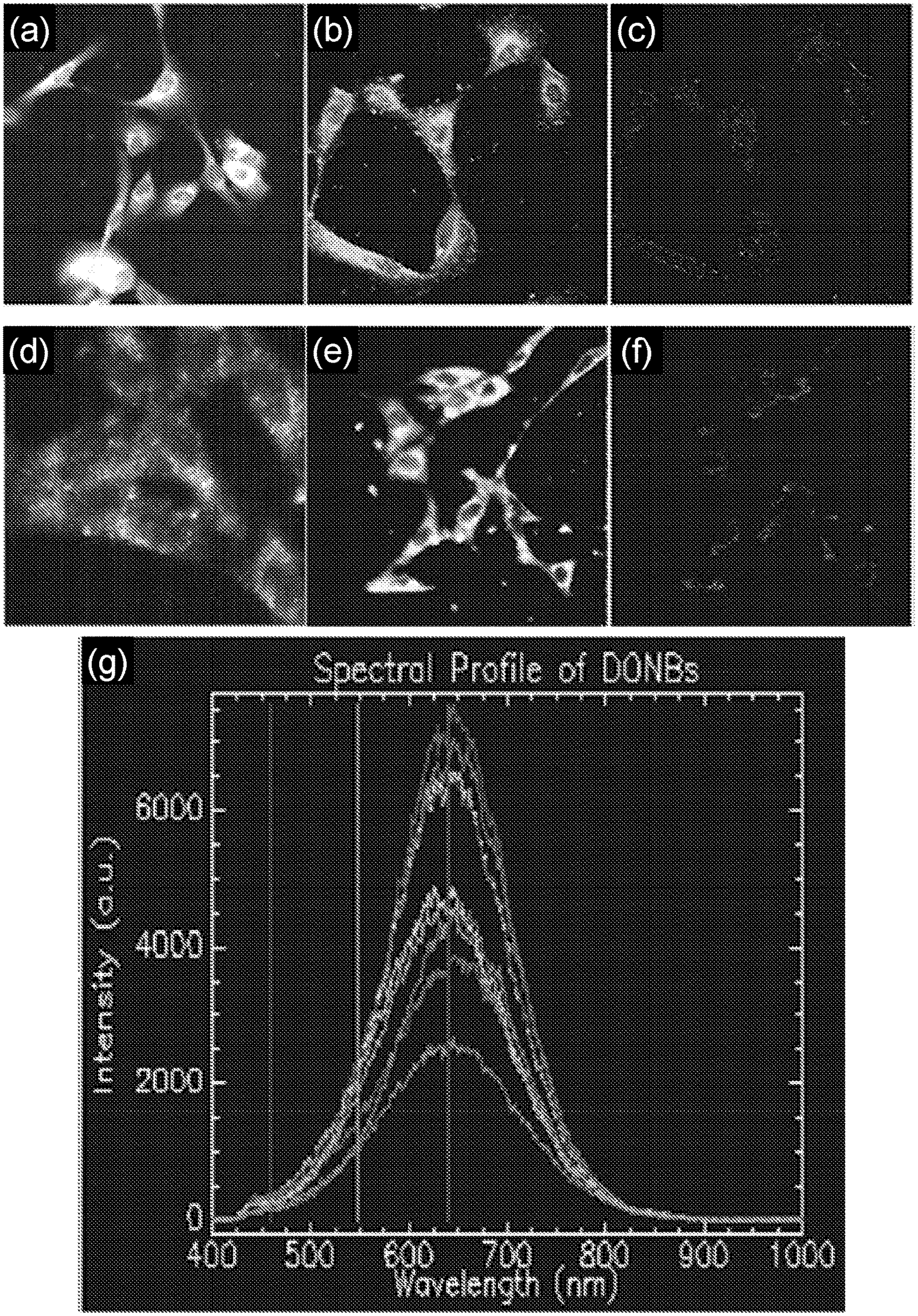
FIG. 8. Cellular uptake of DONBs through Hyperspectral Dark-Field Microscopy in R-28 and ARPE-19 Cell Line. (a and d) Hyperspectral images of control R-28 and ARPE-19 cells (b and e) are the hyperspectral images of R-28 and ARPE-19 exposed to DONBs, respectively. (c and f) Images are processed through spectral angular mapping algorithm to find the uptake of DONBs by these cell lines, respectively.
Figure 9:
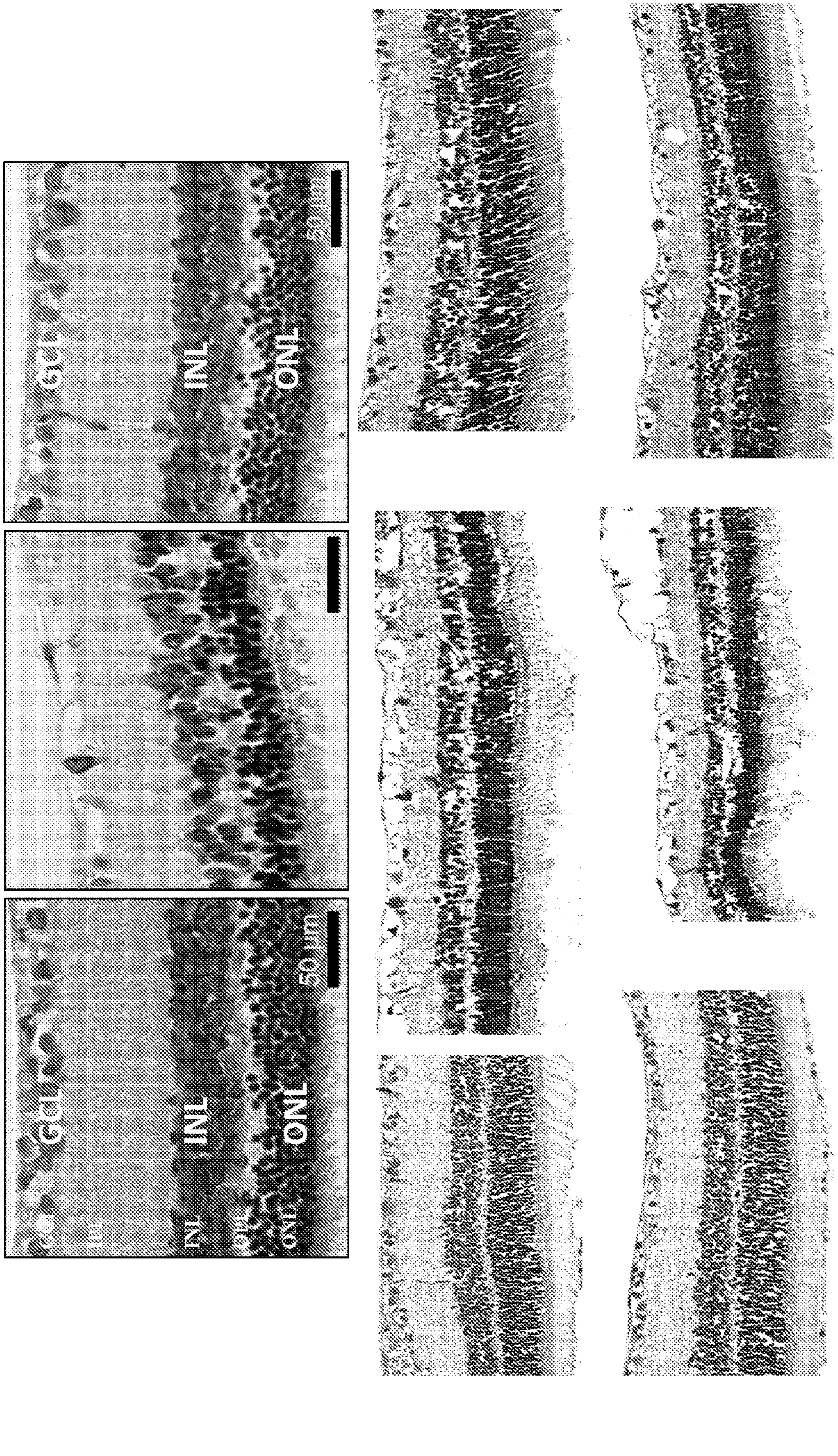
FIG. 9. Retinal layer thickness and cell count in control, hypoxic, and treated mode. Fig (A) histological stain of control retina all the layers of retina ganglion cell layer (GCL), inner nuclear layer (INL) and outer nuclear layer are full of cells, and the thickness of the whole retina is also in good health. Fig (B) illustrates the hypoxic retina without any treatment with DONBs. Histological study confirms that our hypoxia model works well, and the most affected cells are ganglion cells in upper later indicated with the red arrow. The overall thickness of the retina also reduced as compared to control in Fig (A). Fig (C) shows the recovery of ganglion cells after hypoxia with DONBs. The DONBs recover and maintain the cell count, and also the whole thickness of the retina is maintained.

The cellular uptake studies by ARPE-19 and R-28 cell line was carried out using the Hyperspectral Dark Filed Microscopy technique given in (FIG. 8). Hyperspectral dark-field microscopy (HS-DFM) is a non-destructive technique, which can recognize particles from their different optical signatures, with versatile computer algorithms. This non-destructive technique tracks the intracellular biodistribution of particles and allows precise observations of accumulation patterns. Hyperspectral imaging can also be used to create an image "map" to reveal the presence and position of desired substances in a biological specimen.

For our experiments, the ARPE-19, and R-28 cell lines was incubated for 2 hours with DONBs at 37° C. and 5% carbon dioxide environment. The cells were fixed on positively charged slides and imaged with a hyperspectral dark-field microscope (CytoViva, Auburn, AL), the result is shown in (FIG. 8*a* and d) are the hyperspectral image of the control images for R-28 and ARPE-19 cell lines. To identify the DONBs intracellularly, we built the spectral library of DONBs and saved in the spectral library memory folder, the (FIG. 8*g*) shows the spectral libraries of DONBs. The spectral library was then filtered with each image using a control image as a blank to identify the DONBs in the exposed cell image using (ENVI 4.8 software) Spectral Angle Mapper (SAM) algorithm. After mapping, the DONBs uptake by R-28 and ARPE-19 cell lines is shown in (FIG. 8*c* and f). respectively. FIG. 8*b* and FIG. 8*e* are the images of R-28 and ARPE-19 cell line with nanobubbles. The hyperspectral techniques show that DONBs are easily uptake by ARPE-19 and R-28 cell lines.

For in-vivo studies, we used 12-week-old Sprague-Dawley rats (Charles River Inc., CA, USA) per the University of Illinois at Urbana-Champaign Institutional Animal Care and Use Committee (IACUC) Protocol #108077 approved in 10/2018. We used a known ocular ischemia model where the right eye of the animal was used as a control, and the left eye was used as an experimental eye throughout the experiments. A 30 -gauge was inserted in the anterior chamber of the rat and Hanks' Balanced Salt Solution (HBSS) bottle elevated to increase the intraocular pressure (IOP) to >60 mmHg for 90 minutes.

DONBS are administered using a gastight syringe (Model 1702LT Threaded plunger Syringe, Part #80266) with a 31-gage Kel-F Hub needle 1.0 inches, point style 12° (Part#7750-22, Hamilton Reno, NJ, USA) through pars plana approximately 1 mm back from the limbus and directed perpendicular to the iris plane, into the vitreous cavity (FIG. 1*a*). The threaded plunger syringe helps to deliver DONBs in a controlled manner to avoid unnecessary elevation of IOP. The volume of DONBs per rotation administered was 0.33 μl. The syringe was attached to a manual micromanipulator (Mirzhauser Wetzlar GmbH & Co. KG; Model HS 6) HS with a 0.01 μm resolution. During the experimentation IOP level was monitored, 5 μl DONBs was used as the dose in all of our work. This is within the reported range of 2-20 p1. DONBs was injected in the treatment group 1 hour before the induction of ischemia to give time for diffusion into the inner retina. The oxygen concentration in the vitreous cavity of the study eye will be determined and compared with untreated eyes using Oxylite™ Oxford optronic oxygen probes. Further, we will also assess whether the hypoxic damage to the retina has been mitigated in the treated vs. the untreated ischemic eyes.

Figure 15:
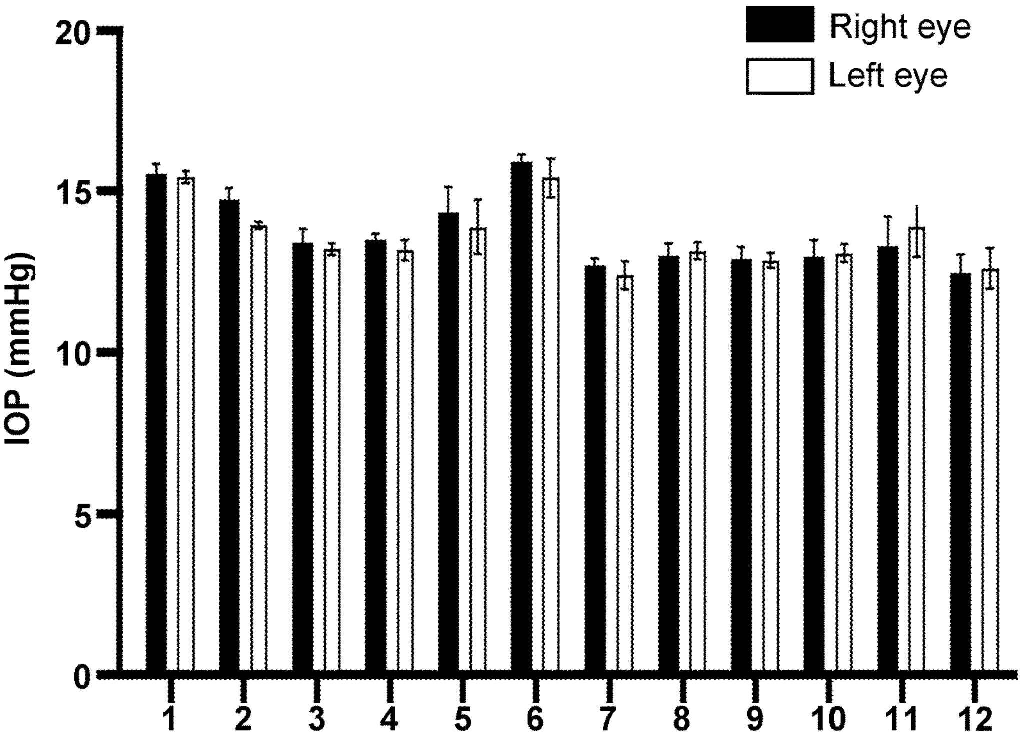
FIG. 15. Intraocular pressure in rats after acclimatization period in all groups.

In our $1^{st}$ set of experiments we use 6 rats three males and three females (Sprague-Dawley rats; Charles River Inc., CA, USA) per treatment. Intraocular pressure (IOP) is an essential measurement of eye health. Upon arrival, animals were allowed at least two weeks for acclimatization. After the acclimatization period, intraocular pressure in the right and left eye was measured for seven days. IOP measurements were repeated until the average of 4 to 5 consecutive values reached the level with a coefficient of variation less than 5% values are mean±SD for seven days. Each value and error bar represents the mean IOP ±SD. for 12 right and 12 left eyes every day, and the average are plotted in the graph pad prism. The data of IOP is presented in two groups of animals because we buy a total of 24 animals 12 animals in each order 6 males and 6 females. (FIG. 15) ($p<0.05$, unpaired Student's t-test). All IOP measurements were conducted at the same time of day (10 am - 12 noon) by the same observers. IOP measurements began within 5 min of inducing anesthesia, and the animals were awake within 30 min of the TOP measurement. As noted in (FIG. 15), after the intravitreal injection of 5 μl of ONBs solution, the IOP increased to only 16 mm Hg but returned to normal levels within 6 hrs. This is also consistent or perhaps better than those previously reported. As high as 16 mmHg was noted, upon injection of 5 μl of nanobubbles. In FIG. 15, the IOP was monitored for up to 24 hours post-injection. All injections were performed on the left (experimental) eye. The largest difference between both eyes was reached by 1.5-hour 16.00±1.45 mmHg vs. 13.54±1.00 mmHg, $p<0.005$. The intraocular pressure returns to normal at 6 hours (13.64±1.06 mmHg vs. 14.28±1.20 mmHg, $p<0.05$ (unpaired Student's t-test), indicating that a second dose can be administered, if needed.

After each set of experiments, both eyes were enucleated and used for histologic examinations to identify the retinal morphological changes, according to the established protocols reported elsewhere both for comparison with and without oxygen nanobubbles treatment. The hematoxylin-eosin (H&E)-stained sections were used to assess the retinal damage and retinal layer thickness. For each section, digitized images of the retina were captured and recorded. We also perform a $2^{nd}$ set of an experiment in which we use a total of 12 animals the same strategy was applied left eye use an experimental eye, right as a control of the same six animals. The remaining six animal eyes were used as hypoxic control. A flexible, minimally invasive sensor, suitable for localized oxygen measurements (NX-BF/O/E Oxylite™, Oxford Optronics, UK), was used to measure the oxygen distribution in control, hypoxic and ONBs-treated eye. The probe was inserted into the rat eye through a small hole placed just posterior to the limbus using a customized CMA 11 cannula. A plano-concave contact lens was placed on the cornea, which in conjunction with an operating microscope (SM-3TZ-54S-5M, Amscope, Irvine, CA, USA), yielded a high-quality stereoscopic view of the fundus.

Figure 10:
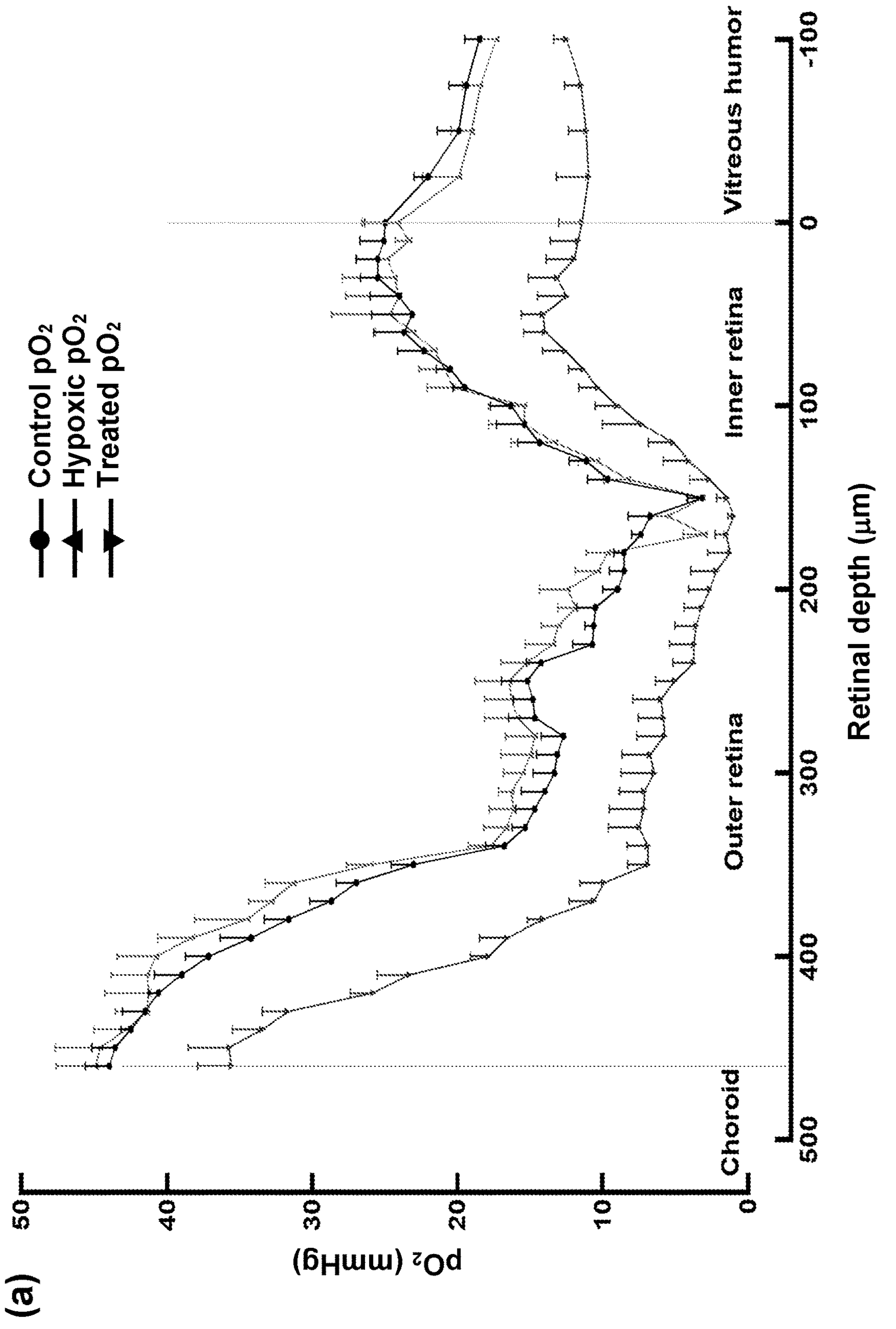
FIG. 10. Hypoxia recovery with DONBs. Figure (A) The partial pressure of oxygen $pO_2$ in control, hypoxic, and treated eyes n=6, 3 male and 3 females. Figure (B) is a wave of ERG and (C) is b wave in control and treated rats at 6 hours and 24 hours post-administration of DONBs.
Figure 10:
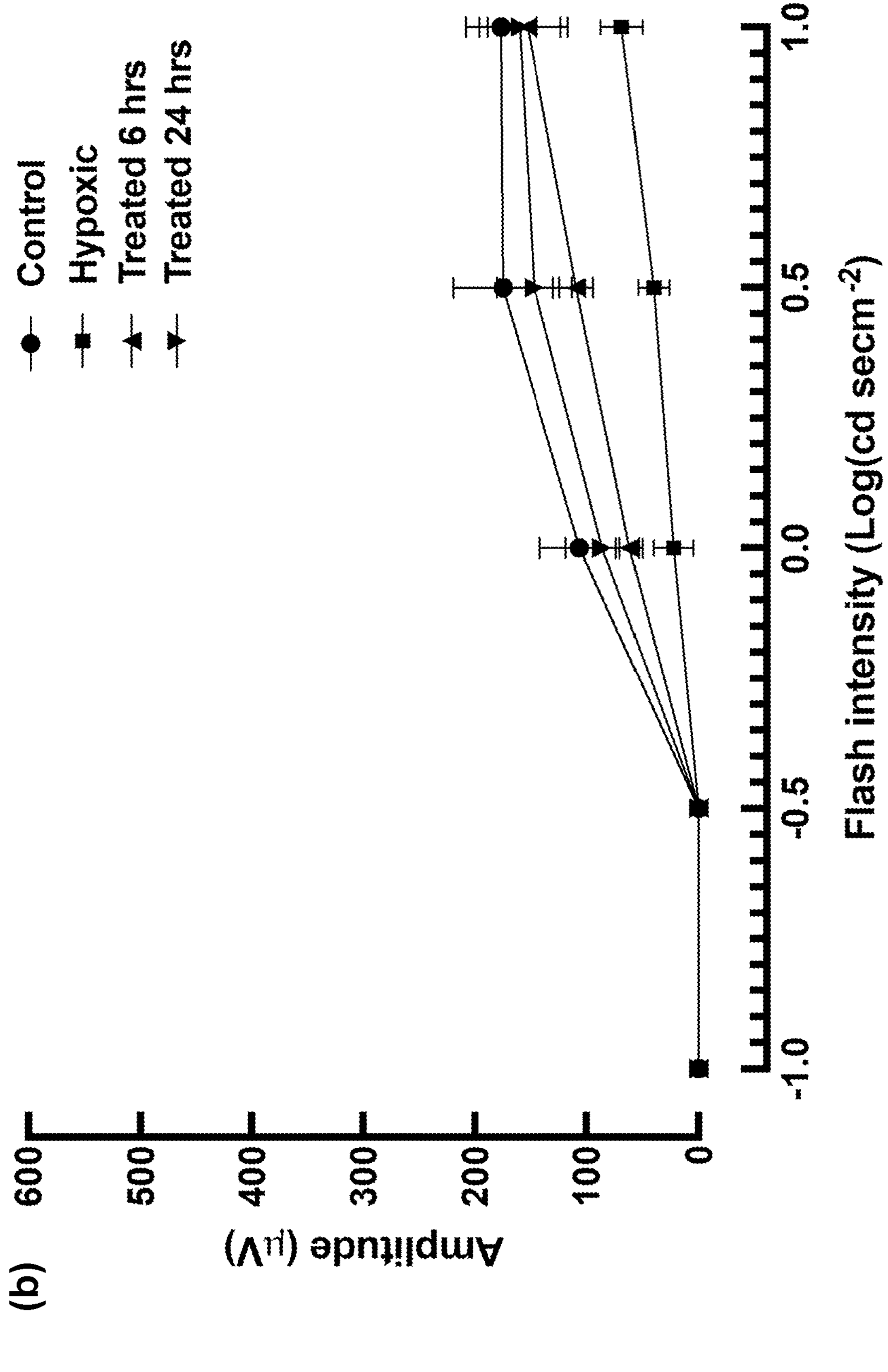
Figure 10:
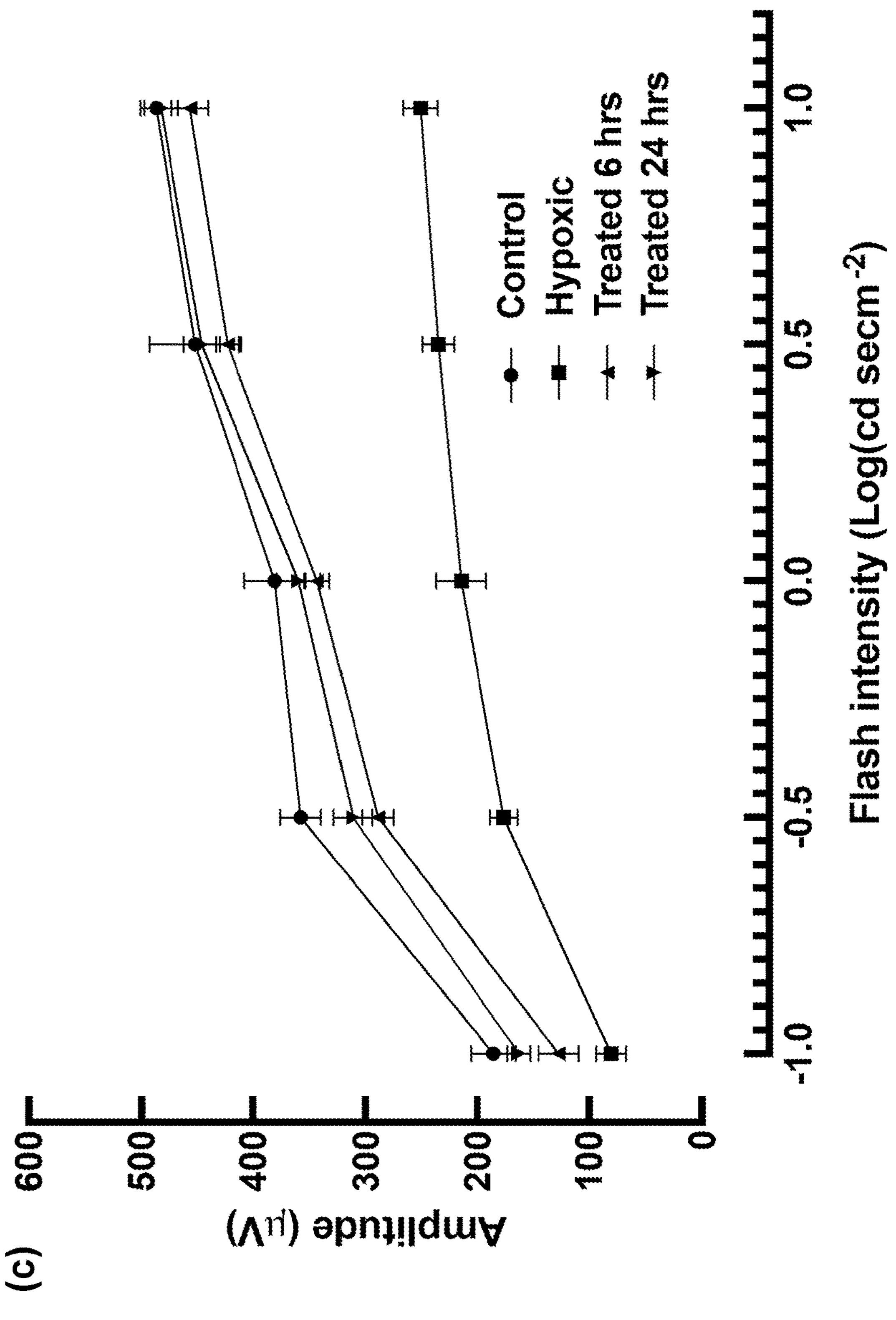

A flexible, minimally invasive sensor, suitable for localized oxygen measurements (NX-BF/O/E Oxylite™, Oxford Optronics, UK), was used to measure the oxygen distribution in control, hypoxic and ONBs-treated eye. The probe was inserted into the rat eye through a small hole placed just posterior to the limbus using a customized CMA 11 cannula. A plano-concave contact lens was placed on the cornea, which in conjunction with an operating microscope (SM-3TZ-54S-5M, Amscope, Irvine, CA, USA), yielded a high-quality stereoscopic view of the fundus and the electrode, to determine the placement of the electrode tip in the retina. All measurements were performed under dim red light (k>600 nm). The oxygen electrode was coupled with Oxylite™ monitor, and the analog output of the Oxylite™ monitor was connected with PowerLab 16SP (AD Instruments Inc.). The measurements in the experimental eye were done 6 hours after oxygen nanobubbles treatment. This time point was chosen since Tmax for oxygen diffusion in the retina was 4 hours. (FIG. 10*a*) shows intraretinal $pO^2$ profiles from control, hypoxic, and treated rat eyes a total of six rats were used, three males and three females. There is early evidence that ONBs-treated hypoxic eye had an almost typical $pO_2$ profile in vitreous (25-20 mmHg), inner retina (5-20 mmHg), outer retina (15-5 mmHg), and choroid (−45 mmHg) with values in line with the control eye and consistent with previous reports The hypoxic eye has much lower $pO_2$ values for all tissues.

Our ischemic model causes more of global ischemia, which is akin to an ophthalmic artery occlusion as opposed to retina artery occlusion. Ischemia must not be complete since some oxygenation exists, although a significant hypoxic state is expected. Furthermore, the area of the retina that most crucially requires oxygenation is −22.7% (5 mm diameter of the macula while the entire retinal diameter is 22 mm in the human eye). For the clinical evaluation of CRAO and similar ischemic conditions, the inner layers of the macula would need to be maintained as opposed to the entire retinal surface to preserve the majority of vision. Despite more global ischemia, the proposed ONBs technology shows excellent promise in mitigating hypoxia. To this effect, the oxygen consumption in rat inner retina is 2.3 ml of oxygen per 100 g of tissue.

The oxygen requirement of rat retina is $2^6$-$3^6$ nl/100 μm, and human requires 107 nl/100g/min. Another study established that the inner retina oxygen consumption is approximately 1200 nanomolar/hr on a weight-adjusted basis. The maximum oxygen release from the synthesized DONB's with 0.5 ml dose was 3.68 ml/min in simulated aqueous humor, 3.513 ml/min in the simulated vitreous humor, and 3.355 ml/min in serum. The DONBs oxygen release was measured with an Oxylite™ probe and recorded with the PowerLab SP16 data acquisition device using Chart 5.1 software. The recorded data were analyzed according to Henry laws and commercially available online calculator Loligo Systems, Tjele. According to the in-vitro release study in the simulated aqueous humor, vitreous humor, and serum, DONBs fulfill the requirement of oxygen consumption for the inner retina in rats and humans that is most vulnerable to cause blindness in a hypoxic state. In the case of humans, the total retinal oxygen requirement is 10 ml/min. The inner retina is approximately 25% of the whole retina, which means 2.5 ml/min is required by the inner retina. The outer retina, including the photoreceptors and underlying retinal pigment epithelium, is supplied with oxygen by the choroidal circulation derived from the long and short posterior ciliary arteries and is not infarcted in pure CRAO. Therefore, our main target is the inner retinal recovery in case of hypoxia.

The retinal function was assessed with electroretinogram (ERG) recording of live animals in treated vs. untreated eyes. The retina is comprised of layers of specialized cells, including photoreceptors (rods and cones), that detect light and ganglion cells that transmit images to the brain. Specifically, the ERG picks up electrical signals from the photoreceptors, as well as other cells (Muller cells and bipolar cells) that act as intermediaries between the photoreceptors and the ganglion cells. Here, lower a- and b-wave amplitudes (FIG. 10*b* and c) signify hypoxia impairments in retinal photoreceptor function. In these and other hypoxia endpoints, the non-hypoxia eye serves as a robust negative control for the relative assessment of hypoxia-induced damage. We observed ERG data from 6 eyes further supports the claim that ONBs mitigate hypoxic insult. The hypoxic eye clearly shows diminished a and b waves, indicative of impaired function. The treated eye at 6 and 24 hours has an almost normal response of both a and b wave.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Examples

Example 1. General Methods

Materials. Dextran sulfate sodium salt (200 kDa) (Sigma 67578-5G), D-(+)-Trehalose dihydrate (Sigma T5251-10G), potassium chloride (Sigma P9541-500G), D-a-tocopherol polyethylene glycol 1000 succinate (Sigma 57668-5G) stearic acid, Sodium sulfate HPLC grade (Sigma 80984) were purchased from Sigma-Aldrich a subsidiary of Merck KGaA, Merck Millipore Sigma). Epikuron™ 170 phospholipid deoiled soy lecithin was a kind gift from Cargill, Germany. Sterile Water for Injection, USP/EP (RMBIO 10837-184). HPLC grade water. All chemicals were used as received without any modification. Clear serum vials 7×13 mm (Cat #23683) and amber serum vials 7×13 mm (cat #223693) purchased from Duran Wheaton Kimble Life Sciences (Millville, New Jersey, USA). OxyLite™ bare fiber type oxygen sensors product code 'NX-BF/O/E' (Oxford Optronix, Oxford, UK).

Synthesis of nanobubbles. The DONBs were synthesized using ultrasonication cavitation and high-speed homogenization method. Briefly, 50 ml sterile water for Injection (USP), was oxygenated and sonicated, 1 ml 0.045% potassium chloride was added to reduce the size of the bubbles under continuous oxygenation and sonication at 50 watts per sec for 5 minutes using Branson sonifier* SFX250, the oxygenation level was maintained at partial pressure >200 mmHg. After five minutes, 3 ml 0.23% Epikuron™ 170, 2 ml 0.018% of D-a-tocopherol polyethylene glycol 1000 succinate (TPGS) were added to the solution. The solution was switched to homogenization at 18000 rpm by using Ultra-Turrax T18 homogenizer (IKA, Staufen, Germany). During homogenization, 5 ml 0.9% dextran was added, and homogenization speed was increased to 22000 rpm for 5 minutes. The resulting solution was sonicated at 50 watts per see for 5 minutes. Next, 1.5 ml of 0.19% palmitic acid was added, followed by the addition of 2 ml 0.40% trehalose solution. The whole formulation was performed on an ice bath, and the internal temperature of the solution was maintained at 4° C. The DONBs produces were filtered with a 0.22 μm filter and stored in clear and amber-colored borosilicate glass vials for characterization studies.

Stability studies. The shelf life of DONBs was estimated based on the "ICH, Q1E Harmonised Tripartite Guideline for Evaluation for Stability Data, International Conference on Harmonisation of Technical Requirements for the Registration of Pharmaceuticals for Human Use". DONBs formulations were stored at different temperatures and humidity conditions per FDA and ICH guidelines. The single batch of DONBs stability data was analyzed with SigmaPlot version 14 (SYSTAT Software Inc., San Jose, CA, USA). The nanobubbles were placed at 5, 25, 30, and 40° C. with the controlled relative humidity of 60% and 40% in clear and amber color vials. After 6 months at the specified temperature and relative humidity, we measure the concentration of oxygen and compare it with the concentration oxygen at the time of nanobubbles preparation.

Excipient toxicity studies on ARPE-19 and R28 cell line. Cell viability was conducted with ARPE-19 and R28 cell lines, in response to treatment with nanobubble excipients, using the [3-(4, 5-dimethylthiazol-2-yl)-2, 5-diphenyl tetrazolium bromide](MTT) assay. The MTT reagent (Cat no. M6494, Thermo Fisher Scientific) was prepared by dissolving 5 mg of MTT per 1 ml of phosphate-buffered saline (Cat no. 21-040-CV, Corning), filter sterilized using a 0.22 μm filter, and stored in dark at 4° C. Yellow MTT is reduced to purple formazan in the mitochondria of living cells. Cells were grown to 80-90% confluence in a T-25 flask, dissociated using trypsin, and seeded into a 96-well plate at a density of 10000 cells per well. Cells were incubated at 37° C. and allowed to adhere for 24 hours, then treated for 48 hours at 37° C. with various concentrations of excipients (dextran, 0.2-1.6% w/v; palmitic acid, 0.06-0.24% w/v; Epikuron™ 170, 0.05-0.45% w/v; potassium chloride, 0.005-0.08% w/v; TPGS, 0.005-0.045% w/v; trehalose, 0.05-0.7% w/v). To each well, 20 μl of reagent was added including control wells, and incubated for 4 hours at 37° C. 150 μl MTT solvent (0.1% acidified IGEPAL® CA-630 in isopropanol) was then added to each well, covered with aluminum foil, agitated on an orbital shaker for 15 minutes. The absorbance was measured at 590 nm with a reference filter of 620 nm. The results are presented in FIG. 6 as the percentage of the control values for cells grown concurrently in the absence of any excipients.

Cytotoxicity of oxygen nanobubbles was evaluated on the retinal pigment epithelial (ARPE-19) and 12S ElA-immortalized rat retinal cells (R28) cell lines. The cells suspensions (100 μL, ~-60,000 cells/mL) were seeded into each well of a 96-well plate and cultured overnight. Consequently, the culture medium was replaced with a fresh medium, including DONBs solution at a concentration from 0.03 to 4 mg/mL. The cells were cultured for 24 h in the dark. After that, 100 μL of a fresh medium containing 10 μL of Cell Counting Kit-8 (CCK-8, Dojindo, Japan) was added to replace the previous culture medium, and the cells were incubated for another 4 hours. To evaluate the cell viability, the absorbance of each well in the 96-well plate was measured with a multimode microplate reader (Varioskan LUX, Thermo Fisher, USA) at 450 nm.

Nanoparticle tracking analysis. Nanoparticle tracking analysis (NTA) (NS300, Malvern instrument) was used with a blue laser light source (Q=488 nm) to measure the hydrodynamic size and concentration of nanobubbles. It was equipped with a 20-magnification microscope and a high-speed camera. When the laser light struck the particle, scattering faculae formed. The track of scattering faculae was recorded by the high-speed camera. Each result was gathered from the average of five measurements, and the movie was last for 60 seconds, captured at 25.0 frames/s. The camera level was usually set at 10, the threshold was set at 3 and the solution viscosity was 1 CP. The optical field of view was fixed (approximately 100 m by 80 μm) and the depth.

Zeta potential. Electrophoretic mobility and light scattering method were used for zeta potential measurement using Malvern Zetasizer Nano ZS90 (Malvern, Worcestershire, UK). The dispersion technology software version 7.13 was used to record the zeta potential measurement and analysis. As proposed by IS013099, the Smoluchowski model was used to calculate zeta potential values of nanoparticles in aqueous media. Zeta potential experiments were averaged from three runs of between 10 and 100 scans at 25° C.

Measurement of the amount of oxygen gas into dextran nanobubbles. A total of 500 1 of the DONBs was transferred to 2 ml amber serum low extractable borosilicate glass vials 7 ×13 mm that conforms to United States Pharmacopeia (USP) Type I requirements to protect light-sensitive samples (cat #223693 Wheaton Millville, New Jersey, USA) These glass vials were then capped with straight plug ultra-pure stoppers 7×13 mm (cat #W224100-400 Wheaton Millville, New Jersey, USA). The ultra-pure seal stopper was a seal with an open-top lined aluminum seal using Wheaton crimper (cat #W225711). The oxygen was introduced into the vial through Teflon tubing attached with a 30-gage needle, and the pressure was controlled and recorded with Miller Smith 30-1000-540 Oxygen Medium Duty Regulator. The pressure created by the injected oxygen gas volume was calculated from Boyle's Law and the volumes of the vial and syringe. The ultra-pure stoppers used were tested for leakage at the highest pressure required in our investigation and found not to release detectable amounts of oxygen investigated for at least 48 h. The pressurized oxygen gas/DNBs dispersion was incubated for 30 min at room temperature. The pressure was released by removing the aluminum caps immediately after 30 min. Oxygen gas and calcein encapsulation were measured at room temperature.

The amount of encapsulated gas was determined using a previously reported method (18). Briefly, a 0.5-1 mL of DONBs containing 0.818 dextran/mL and 0.290 mg phospholipid/ml is put into a 5-mL syringe. A two-way Luerlock stopcock is coupled to the syringe and the air is displaced from the syringe and stopcock by depressing the plunger. The stopcock is closed, and a 250-μL syringe, without a plunger but containing a 30- L volume of water, is coupled. The plunger of the large syringe is withdrawn to generate a vacuum that releases oxygen from the DONBs. After turning the stopcock to connect the large and small syringe bodies, and holding the large syringe so that the DNBs are at the bottom (away from the stopcock), the plunger is depressed to transfer the released oxygen into the small syringe, where its volume at ambient pressure is measured according to the displacement of the 30- L bolus of water.

Preparation of ocular ischemia model in rats. The hypoxia model was developed according to the reported method (JoVE 2016, (113), e54065). Experiments were performed on a total of 24 Sprague-Dawley rats, body weight 250-350 g. Rats were housed essentially two per cage, with a 12:12 hours light-dark cycle. The ambient light level averaged 290 lx, which ensured normal photoreceptor density. Rats were anesthetized with an intraperitoneal injection of Ketamine/xylazine/acepromazine, 50:10:1.5 mg/ml cocktail. The dose of the cocktail administered was 0.1 ml/100g of rat weight. Ketamine 0.lml/100g 25 mg/ml was used to maintain the anesthesia. After anesthesia places the rat under the surgical microscope and focuses the cornea. Underneath the surgical microscope, use forceps to softly hold the eye. Gently insert the 30-gauge needle into the anterior chamber about the center between the zonule fibers and the apex of the cornea caution to avoid scraping or piercing the iris, lens, or inner corneal surface also avoid piercing the cornea multiple time or more than once. Gently twisting motion to overwhelmed resistance between the needle and the cornea, insert the needle deeply in the anterior chamber. With the help of surgical tape hold the tubing to the table. To diminish movement of the inserted needle, press the tubing against the tabletop. After that record the starting time of surgery. By using a microscope check is the leakage of there is leakage apply Hypromellose, Hypromellose seals the leakage area. With the help of a surgical microscope verify the presence of ocular distention this distension demonstrates a successful elevation of intraocular pressure. Intraocular pressure verify with the help of tonometer maintain the IOP >90 mm Hg for 90 minutes.

Intraocular pressure measurement. The intraocular pressures (IOP) of Sprague Dawley rat's eyes were measured to establish the normal IOP in this animal model after two weeks of acclimatization. All measurements were done between 10:00 am and 12:00 μm to reduce IOP variations due to circadian rhythm for one week. All animals weighed between 250 and 300 μm; 24 rats were male, and 24 were female. Before the IOP determinations, one drop of 0.5% proparacaine hydrochloride was administered to each eye. To avoid a pseudo, rise in IOP, no stress was exerted on the eyelid because the eyes were open. IOPs were measured using a rebound tonometer (Icare* Tonolab, Finland Oy, Helsinki, Finland). Three automated means of adequate analyses were displayed on the Tonometer when the statistical reliability of the average measurement (SRAM) was <5%. If the SRAM were >5%, another measurement was taken. The Mean IOP, with standard deviation, was estimated to determine the range of normal IOPs for Sprague Dawley.

H&E Staining. After treatment with DONBs, the eyes were enucleated after 12 hours and the injection volume was 5 μl and the nanobubbles used were without dilution, and the retina was separated according to establish protocols reported elsewhere. To assess retinal damage thickness of retinal layers and cell count was measured on hematoxylin-eosin (H&E)-stained sections. For each section, digitized images of the retina were captured using a digital imaging system Olympus Q-color 5 RTV (5 Megapixel) equipped with Olympus microscope BX51 (Olympus, Tokyo, Japan) at 20× magnification. The camera was operated with Q Capture Pro 7 software (Teledyne digital imaging, Inc Surrey BC Canada).

Cellular uptake of DONBs. The quantification of DONBs uptake by R-28 and ARPE-19 c cell lines was carried out using the Hyperspectral Dark Filed Microscopy technique given in (FIG. 8). For imaging, the cells were cultured on positively charged slides and allowed to adhere. After 24 hours, the medium was replaced with the DONBs, separately, and incubated for 2 hours at 37° C. The slides were then washed with phosphate-buffered saline (PBS) and cells were fixed with 4% paraformaldehyde. The method we use for identification and quantification was developed by our group published elsewhere using an enhanced darkfield illumination system (CytoViva, Auburn, AL). Briefly, the method uses advanced optics and algorithms for the investigation of hyperspectral dark-field images to analyze the interfaces between cells and administered compounds. This non-destructive technique quantitatively tracks the intracellular biodistribution of nanobubbles and allows precise observations of accumulation patterns. The uptake/accumulation of DONBs in intracellular space after two hours of incubation was adopted following several repetitive experiments. To identify and quantify the DONBs in cells first, we create the spectral library of DONBs and save them in the spectral library folder. The cells grown on positively charged slides without DONBs administration were scanned and captured as a control image.

The spectral data were analyzed by using the CytoViva software program (ENVI 4.8 and ITT Visual Information Solutions). Hyperspectral information is normally assembled (and described) as a data cube with spatial information obtained in the X-Y plane, and spectral data described in the Z-direction. The processing of image and data interpretation included some steps that are essential for creating spectral libraries. The spectral libraries were collected by defining a region of interest (ROI) from the scanned specimen. The ROI choice allows choosing pixels that best describe the morphological state of cells. When the required specific spectral libraries were recognized, they were kept in a spectral library folder by the CytoViva ENVI software for the following spectral mapping of the hyperspectral images of other specimens. Each spectrum involved in the library was collected from a single-pixel imaged with a 40X objective.

Eventually, a standard Spectral Angle Mapper (SAM), was applied to estimate the resemblance between the pixels of the image and the spectral library pixels saved in the CytoViva ENVI software folder. SAM performs by measuring the angle between the image and spectral libraries, using them as trajectories in n-D space where 'n' denotes the number of bands. The best spectral angle match was obtained when the angle between saved spectral libraries and specimen spectra was the least. After successfully mapping the DONBs identified with the SAM algorithm, it was quantified using Image pro premier 9.0 software (Media Cybernetics, Silver Spring, MD, USA) machine learning tool.

Example 2. Formulation Optimization (Table 2)

The present work involved a four-factor, three-level statistical optimization study to prepare DONBs and explore their application for intravitreal delivery. This design was used to explore quadratic response surfaces and construct second-order polynomial models using Design Expert (version 11.1.1.0, Stat-Ease Inc., Minneapolis, MN, USA). The polynomial equation for the experimental design is given as:

$$Y_0=b_0+b_1X_1+b_2X_2+b_3X_3+b_{12}X_1X_2+b_{13}X_1X_3+b23X2X3+b11X12+b22X22+b33X32$$

where $Y_0$ is the dependent variable, $b_0$ is the intercept, $b_i$ to $b_{33}$ are regression coefficients (computed from the observed experimental values) of Y, $X_1$, $X_2$, and $X_3$ (coded levels), which are the independent variables, $X_{i,j}$, and $X^2_i$ (I,j 1, 2, or 3) are the interaction and quadratic terms. The software-generated amounts of dextran ($X_1$), potassium ($X_2$), sonication power ($X_3$), and pH ($X_4$) were used to prepare different batches of DNOBs, and the responses observed are oxygen release ($Y_1$), % size ($Y_2$), and zeta potential ($Y_3$).

TABLE 2

Rotatable Central Composite Design (RCCD) Based DONBs Obtained Using Independent Variables and Their Effects on Dependent Response.

| | | | | | $Y_1$ (mmHg) | | $Y_2$ (nm) | | $Y_3$ (mV) | |
|---|---|---|---|---|---|---|---|---|---|---|
| Code | $X_1$ | $X_2$ | $X_3$ | $X_4$ | actual | predicted | actual | predicted | actual | predicted |
| $S_1$ | 1 | 0.1 | 50 | 4.5 | 555.67 ± 5.33 | 555.19 | 88.09 ± 5.33 | 87.01 | −32.11 ± 0.88 | −34.7 |
| $S_2$ | 0.75 | 0.055 | 60 | 5.75 | 461.33 ± 4.25 | 466.28 | 74.21 ± 4.56 | 74.99 | −28.52 ± 1.10 | −26.9 |
| $S_3$ | 0.75 | 0.145 | 40 | 5.75 | 452.37 ± 7.29 | 459.58 | 84.56 ± 3.03 | 85.29 | −27.36 ± 0.98 | −29.02 |
| $S_4$ | 0.5 | 0.1 | 50 | 7 | 347.12 ± 5.22 | 339.52 | 77.45 ± 4.13 | 78.19 | −23.66 ± 1.24 | −21.22 |
| $S_5$ | 0.75 | 0.055 | 40 | 8.25 | 412.76 ± 4.01 | 418.05 | 123.43 ± 5.76 | 124.47 | −11.63 ± 0.56 | −12.3 |
| $S_6$ | 0.5 | 0.01 | 30 | 7 | 342.79 ± 5.21 | 337.7 | 171.04 ± 5.22 | 172.54 | −17.63 ± 0.94 | −19.41 |
| $S_7^e$ | 0.75 | 0.055 | 40 | 5.75 | 451.76 ± 5.39 | 449.07 | 130.56 ± 4.67 | 129.63 | −27.65 ± 0.34 | −27.05 |
| $S_8$ | 1 | 0.01 | 30 | 4.5 | 510.01 ± 6.33 | 512.04 | 181.9 ± 5.09 | 181.58 | −33.65 ± 1.32 | −32.88 |
| $S_9$ | 1.25 | 0.055 | 40 | 5.75 | 582.09 ± 4.05 | 589.42 | 134.78 ± 5.32 | 134.59 | −26.54 ± 0.89 | −25.78 |
| $S_{10}$ | 1 | 0.01 | 50 | 4.5 | 555.21 ± 5.31 | 548.26 | 122.09 ± 5.09 | 124.28 | −32.58 ± 1.56 | −32.73 |
| $S_{11}^e$ | 0.75 | 0.055 | 40 | 5.75 | 445.67 ± 3.21 | 449.07 | 130.66 ± 5.33 | 129.63 | −27.68 ± 0.85 | −27.05 |
| $S_{12}$ | 1 | 0.1 | 50 | 7 | 525.98 ± 5.02 | 520 | 81.09 ± 5.88 | 81.12 | −19.68 ± 1.34 | −19.95 |
| $S_{13}^e$ | 0.75 | 0.055 | 40 | 5.75 | 446.21 ± 4.84 | 449.07 | 130.98 ± 4.08 | 129.63 | −27.68 ± 1.56 | −27.05 |
| $S_{14}$ | 0.5 | 0.1 | 30 | 7 | 345.01 ± 4.89 | 346.34 | 132.67 ± 3.98 | 130.08 | −22.96 ± 0.83 | −21.38 |
| $S_{15}^e$ | 0.75 | 0.055 | 40 | 5.75 | 451.98 ± 5.21 | 449.07 | 129.06 ± 4.09 | 129.63 | −27.68 ± 0.98 | −27.05 |
| $S_{16}$ | 0.5 | 0.1 | 30 | 4.5 | 398.67 ± 4.09 | 391.96 | 128.09 ± 5.45 | 130.25 | −31.52 ± 1.26 | −36.13 |
| $S_{17}$ | 1 | 0.1 | 30 | 4.5 | 547.89 ± 5.45 | 540.06 | 141.03 ± 4.09 | 141.49 | −32.68 ± 1.46 | −34.85 |
| $S_{18}$ | 0.25 | 0.055 | 40 | 5.75 | 262.43 ± 4.44 | 266.3 | 127.55 ± 5.33 | 127.72 | −26.86 ± 1.34 | −28.33 |
| $S_{19}$ | 0.75 | — | 40 | 5.75 | 440.04 ± 3.87 | 444.02 | 165.77 ± 4.88 | 165.02 | −26.75 ± 1.27 | −25.08 |
| $S_{20}$ | 1 | 0.1 | 30 | 7 | 511.88 ± 5.09 | 511.64 | 140.65 ± 5.22 | 140.69 | −21.66 ± 0.88 | −20.1 |
| $S_{21}$ | 0.75 | 0.055 | 20 | 5.75 | 430.64 ± 6.11 | 436.88 | 184.98 ± 3.66 | 184.18 | −26.84 ± 0.92 | −27.21 |
| $S_{22}$ | 0.5 | 0.01 | 50 | 4.5 | 395.77 ± 4.54 | 390.44 | 127.66 ± 5.29 | 128.04 | −31.03 ± 1.02 | −34.00 |
| $S_{23}^e$ | 0.75 | 0.055 | 40 | 5.75 | 443.47 ± 5.03 | 449.07 | 129.43 ± 4.03 | 129.63 | −32.07 ± 1.34 | −27.05 |
| $S_{24}$ | 1 | 0.01 | 30 | 7 | 505.07 ± 5.33 | 497.54 | 175.03 ± 4.33 | 175.84 | −13.64 ± 0.87 | −18.13 |
| $S_{25}$ | 1 | 0.01 | 50 | 7 | 525.86 ± 4.98 | 526.99 | 115.18 ± 5.78 | 113.44 | −15.76 ± 0.33 | −17.98 |
| $S_{26}$ | 0.75 | 0.055 | 40 | 3.25 | 479.03 ± 5.98 | 484.94 | 136.55 ± 4.33 | 135.48 | −41.66 ± 0.97 | −41.8 |
| $S_{27}^e$ | 0.75 | 0.055 | 40 | 5.75 | 455.35 ± 5.33 | 449.07 | 127.09 ± 5.63 | 129.63 | −34.5 ± 0.99 | −27.05 |

TABLE 2-continued

Rotatable Central Composite Design (RCCD) Based DONBs Obtained Using Independent Variables and Their Effects on Dependent Response.

| | | | | | $Y_1$ (mmHg) | | $Y_2$ (nm) | | $Y_3$ (mV) | |
|---|---|---|---|---|---|---|---|---|---|---|
| Code | $X_1$ | $X_2$ | $X_3$ | $X_4$ | actual | predicted | actual | predicted | actual | predicted |
| $S_{28}$ | 0.5 | 0.1 | 50 | 4.5 | 390.01 ± 4.56 | 391.91 | 84.66 ± 5.99 | 83.45 | −36.03 ± 1.03 | −35.97 |
| $S_{29}$ | 0.5 | 0.01 | 50 | 7 | 349.76 ± 5.33 | 351.97 | 118.68 ± 6.22 | 117.82 | −15.63 ± 1.36 | −19.25 |
| $S_{30}$ | 0.5 | 0.01 | 30 | 4.5 | 369.04 ± 5.02 | 369.4 | 178.09 ± 3.97 | 177.66 | −37.97 ± 0.94 | −34.16 |

[a]Dextran (% w/v).
[b]Potassium chloride (% w/v).
[c]Sonication power (watts).
[d]pH.
[e]Indicates center point of the design
$Y_1$ Oxygen release.
$Y_2$ Size.
$Y_3$ Zeta potential Oxygen release. The ($R^2$; Table 2 for oxygen was found to be 0.9956, indicating a good fit. The predicted $R^2$ of 0.9772 is in reasonable agreement with the adjusted $R^2$ of 09914. Adequate precision was used to measure the signal-to-noise ratio and found to be 64.861, indicating an adequate signal for the oxygen release.

Size of nanobubbles. The value of the correlation coefficient ($R^2$; Table 2) was found to be 0.9985, indicating a good fit. The predicted $R^2$ of 0.9930 is in reasonable agreement with the adjusted $R^2$ of 0.9971. The signal-to-noise ratio of 92.458 indicates an adequate signal for nanobubble size.

Zeta potential. For zeta potential, the ($R^2$ ; Table 2) shows a 0.8685 value indicating a good fit of the model, and the predicted $R^2$ of 0.8208 is in reasonable agreement with the adjusted $R^2$ of 0.8475. The signal-to-noise ratio of 25.381 indicates an adequate signal for the zeta potential of DONBs.

The model fitness was also confirmed by graphical analysis. See FIG. 11*a*, b, and c for the respective responses $Y_1$, $Y_2$, and $Y_3$. To improve the model, an appropriate transformation can be applied to the response data. In this case, we used none in the transformation of the model, and the software also suggested no transformation, which makes these models simpler for response evaluation. Design-Expert software recommends the most appropriate lambda value for the transformation from the location of the minimum in the Box-Cox plot. Lambda is the power raised by the response in transformation analysis. The Box-Cox plot for the model shown in FIG. 11*a*, b and c. The current lambda for response $Y_1$, $Y_2$, and $Y_3$ transformation was 1 for the three response variables, oxygen release, nanobubble size and zeta potential of nanobubbles. The current lambda falls between the confidence interval that makes the model suitable for evaluation of response. This indicates that the current transformation is the best power transformation which can be applied to the response data.

TABLE 3

Summary of Statistical Parameters for Responses Y1 (Oxygen release), Y2 (Size), and Y3 (Zeta potential) for Fitting to a Different Model.

| Statistical parameter | Oxygen release (mmHg) | Size (nm) | Zeta potential (mV) |
|---|---|---|---|
| R2 | 0.9956 | 0.9985 | 0.8685 |
| Adjusted R2 | 0.9914 | 0.9971 | 0.8475 |
| Predicted R2 | 0.9772 | 0.9930 | 0.8208 |

TABLE 3-continued

Summary of Statistical Parameters for Responses Y1 (Oxygen release), Y2 (Size), and Y3 (Zeta potential) for Fitting to a Different Model.

| Statistical parameter | Oxygen release (mmHg) | Size (nm) | Zeta potential (mV) |
|---|---|---|---|
| SD | 7.05 | 1.67 | 2.85 |
| % CV | 1.58 | 1.29 | 10.52 |
| model | Quadratic | Quadratic | Linear |

Example 3. Results of Optimized ONBs

TABLE 4

Typical oxygen release statistic based on the oxygen concentration curve.

| | Low point | Concentration @6 h | % Change @6 h |
|---|---|---|---|
| Control | 4.27 | 5.78 | 35.36 |
| Epikuron 0.3 ml | 4.79 | 6.23 | 30.06 |
| Epikuron 0.6 ml | 3.81 | 5.41 | 41.99 |
| Epikuron 1.2 ml | 4.29 | 5.95 | 38.69 |
| Dextran 0.5 ml | 4.28 | 5.56 | 29.91 |
| Dextran 2.0 ml | 3.8 | 4.71 | 23.95 |
| Trehalose 0.2 ml | 3.94 | 5.24 | 32.99 |
| Trehalose 0.8 ml | 4.15 | 5.17 | 24.58 |

The change @6 h is the change in oxygen concentration between that at 6 hour and the low point.
The % change @6 h is the ratio between the change @6 h and the low point. It indicates the increase of oxygen concentration during the measurement, which is primarily attributed to the oxygen release from ONBs.
The oxygen curve and corresponding statistic is conducted with ONBs from different formulation after serial storage time.

Figure 16:
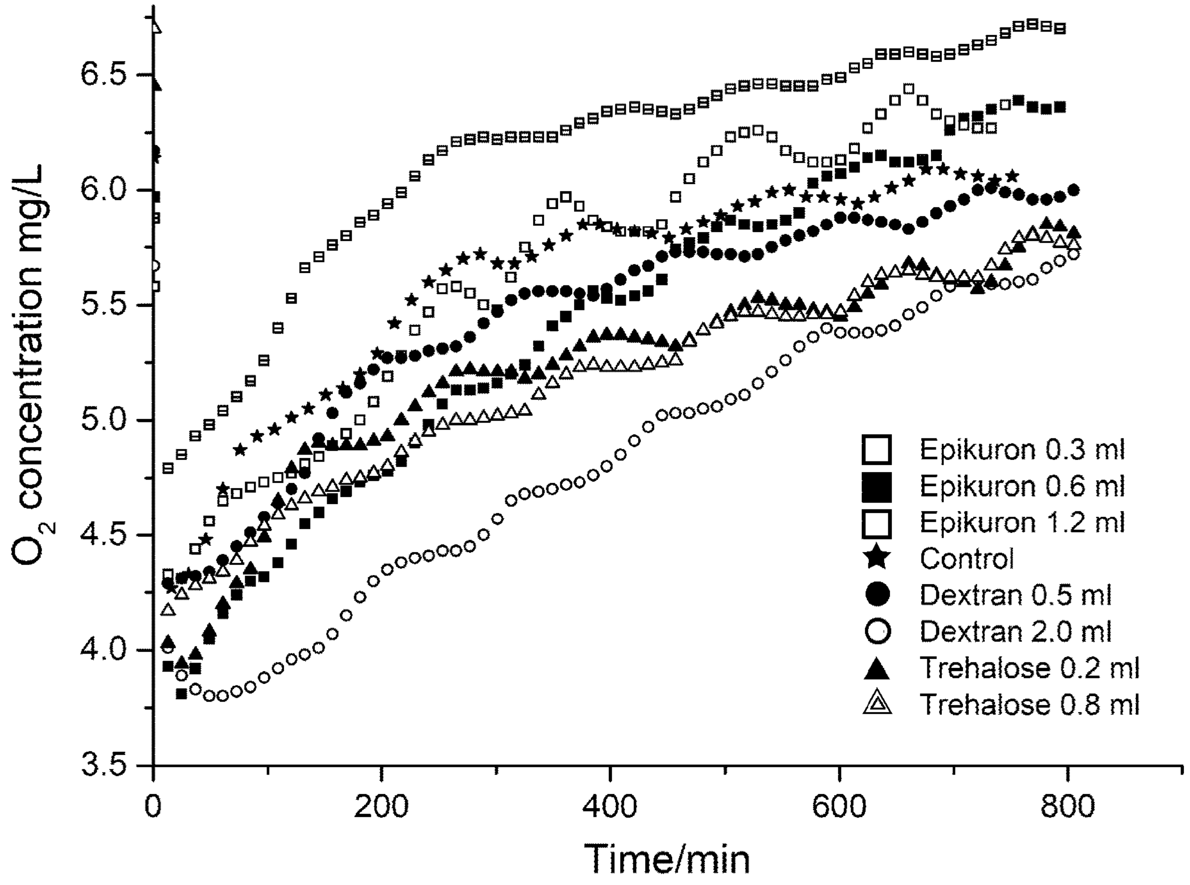
FIG. 16. Typical oxygen concentration curve. Increase in oxygen concentration is primarily attributed to oxygen release from ONBs. Graph shows the typical $O_2$ released from the nanobubbles into the medium in which it is suspended. The oxygen is released from the bubbles into the medium (the increase in the concentration of the medium is measured). Control is oxygen saturated water by blowing oxygen into water for 1 hour and stored at the same condition as ONBs.

Table 4 shows a maximal change in oxygen concentration when 0.6 ml of Epikuron was used (FIG. 16), wherein the size of the ONBs is 218.71 nm ±51.05 nm and the Zeta potential is −58.8 mV ±1.3 mV. In other formulations, the size of the ONBs is 119.6 nm ±44.9 nm and the Zeta potential is −35.54 mV ±10.54 mV. The latter smaller size obtained in the other formulation results from using 0.06 wt % KCl. To further increase the size to about 200 nm; we decreased the KCl to 0.045 wt % to make bigger particles that contain more oxygen. Thus the formulations can be adjusted for sizing the diameter of ONBs to about 200 nm and the ONBs can be made larger or smaller depending on the amount of KCl.

Various properties, such as oxygen release, diameter, zeta potential, even the morphology and surface properties of ONBs can be controlled during synthesis. See also FIG. 17 to FIG. 22 for the effect on release of oxygen under various conditions.

Figure 17:
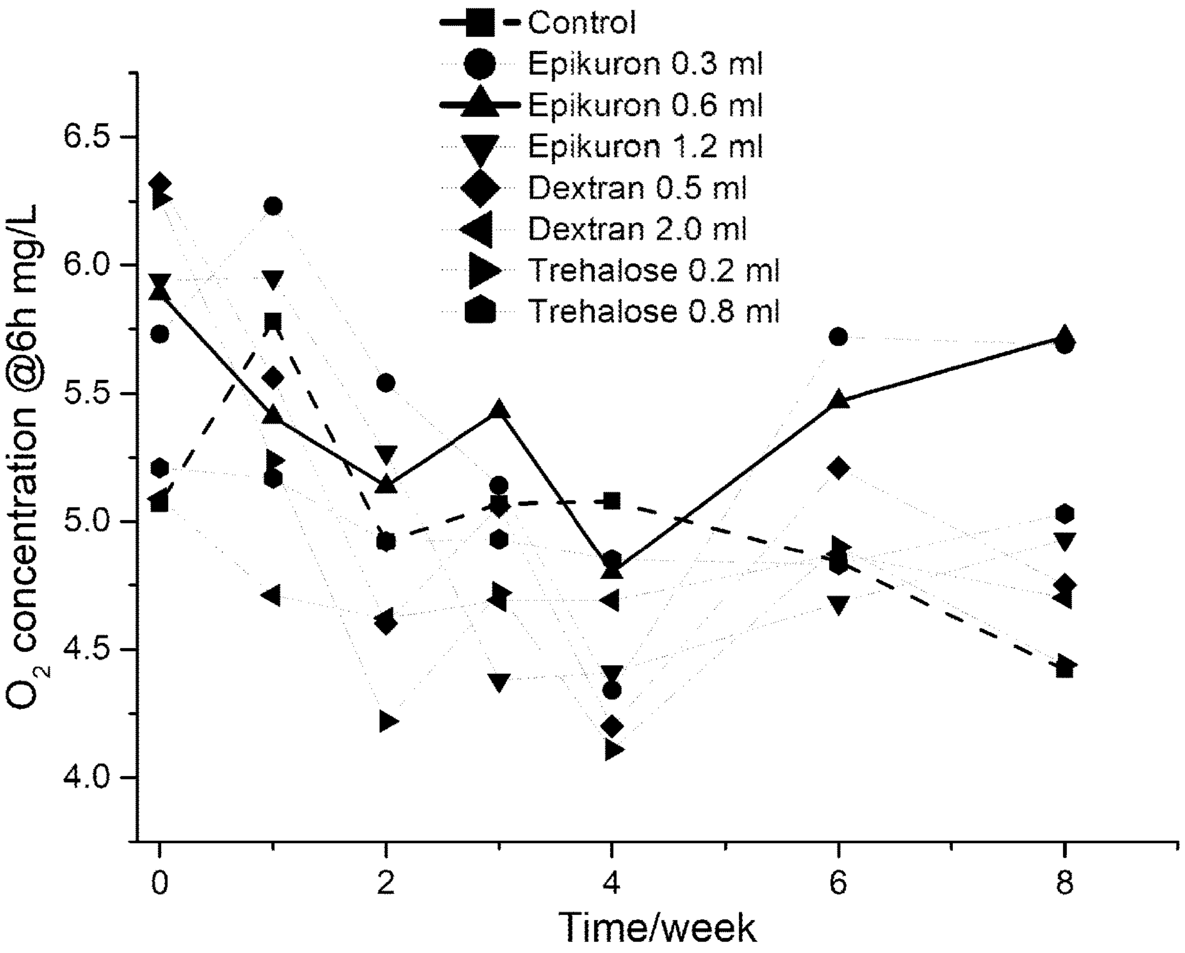
FIG. 17. The oxygen concentration at 6 hour in the measurement upon storage. The ONBs with 0.6 ml of Epikuron maintains similar oxygen concentration after 6 hour of release in samples stored at different time periods. In contrast, the oxygen concentration of the samples with control, oxygen saturated water stored at the same condition, is much lower. This shows that the ONBs can retain oxygen much better than oxygen saturated water. Legend refers to formulations A to G in Example 3.

In FIG. 17, the preferred ONB formulation (labeled as Epikuron 0.6 ml) increases the oxygen concentration significantly compared with that with control (oxygen saturated water stored at the same condition as ONBs) even after stored for 8 weeks, indicating a good storage of oxygen in our ONBs. The dextran-based multifunctional shell of ONBs enables the oxygen storage at different temperature from 4° C. to room temperature. Even at 37° C. the ONBs show good oxygen retention capability, which greatly benefits the transportation and storage of the ONBS. Besides the storage capability, the disclosed ONBs release oxygen in a wide pH range from pH 4.5 to pH 8.3, which enable the usage of the ONBs for various conditions. The ONBs also release significant amounts of oxygen in various media, including high ionic strength solution and simulated vitreous humor.

Figure 18:
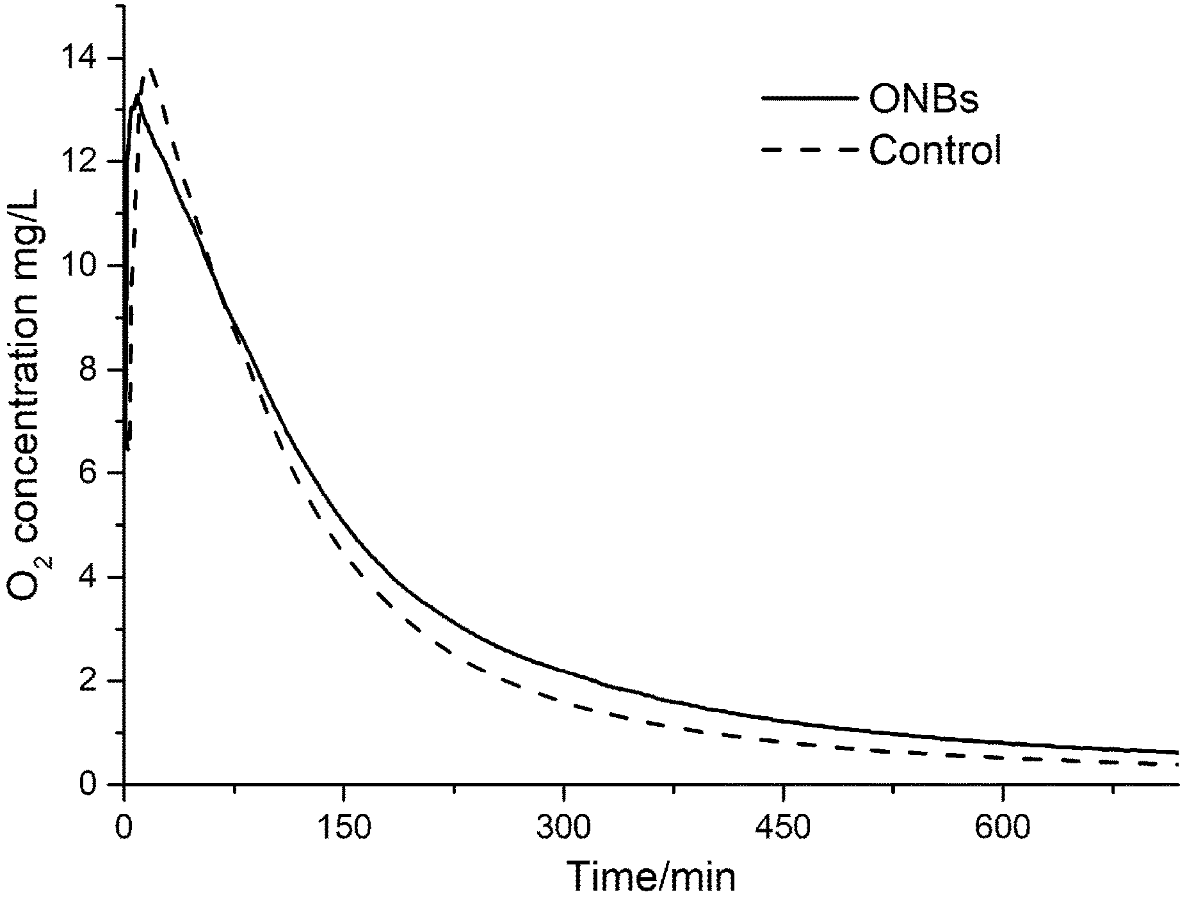
FIG. 18. $O_2$ release from ONBs in hypoxia chamber at 37° C. The difference between ONBs sample and control shows that the ONBs could maintain a higher oxygen concentration in the test sample, clearly demonstrating the oxygen release of ONBs. The $O_2$ release in hypoxia chamber at 37° C. The control is water without ONBs of which the $O_2$ concentration is adjusted to be similar to ONBs sample, while ONBs sample is mixture of ONBs and low oxygen water (4:6). Release curve up to 12 hours is shown.
Figure 19:
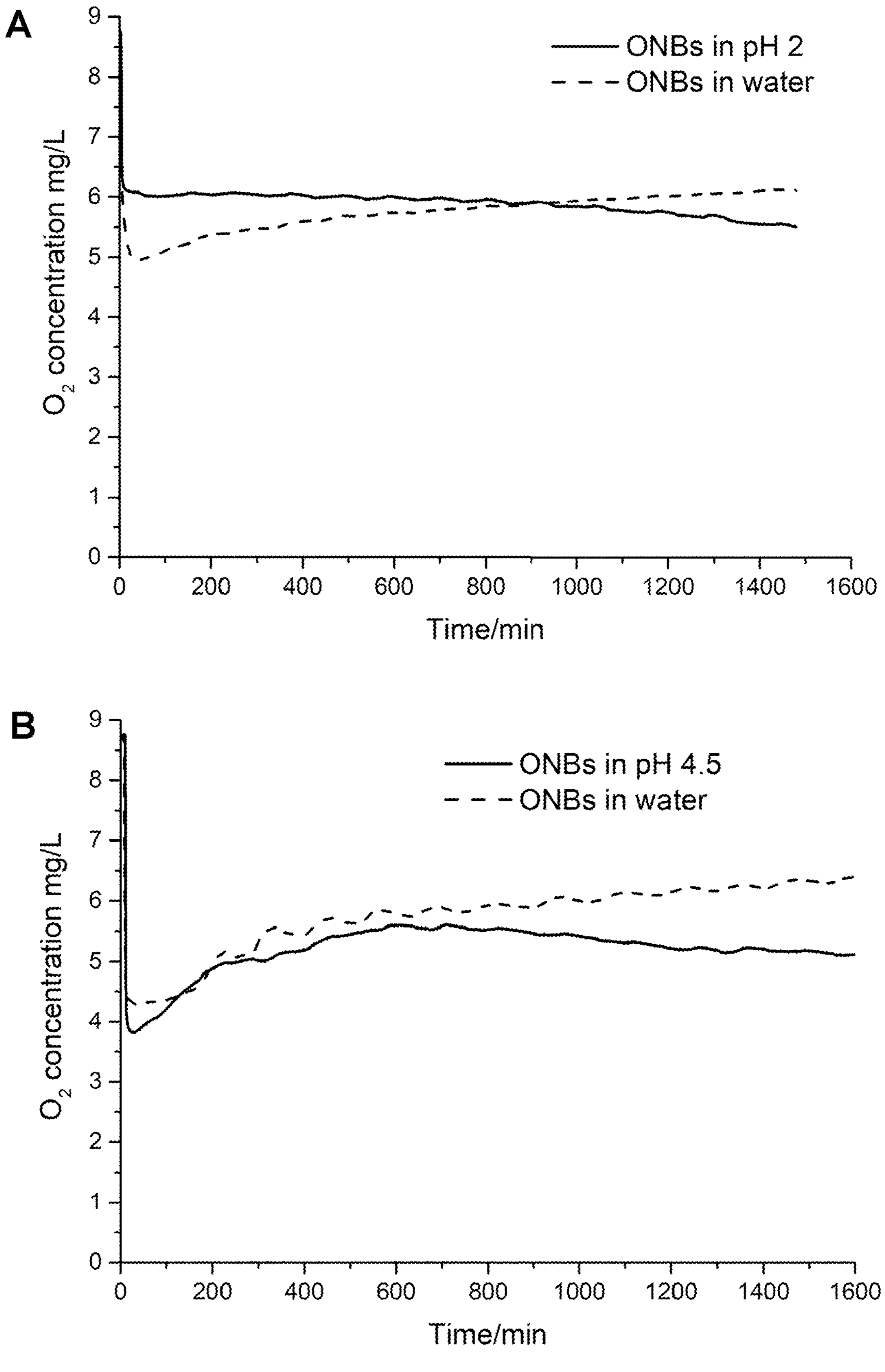
FIG. 19. $O_2$ release from ONBs at different pH. Low pH influences the $O_2$ release from ONBs at longer time periods, but in the first few hours the difference is not significant. The pH 2 and 12 solution was prepared with addition of NaOH and HCl respectively. The pH 4.5 is in MES buffer. The pH 8.3 is in Tris/glycine buffer.
Figure 19:
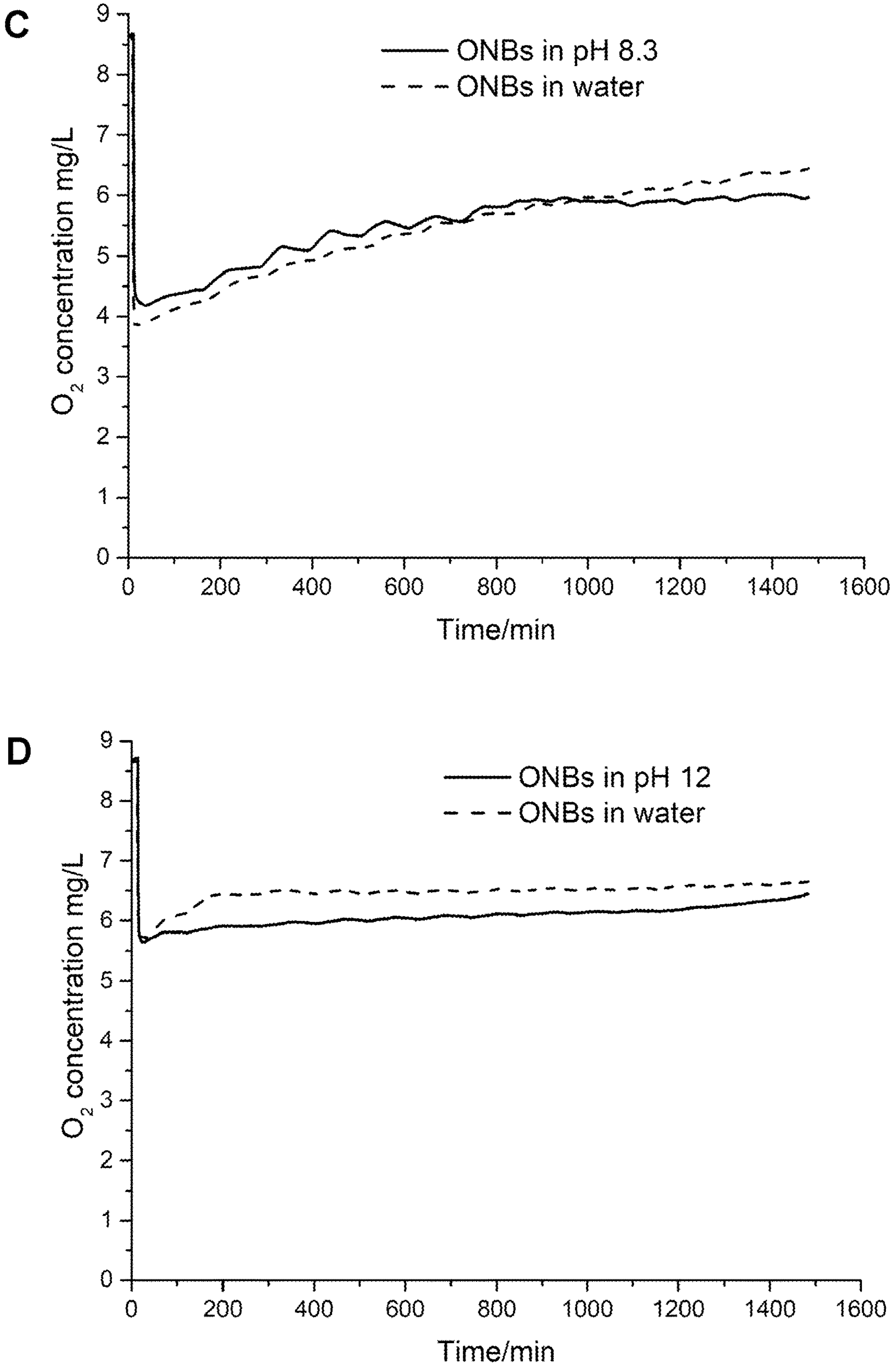
Figure 20:
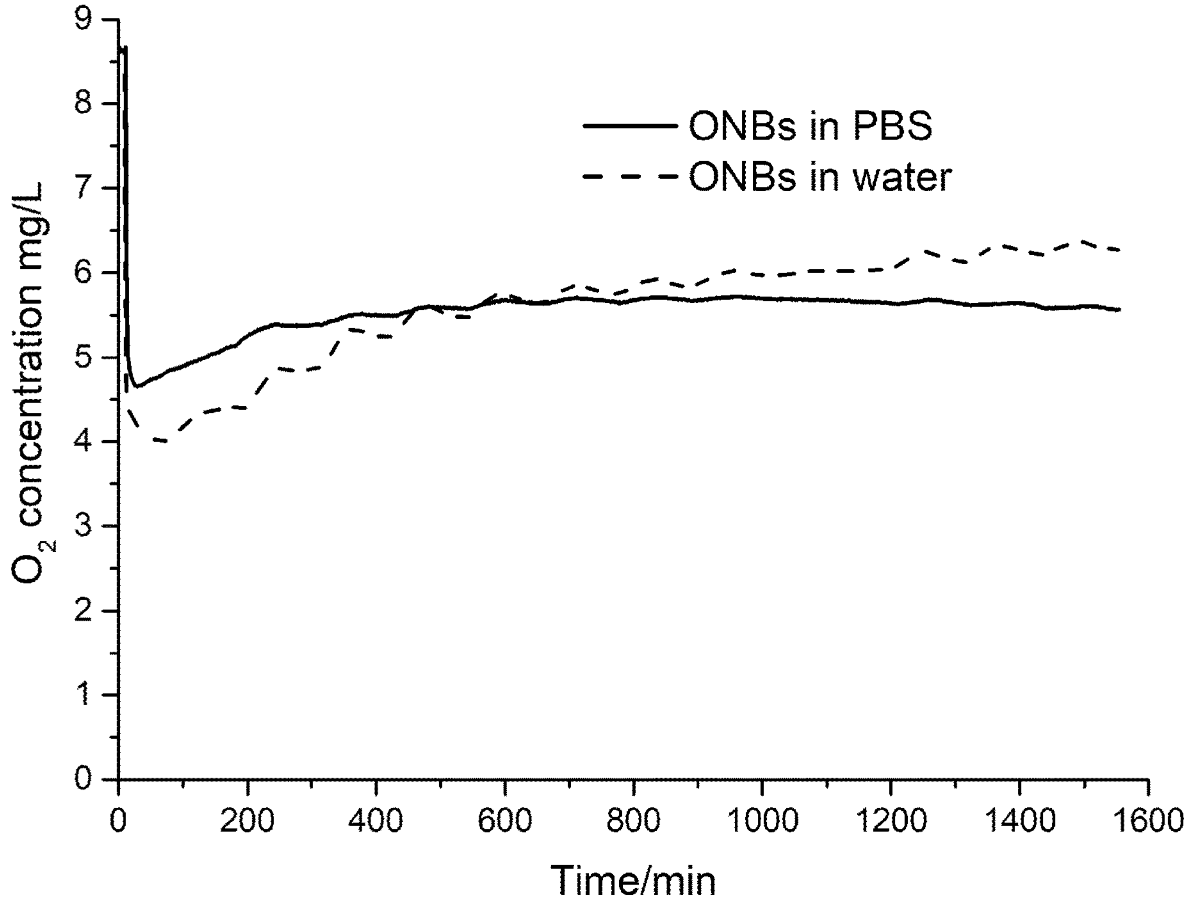
FIG. 20. $O_2$ release from ONBs in PBS: High ionic strength makes the oxygen concentration in the first few hours higher than that in water but lower after prolonged time. High ionic strength increases the oxygen release rate but limits the total amount of released oxygen.
Figure 21:
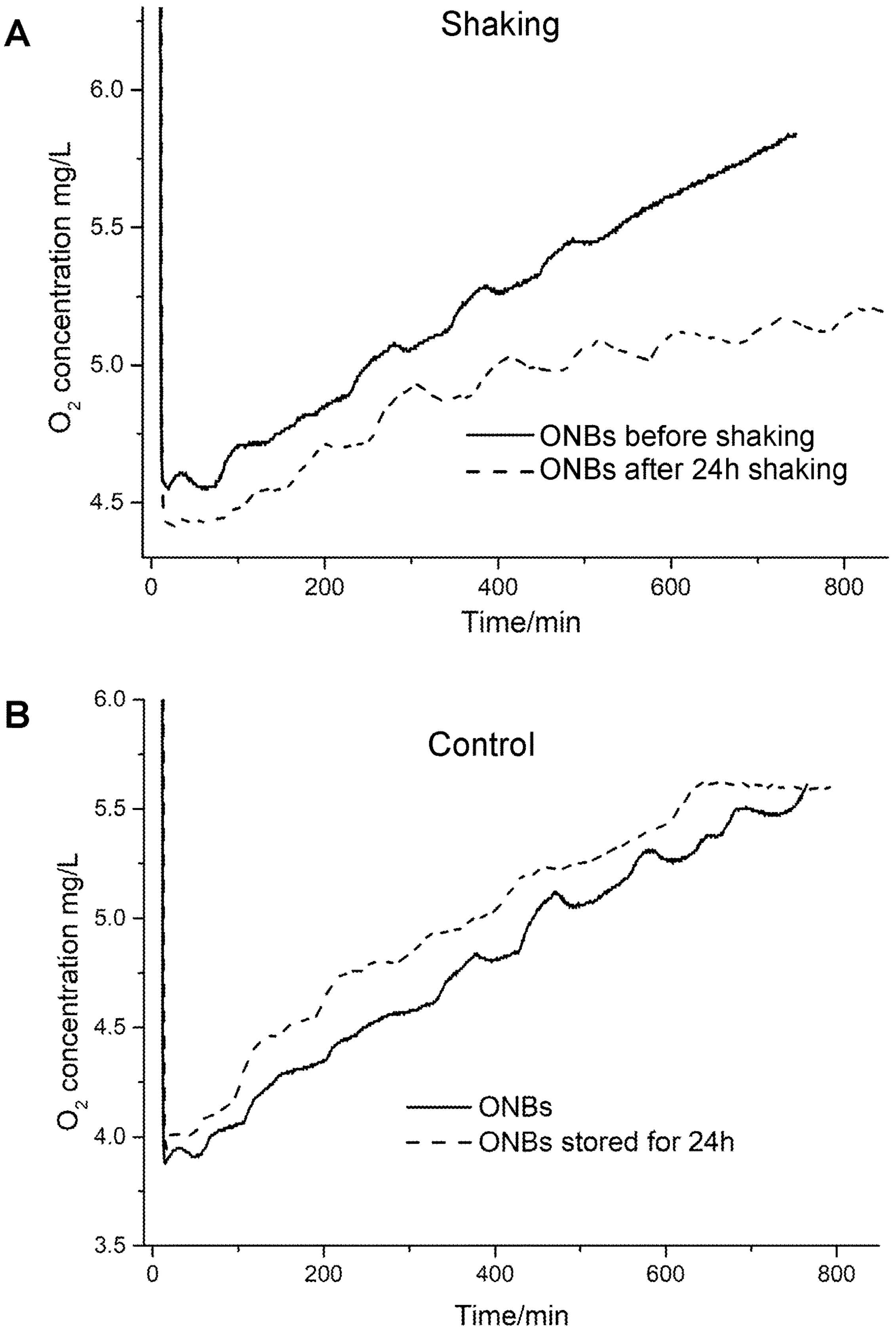
FIG. 21. $O_2$ release from ONBs after shaking. Shaking influenced the oxygen in ONBs, which induce the less increase in oxygen concentration during the test. Control samples is the ONBs stored without shaking.
Figure 22:
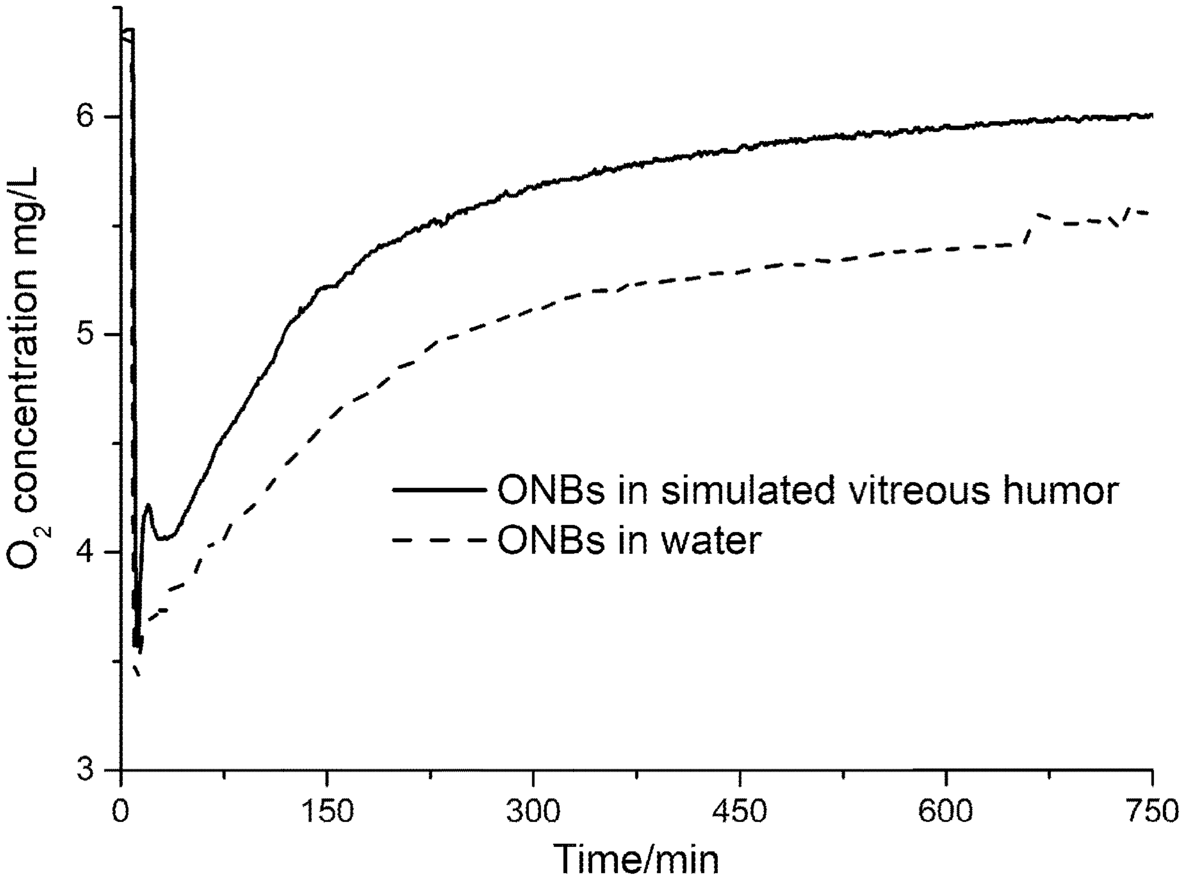
FIG. 22. $O_2$ release from ONBs in simulated vitreous humor at 37° C. Based on the $O_2$ concentration: with 0.39 ml ONBs solution (10% of the total volume of the test sample) the oxygen concentration increases 2.2 mg/L in simulated vitreous humor and ~1.8 mg/L in water after 6-hour release. Based on the $O_2$ amount (weight): the increase in oxygen level in test samples over 6 hours is −8.4 mg in simulated vitreous humor and −6.9 mg in water, which is primarily attributed to −0.39 ml of ONBs solution. The volume of the test sample is ~3.9 ml which contains −0.39 ml ONBs.

As shown in FIG. 18, it can be seen that the ONBs continuously provide oxygen up to 24 hours to the solution sample in a hypoxia chamber. This result demonstrates the higher oxygen concentration achieved added with ONBs compared to that of the control sample without ONBs. The data shows release of oxygen even after1600 min in duration.

The synthesis procedure for the ONBs is robust, and suitable for large-scale industrial production. The substrates for the synthesis are cost-effective and easy to access, meanwhile the synthesis requires simple instrumentation, thus facilitating the commercialization of the ONBs.

Ingredients in a synthesis for an optimized ONB:

Percentages given are concentration of the ingredient expressed as % in the respective solution. Eg. "KCl 0.2 ml, 0.045 wt %" means that the KCl concentration is 0.045 wt % in the 0.2 ml KCl solution added in the synthesis. The formulation is prepared with the primary ingredients, Epikuron (lecithin), dextran and trehalose (FIG. 17).

A. Sample labelled as "Epikuron 0.6 ml"
  In 10 ml water
  KCl: 0.2 ml, 0.045 wt %
  Epikuron: 0.6 ml, 0.23 wt %
  TPGS: 0.4 ml, 0.028 wt %
  Dextran: 1 ml, 0.9 wt %
  Palmitic acid: 0.3 ml 0.19 wt %
  Trehalose: 0.4 ml, 0.4 wt %.

Component amounts expressed as % wt in the formulation:
  Weight percent:
  KCl: $6.98\times10^{-4}$ wt %
  Epikuron: $1.07\times10^{-2}$ wt %
  TPGS: $8.68\times10^{-4}$ wt %
  Dextran: $6.98\times10^{-2}$ wt %
  Palmitic Acid: $4.42\times10^{-3}$ wt %
  Trehalose: $1.24\times10^{-2}$ wt %

Other formulations prepared:

B. Sample labelled as "Epikuron 0.3 ml"
  in 10 ml water
  KCl: 0.2 ml, 0.045 wt %
  Epikuron: 0.3 ml, 0.23 wt %
  TPGS: 0.4 ml, 0.028 wt %
  Dextran: 1 ml, 0.9 wt %
  Palmitic acid: 0.3 ml 0.19 wt %
  Trehalose: 0.4 ml, 0.4 wt %

C. Sample labelled as "Epikuron 1.2 ml"
  in 10 ml water
  KCl: 0.2 ml, 0.045 wt %
  Epikuron: 1.2 ml, 0.23 wt %
  TPGS: 0.4 ml, 0.028 wt %
  Dextran: 1 ml, 0.9 wt %
  Palmitic acid: 0.3 ml 0.19 wt %
  Trehalose: 0.4 ml, 0.4 wt %

D. Sample labelled as "Dextran 0.5 ml"
  in 10 ml water
  KCl: 0.2 ml, 0.045 wt %
  Epikuron: 0.6 ml, 0.23 wt %
  TPGS: 0.4 ml, 0.028 wt %
  Dextran: 0.5 ml, 0.9 wt %
  Palmitic acid: 0.3 ml 0.19 wt %
  Trehalose: 0.4 ml, 0.4 wt %

E. Sample labelled as "Trehalose 0.2 ml"
  in 10 ml water
  KCl: 0.2 ml, 0.045 wt %
  Epikuron: 0.6 ml, 0.23 wt %
  TPGS: 0.4 ml, 0.028 wt %
  Dextran: 1.0 ml, 0.9 wt %
  Palmitic acid: 0.3 ml 0.19 wt %
  Trehalose: 0.2 ml, 0.4 wt %

F. Sample labelled as "Dextran 2.0 ml"
  in 10 ml water
  KCl: 0.2 ml, 0.045 wt %
  Epikuron: 0.6 ml, 0.23 wt %
  TPGS: 0.4 ml, 0.028 wt %
  Dextran: 2.0 ml, 0.9 wt %
  Palmitic acid: 0.3 ml 0.19 wt %
  Trehalose: 0.4 ml, 0.4 wt %

G. Sample labelled as "Trehalose 0.8 ml"
  in 10 ml water
  KCl: 0.2 ml, 0.045 wt %
  Epikuron: 0.6 ml, 0.23 wt %
  TPGS: 0.4 ml, 0.028 wt %
  Dextran: 1.0 ml, 0.9 wt %
  Palmitic acid: 0.3 ml 0.19 wt %
  Trehalose: 0.8 ml, 0.4 wt %

The combination of KCl, Trehalose and TPGS for the preparation of ONBs was formulated for compatibility with administration to the eye. The significance of the composition is described as follows:

Potassium Chloride: Unlike the other polymeric shelled oxygen nano-/micro-structures, we use potassium chloride to tune the properties, e.g., the size and zeta potential, of the disclosed ONBs. Using a Rotatable Central Composite Design, the influence of potassium chloride to the size and the zeta potential of the obtained ONBs was investigated, and the results are shown in Table 1, Table 2 and FIG. 12-14. These results provide a valuable way to tune the properties of ONBs by changing the amount of potassium chloride in the synthesis. The influence on the negative charges are important for particle movement in the tissues.

Trehalose and D-a-Tocopherol poly-(ethylene glycol) 1000 succinate (TPGS): TPGS reduces the surface tension and benefits the self-assembly process in the synthesis of ONBs. Trehalose improves the stability of the ONBs by shielding attractive forces between ONBs to prevent aggregation. These components used in the synthesis of dextran-based ONBs improve the properties of ONBs for the clinical usage.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition free of perfluorocarbons comprising:
polysaccharide nanobubbles wherein the nanobubbles comprise a self-assembled colloidal shell that encapsulates an interior cargo;
the shell comprising dextran, trehalose, lecithin, palmitic acid, and tocopherol; and
an electrolyte;
wherein the nanobubbles have an average diameter of about 200 nm or more and the composition has a zeta potential of about −75 mV to about −50 mV.

2. The composition of claim 1 wherein the cargo of the nanobubbles comprises oxygen gas ($O_2$).

3. The composition of claim 1 wherein the composition comprises about $2\times10^{-2}$ wt % to about $10\times10^{-2}$ wt % dextran.

4. The composition of claim 3 wherein dextran has an average molecular weight of about 100 kDa to about 300 kDa.

5. The composition of claim 1 wherein the composition comprises about $0.5\times10^{-2}$ wt % to about $5\times10^{-2}$ wt % trehalose.

6. The composition of claim 1 wherein the composition comprises about $0.5\times10^{-2}$ wt % to about 5 $\mathbf{\times10^{-2}}$ wt % lecithin.

7. The composition of claim 6 wherein the lecithin is a soy lecithin.

8. The composition of claim 1 wherein the composition comprises about $1\times10^{-3}$ wt % to about $10\times10^{-3}$ wt % palmitic acid.

9. The composition of claim 1 wherein the composition comprises about $3\times10^{-4}$ wt % to about $30\times10^{-4}$ wt % tocopherol.

10. The composition of claim 9 wherein tocopherol is alpha-tocopherol.

11. The composition of claim 1 wherein the electrolyte comprises a mineral salt.

12. The composition of claim 11 wherein the composition comprises about $2\times10^{-4}$ wt % to about $20\times10^{-4}$ wt % w/v mineral salt.

13. The composition of claim 12 wherein the mineral salt is potassium chloride.

14. The composition of claim 1 wherein the zeta potential is about −65 mV to about −55 mV, and the diameter is about 165 nm to about 270 nm.

15. The composition of claim 1 wherein the composition comprises about $6.98\times10^{-2}$ wt % dextran, about $1.24\times10^{-2}$ wt % trehalose, about $1.07\times10^{-2}$ wt % lecithin, about $4.42\times10^{-3}$ wt % palmitic acid, about $8.68\times10^{-4}$ wt % tocopherol, and the electrolyte comprises about $6.98\times10^{-4}$ wt % potassium chloride.

16. A method for treating ocular ischemia comprising:
administering to the interior of an ischemic eye of a subject in need of therapy for ocular ischemia an effective dose of the composition according to claim 1;
wherein the composition comprises a plurality of nanobubbles containing an interior cargo of oxygen gas; and
the nanobubbles disintegrate after administration to release the oxygen, thereby treating ocular ischemia in the subject.

17. The method of claim 16 wherein the amount of oxygen released per microliter of the nanobubble composition is at least 500 nanoliters per minute.

18. The method of claim 17 wherein the effective dose is at least 5 microliters of the composition.

19. The method of claim 16 wherein treatment comprises more than one effective dose.

20. The method of claim 16 wherein the ocular ischemia is retina hypoxia.

* * * * *